US010364236B2

(12) United States Patent
Brownstein

(10) Patent No.: US 10,364,236 B2
(45) Date of Patent: *Jul. 30, 2019

(54) COMPOSITIONS AND METHODS FOR TREATING NEURODEGENERATIVE DISEASES

(71) Applicant: Azevan Pharmaceuticals, Inc., Bethlehem, PA (US)

(72) Inventor: Michael J. Brownstein, Rockville, MD (US)

(73) Assignee: Azevan Pharmaceuticals, Inc., Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/786,772

(22) Filed: Oct. 18, 2017

(65) Prior Publication Data

US 2018/0201608 A1 Jul. 19, 2018

Related U.S. Application Data

(63) Continuation of application No. 15/129,190, filed as application No. PCT/US2015/023060 on Mar. 27, 2015, now Pat. No. 9,802,925.

(60) Provisional application No. 61/971,862, filed on Mar. 28, 2014.

(51) Int. Cl.

| C07D 413/04 | (2006.01) |
| C07D 413/14 | (2006.01) |
| A61K 31/4525 | (2006.01) |
| A61K 31/4545 | (2006.01) |
| A61K 31/454 | (2006.01) |
| A61K 31/422 | (2006.01) |
| A61K 45/00 | (2006.01) |
| A61K 31/397 | (2006.01) |
| A61K 31/4025 | (2006.01) |
| A61K 31/4178 | (2006.01) |
| A61K 31/4453 | (2006.01) |
| A61K 31/496 | (2006.01) |
| A61P 25/28 | (2006.01) |

(52) U.S. Cl.
CPC .......... *C07D 413/04* (2013.01); *A61K 31/397* (2013.01); *A61K 31/4025* (2013.01); *A61K 31/4178* (2013.01); *A61K 31/422* (2013.01); *A61K 31/4453* (2013.01); *A61K 31/496* (2013.01); *A61K 45/00* (2013.01); *A61P 25/28* (2018.01); *C07D 413/14* (2013.01)

(58) Field of Classification Search
None
See application file for complete search history.

(56) References Cited

U.S. PATENT DOCUMENTS

| 3,912,743 A | 10/1975 | Christensen |
| 4,007,196 A | 2/1977 | Christensen |
| 4,085,225 A | 4/1978 | Welle |
| 4,136,193 A | 1/1979 | Bogeso |
| 4,314,081 A | 2/1982 | Molloy |
| 4,341,698 A | 7/1982 | Carr |
| 4,352,752 A | 10/1982 | Ojima |
| 4,478,836 A | 10/1984 | Mouzin |
| 4,536,518 A | 8/1985 | Welch, Jr. |
| 4,576,753 A | 3/1986 | Kamiya |
| 4,734,498 A | 3/1988 | Cooper |
| 4,751,299 A | 6/1988 | Sugawara |
| 4,761,501 A | 8/1988 | Husbands |
| 4,772,694 A | 9/1988 | Cooper |
| 4,956,388 A | 9/1990 | Robertson |
| 5,011,472 A | 4/1991 | Aebischer |
| 5,023,252 A | 6/1991 | Hseih |
| 5,246,943 A | 9/1993 | Blankley |
| 5,338,744 A | 8/1994 | Dudley |
| 5,759,865 A | 6/1998 | Bruns |
| 6,054,453 A | 4/2000 | Lohray |
| 6,054,457 A | 4/2000 | Setoi |
| 6,204,260 B1 | 3/2001 | Bruns, Jr. |
| 6,403,632 B1 | 6/2002 | Duan |
| 6,610,680 B1 | 8/2003 | Bruna, Jr. |
| 6,627,625 B1 | 9/2003 | Koppel |
| 7,119,083 B2 | 10/2006 | Bruns, Jr. |
| 7,179,907 B2 | 2/2007 | Eaton |
| 7,268,125 B2 | 9/2007 | Bruns, Jr. et al. |

(Continued)

FOREIGN PATENT DOCUMENTS

| CA | 2615813 | 1/2007 |
| CN | 1106802 | 8/1995 |

(Continued)

OTHER PUBLICATIONS

Ojima, Iwao, Takeo Komata, and Xiaogang Qiu. "Asymmetric alkylations of a phenylalanylglycinate equivalent. Novel route to dipeptides bearing. alpha.-alkyl-. alpha.-amino.acid residues." Journal of the American Chemical Society 112.2 (1990): 770-774.

(Continued)

*Primary Examiner* — Michael Barker
(74) *Attorney, Agent, or Firm* — Brannon Sowers & Cracraft PC

(57) ABSTRACT

Compounds, and compositions, methods, and uses thereof, are described herein for treating neurodegenerative diseases and disorders. In particular, vasopressin receptor modulators, and compositions, methods and uses thereof, are described herein for treating neuropsychiatric aspects of neurodegenerative diseases such as Huntington's Disease, Parkinson's Disease, and Alzheimer's Disease.

22 Claims, 6 Drawing Sheets

(56) References Cited

U.S. PATENT DOCUMENTS

| | | |
|---|---|---|
| 8,048,874 B2 | 11/2011 | Koppel |
| 9,376,424 B2 | 6/2016 | Brownstein |
| 9,597,314 B2 | 3/2017 | Koppel |
| 9,802,925 B2 * | 10/2017 | Brownstein ......... C07D 413/04 |
| 2004/0132714 A1 | 7/2004 | Zhou et al. |
| 2004/0266750 A1 | 12/2004 | Bruns |
| 2005/0059650 A1 | 3/2005 | Jones et al. |
| 2006/0217364 A1 | 9/2006 | Bruns |
| 2006/0281728 A1 | 12/2006 | Guillon |
| 2008/0033165 A1 | 2/2008 | Koppel |
| 2008/0076754 A1 | 3/2008 | Xiang |
| 2008/0280870 A1 | 11/2008 | Kopopel |
| 2009/0170825 A1 | 7/2009 | Koppel |
| 2010/0016274 A1 | 1/2010 | Koppel |
| 2010/0137402 A1 | 6/2010 | Ducoux |
| 2010/0317652 A1 | 12/2010 | Bryans |
| 2011/0059935 A1 | 3/2011 | Bruns |
| 2011/0071160 A1 | 3/2011 | Couturier |
| 2017/0174670 A1 | 6/2017 | Brownstein |

FOREIGN PATENT DOCUMENTS

| | | | |
|---|---|---|---|
| CN | 2000504731 | 4/2000 | |
| CN | 1272111 | 11/2000 | |
| CN | 1606554 A | 4/2005 | |
| EP | 0144840 A2 | 2/1985 | |
| EP | 0591040 A1 | 4/1994 | |
| EP | 1558598 | 8/2005 | |
| JP | S56125361 A | 10/1981 | |
| WO | 9316609 A1 | 9/1993 | |
| WO | 1993016609 | 9/1993 | |
| WO | 1994001402 | 1/1994 | |
| WO | 9404494 A1 | 3/1994 | |
| WO | 1994004494 | 3/1994 | |
| WO | 9426735 A1 | 11/1994 | |
| WO | 1994026735 | 11/1994 | |
| WO | 199730707 A1 | 8/1997 | |
| WO | 1997030707 | 8/1997 | |
| WO | 200212187 A1 | 2/2002 | |
| WO | 2002012187 | 2/2002 | |
| WO | 03031407 A2 | 4/2003 | |
| WO | 2004037809 | 5/2004 | |
| WO | 06061407 A2 | 6/2006 | |
| WO | 2006102283 A2 | 9/2006 | |
| WO | 2006102308 | 9/2006 | |
| WO | WO-2006102308 A2 * | 9/2006 | ......... A61K 31/397 |
| WO | 2007109615 | 9/2007 | |
| WO | 2014127350 | 8/2014 | |
| WO | 2015148962 | 10/2015 | |
| WS | 9401402 A1 | 1/1994 | |

OTHER PUBLICATIONS

PCT International Search Report for PCT/US2007/006555 completed by the US Searching Authority on Jun. 16, 2008.

Hakimelahi, 'The Synthesis of Highly Strainerd Monocyclic and Bicyclic Beta-Lactams (delta-carbapenem)' Helvetica Chimica Acta (1982) vol. 65 Fasc. 5 pp. 1378-1384.

Serradeil-Le Gal, C., et al. "Biochemical and pharmacological properties of SR 49059, a new, potent, nonpeptide antagonist of rat and human vasopressin V1a receptors." Journal of Clinical Investigation 92.1 (1993):224.

PCT International Search Report for PCT/US2007/064309 completed by the US Searching Authority on Oct. 1, 2007.

Ragner Liedman et al., 'Intrauterine pressure, ischemia markers, and experienced pain during administration of a vasopressin via receptor antagonist in spontaneous and vasopressin-induced dysmenorrhea]', Acta Obstetricia et Gynecologica. 85: 207-211, (2005).

R. Brouard et al., 'Effect of SR49059, an orally active via vasopressin receptor antagonist, in the prevention of dysmenorrhoea', British Journal of Obstetrics and Gynecology, May 2000, vol. 107, pp. 614-619.

Ojima, Iwao, and Xiaogang Qiu. "Asymmetric alkylation of chiral. beta.-lactam ester enolates. A new approach to the synthesis of. alpha.-alkylated. alpha.-amino acids." Journal of the American Chemical Society 109.21 (1987): 6537-6538.

Ojima, Iwao, and Hauh-Jyun C. Chen. "Novel and effective routes to optically pure amino acids, dipeptides, and their derivatives via ??² lactams obtained through asymmetric cycloaddition." Journal of the Chemical Society, Chemical Communications 8 (1987): 625-626.

International Search Report and Written Opinion for PCT/US2007/078451 completed Apr. 23, 2008.

International Search Report and Written Opinion for PCT/US2006/010192 completed Jul. 1, 2008.

Japanese Translation of PCT International Application No. 2000-504731.

Japanese Patent Application Laid-open Publication No. 60-112757.

Chemical Abstracts AN:1992:6288, 1990.

Ghosh, M. et al, Journal of the Indian Chemical Society, 1985, 62(6), pp. 457-459.

Petit, Samuel, and G??Orard Coquerel. "The amorphous state." Polymorphism: In the Pharmaceutical Industry 10 (2006): 1.

International Search Report and Written Opinion for PCT/US2015/023060 completed Jun. 24, 2015.

Sampans, Fotini, et al. "Evaluation of the effects of Neptune Krill Oil™ on the management of premenstrual syndrome and dysmenorrhea." Alternative medicine review 8.2 (2003): 171-179.

Dickerson, Lori M., Pamela J. Mazyck, and Melissa H. Hunter. "Premenstrual syndrome." American family physician 67.8 (2003): 1743-1752.

Treatment Improvement Protocol (TIP) Series 5.1 HHS Publication No. (SMA) Sep. 4426. Rockville, MD: Substance Abuse and Mental Health Services Administration (2009); Appendix E: DSM-IV-TR Criteria for Posttraumatic Stress Disorder.

Jarrahpour, A.A., et al., 'Asymmetric Synthesis and Antimicrobial Activity of Some New Mono and Bicyclic .beta.-Lactams,' Molecules, 2004, vol. 9, pp. 939-948.

Jarrahpour, A.A., et al., 'Asymmetric Synthesis of a New Monocyclic beta.-Lactam as a potential biological active compound,' Molecules, 2005, M439.

PCT International Search Report for PCT/US2006/027703, dated Mar. 30, 2007.

European Search Report for EP 06739075.7, dated Sep. 13, 2011.

Surget et al.: 'Involvement of Vasopressin in Affective Disorders' European Journal Pharmacology vol. 583, 2008, pp. 340-349, XP022532879.

De Kloet et al: "Elevated plasma arginine vasopressin levels in veterans with posttraumatic stress disorder", Journal of Psychiatric Research, Elsevier Ltd, GB, vol. 42, No. 3, Dec. 20, 2007 (Dec. 20, 2007), pp. 192-198, XP022395299, ISSN: 0022-3956.

Ferris C F et al: "Orally active vasopressin V1a receptor antagonist, SRX251, selectively blocks aggressive behavior", Pharmacology Biochemistry and Behavior, Elsevier, US, vol. 83, No. 2, Feb. 1, 2006 (Feb. 1, 2006), pp. 169-174, XP027929666, ISSN: 0091-3057 [retrieved on Feb. 1, 2006].

Guillon et al: "Azetidinones as vasopressin V1a antagonists", Bioorganic & Medicinal Chemistry, Pergamon, GB, vol. 15, No. 5, Jan. 31, 2007 (Jan. 31, 2007), pp. 2054-2080, XP005867173, ISSN: 0968-0896, DOI: 10.1016/J.BMC.2006.12.031.

PCT International Search Report for PCT/USO4/32401 competed by the U.S. Searching Authority on Mar. 2, 2005.

Hirai, Koichi, et al. "An Example of the B-Lactam Ring Formation and Pyrrolinoazetidinone Ring Construction," Chemical Research Laboratories, vol. 37, pp. 133-139, 1985.

Office Action for U.S. Appl. No. 10/492,323 dated Nov. 9, 2005, 13 pages.

Office Action for U.S. Appl. No. 11/835,017 dated Apr. 16, 2008, 5 pages.

Office Action for U.S. Appl. No. 10/492,323 dated Mar. 7, 2005, 16 pages.

STNweb20100331X225934.

Thibonnier, M., et al. "The basic and clinical pharmacology of nonpeptide vasopressin receptor antagonists." Annual review of pharmacology and toxicology 41.1 (2001): 175-202.

(56) References Cited

OTHER PUBLICATIONS

Stromberg et al. (Acta Obstetricia et Gynecologica Scandinavica, 63, 6, 533-38), 1984.
Bhatia, Subhash C., and Shashi K. Bhatia. "Diagnosis and treatment of premenstrual dysphoric disorder." Am Fam Physician 66.7 (2002): 1239-1249.
Office Action for U.S. Appl. No. 11/442,788 dated Nov. 2, 2006, 16 pages.
PCT International Search Report for PCT/US2006/10192, dated Jul. 1, 2008.
Ojima, Iwao, et al., "Asymmetric Alkylation of Chiral (.beta.-Lactam Ester Enolates. A New Approach to the Synthesis of .alpha.-Alkylated alpha.-Amino Acids" 1987, J. Am. Chem. Soc., Chem. Comm., pp. 6537-6540.
Ring, Robert H. "The central vasopressinergic system: examining the opportunities for psychiatric drug development." Current pharmaceutical design 11.2 (2005): 205-225.
Simon, N.G. et al., "Novel vasopressin Ia anta1,>onists for CNS disorders: Development and characterization of clinical candidates", Neuroscience 2011, 1-2.
Fabio, Karine, et al. "Vasopressin antagonists as anxiolytics and antidepressants: Recent developments." Frontiers CNS Drug Discov 1.1 (2010): 156-183.
European Search Report for EP 15769990, dated Oct. 18, 2011.
Lee, Royce J., et al. "A novel V1a receptor antagonist blocks vasopressin-induced changes in the CNS response to emotional stimuli: an fMRI study." Frontiers in systems neuroscience 7 (2013).
Fabio, Karine, et al. "Synthesis and evaluation of potent and selective human V1a receptor antagonists as potential ligands for PET or SPECT imaging." Bioorganic & medicinal chemistry 20.3 (2012): 1337-1345.

\* cited by examiner

COMPOSITIONS AND METHODS FOR TREATING NEURODEGENERATIVE DISEASES

CROSS-REFERENCE TO RELATED APPLICATION

This application is a continuation of U.S. patent application Ser. No. 15/129,190, filed Sep. 26, 2016, now U.S. Pat. No. 9,802,925 issued Oct. 31, 2017, which is a U.S. national application under 37 C.F.R. § 371(b) of International Application Serial No. PCT/US15/23060 filed Mar. 27, 2015, which claims the priority under 35 U.S.C. § 119(e) to U.S. Provisional Application No. 61/971,862, filed on Mar. 28, 2014, the entire disclosures of each of which are incorporated herein by reference.

GOVERNMENT RIGHTS

This invention was made with government support under R44MH063663 awarded by the National Institute of Mental Health. The government has certain rights in the invention.

TECHNICAL FIELD

The invention described herein pertains to compounds, and compositions, methods, and uses thereof, for treating neurodegenerative diseases and disorders. In particular, the invention described herein pertains to vasopressin receptor modulators, and compositions, methods, and uses thereof, for treating neuropsychiatric aspects of neurodegenerative diseases such as Huntington's Disease, Parkinson's Disease, and Alzheimer's Disease.

BACKGROUND AND SUMMARY OF THE INVENTION

Neurodegenerative disorders (NDs) and diseases often have in common a neurodegenerative component that leads both to movement disorders, such as ballism, ataxia, hyperkinesis, Parkinsonims, athetosis, chorea, dyskinesias, and the like, as well as neuropsychiatric symptoms. In particular, Huntington's Disease (HD), Parkinson's Disease (PD), Alzheimer's Disease (AD) each present a constellation of symptoms. For example, HD, PD, and/or AD each may present symptoms including movement disorders or dysfunctions, as well as neuropsychiatric disorders, such as aggression, irritability, and anger. Though certain movement disorders, such as chorea, may be treated with drugs approved for certain neurodegenerative diseases, such as HD and PD, the neuropsychiatric aspects of neurodegenerative diseases are left untreated because traditional medications have not proved to be effective. Left untreated, such neuropsychiatric symptoms may lead to a wide range of complex, comorbid, and often unrelated downstream consequences. Accordingly, there is a current need for compounds, compositions, and methods for treating the neuropsychiatric aspects of neurodegenerative disorders and diseases.

HD is an inherited disease that results from expansion of a trinucleotide (CAG, cytosine/adenine/guanine) repeat that encodes a polyglutamine tract in the huntingtin protein. Onset is typically between 35 and 44 years of age, but it may begin much earlier or later. Symptoms include declines in behavioral, cognitive, and motor function. Psychiatric symptoms, including irritability and aggression, are common in HD patients and are among the most distressing aspects of the disease. For 40% to 70% of HD patients, irritability and aggression adversely affect daily life and often result in institutionalization (van Duijn et al., Psychopathology in verified Huntington's disease gene carriers. J Neuropsychiatry Clin Neurosci. 19:441-8 (2007)). Despite the frequent occurrence and severe consequences of irritability and aggressive behavior in HD, these symptoms have received little attention. Various assessment tools have been used to measure irritability in HD, including the Neuropsychiatric Inventory (NPI), the Unified Huntington Disease Rating Scale, the Irritability Scale (Chatterjee), and the Problem Behaviors Assessment for Huntington's Disease (PBA-HD). Nonetheless, blinded treatment studies in HD or long term follow-up studies of drug therapies for the neuropsychiatric aspects of HD, such as irritability and aggression, have not been conducted.

It has also been reported that currently available medications that have been observed to be effective in treating aggression, irritability, and anger, and/or depression and anxiety in other diseases, such as major depressive disorder and generalized anxiety disorder, either fail or are only transiently effective in treating the neuropsychiatric symptoms of HD, PD, and/or AD. For example, it has been reported that treatment with the antidepressant venlaxafine XR in HD patients improved depressive symptoms but led to increased irritability. Similarly, in AD patients, treatment with the antipsychotic risperidone only transiently reduced aggression, and was ineffective after 12 weeks. Similarly, aripiprazole also only provided transient effects. Moreover, recent government guidance has cautioned against using antipsychotics in elderly patients to treat dementia due to the observation of serious side effects and the general health risks associated with those drugs, including extrapyramidal symptoms, accelerated cognitive decline, stroke, and death. Therefore, those drugs are not considered a good choice for clinical use in treating neurodegenerative diseases, and it is specifically recommended that they are only used for short-term treatment (see, Ballard & Corbett, CNS Drugs 24(9): 729-739 (2010)).

Those treatment failures also suggest that the nature of the neuropsychiatric symptoms are distinct HD, AD, and PD. Stated another way, irritability, anger, aggression, depression, and anxiety in HD, AD, and PD are not the same as those apparently same behavioral endpoints in other diseases, such as paranoid schizophrenia, epilepsy, major depressive disorder, and the like, that can be treated effectively with drugs that are currently available. Without being bound by theory, it is believed herein that the outward manifestations of the neuropsychiatric aspects associated with HD, PD, and/or AD, such as aggression, irritability, and anger have a distinct underlying cause. Therefore, aggression, irritability, and anger, and depression and anxiety arising in patients suffering from HD, PD, and/or AD, is a separate disorder or dysfunction, and unrelated to aggression, irritability, and anger in other diseases. Further support for that conclusion arises from reports that, for example, irritability may be seen in a number of diseases and disorders, yet the underlying cause or dysfunction that manifests as irritability can be different in each case. Examples of such disorders include MOA-A deficiency, traumatic brain injury, stroke, mental retardation, major depressive disorder, bipolar disorder, and the like, each of which manifest in irritability or aggressive behavior. In particular, it has been reported that excessive signaling through vasopressin V1b receptors is responsible for various neuropsychiatric symptoms, inducing stress-related disorders, anxiety, depression, memory dysfunction, aggression, and social behavior (see, Ślusarz, "Vasopressin V1a and V1b receptor modulators: a patent review (2012-2014)" Expert Opinion Ther. Patents (2015)). Therefore, without being bound by theory, it is also believed herein that the reported treatment failures may arise from targeting the incorrect underlying causes of the neuropsychiatric symptoms specific to HD, AD, and/or PD. The treatment of the neuropsychiatric symptoms of HD/AD/PD, such as aggression, irritability, anger, depression, and anxiety is an unmet medical need.

It has been surprisingly discovered herein that altering vasopressin signaling in the central nervous system (CNS) is efficacious in treating the neuropsychiatric aspects, sometimes termed Behavioral and Psychological Symptoms in Dementia (BPSD), in neurodegenerative disorders and diseases, including, but not limited to HD, AD, and/or PD. In particular, it has surprisingly been discovered herein that neurodegenerative disorders and diseases, including but not limited HD, PD, and AD, and in particular the neuropsychiatric aspects thereof, may be treated by administering vasopressin antagonists that achieve therapeutically effective concentrations in the CNS. It has also been surprisingly discovered herein that compounds and compositions described herein show CNS effects after oral administration, and modulate specific brain circuits involved in responses to stimuli that result in irritability and aggression, and other neuropsychiatric aspects of ND in HD, AD, and PD patients.

Interestingly, there is no evidence that elevated arginine vasopressin (AVP) levels are present in the CNS of patients with HD, PD, and/or AD. In addition, elevated arginine vasopressin receptor (AVPR) expression levels in the CNS are not observed in patients with HD, PD, and/or AD. Given that neurodegeneration is one of the hallmarks of HD, PD, and AD, a pathology that includes the destruction of, or compromising of tissues in the brain that control executive functions might be expected. For example, the neuropsychiatric symptoms specific to HD, PD, and AD may arise from destruction of the brain tissues that are responsible for controlling executive functions. However, the opposite has been discovered herein regarding AVPR expression levels, which are otherwise similar to expression levels in those not suffering from HD, PD, or AD. Therefore, from a pathophysiological perspective, host animals suffering from HD, PD, and/or AD cannot be distinguished from normal cohorts on that basis. Nonetheless, though without being bound by theory, it is believed herein that the neuropsychiatric aspects of neurodegenerative disorders and diseases such as HD, PD, and/or AD may result from a condition-dependent excessive vasopressin signaling or an increase in vasopressin signaling, though not due to elevated AVP levels or overexpression of AVPR compared to non-diseased individuals. Instead, it is believed herein that the neuropsychiatric aspects of diseases such as HD, PD, and/or AD are due to condition-dependent AVP hypersensitivity in the CNS. Accordingly, apparently otherwise normal AVP levels nonetheless cause excessive vasopressin signaling in host animals with HD, PD, and/or AD. Without being bound by theory, it is also believed herein that the efficacy of the compounds, compositions, and methods described herein is due at least in part to modulating, correcting, or even preventing excessive vasopressin signaling even in the absence of excessive AVP concentrations or AVP expression in the CNS. In addition, though without being bound by theory, it is believed herein that the excessive vasopressin signaling that arises from AVP hypersensitivity leads to a dysfunction of or a loss of executive control function. That dysfunction or loss of function leads to a loss in the ability to appropriately control situationally dependent inappropriate behavior, such as aggression, irritability, and anger, and/or to make situationally dependent appropriate decisions, especially under stress or anxiety.

These surprising discoveries and the invention described herein are related to the treatment of what might otherwise be considered normal vasopressin signaling, where in the diseased host animal other inhibitory or corrective systems are ineffective or cannot accommodate the condition-dependent excessive vasopressin signaling. Thus, administration of the compounds or compositions described herein decreases vasopressin signaling to a level lower than would otherwise be considered as normal, bringing the dysregulated signaling systems, including those that control executive functions, back into balance.

In one illustrative embodiment of the invention, selective V1a vasopressin antagonists, and compositions and methods for using such vasopressin antagonists, are described herein. In another illustrative embodiment, selective V1a vasopressin antagonists, and compositions and methods for using such vasopressin antagonists, that are configured to achieve or capable of generating CNS concentrations of at least about 100 nM upon administration to a host animal are described herein. In another illustrative embodiment, selective V1a vasopressin antagonists, and compositions and methods for using such vasopressin antagonists, that are configured to achieve or capable of generating CNS concentrations of at least about 10 nM, or at least about 1 nM upon administration to a host animal are described herein. In another illustrative embodiment, selective V1a vasopressin antagonists, and compositions and methods for using such vasopressin antagonists, that are configured to achieve or capable of generating CNS concentrations of at least about 100 pM, at least about 10 pM, or at least about 1 pM, upon administration to a host animal are described herein.

It is appreciated herein that the neuropsychiatric aspects of neurodegenerative diseases such as HD, PD, and/or AD may present in advance of chorea, or other movement disorders. Accordingly, if diagnosed early in disease progression, the compounds, compositions, and methods described herein may also be effective in delaying the onset of movement disorders and other later stage symptoms or aspects of neurodegenerative diseases. Also described herein are compounds, compositions, and methods for the prophylactic treatment of neurodegenerative diseases such as HD, PD, and/or AD, such as the prophylactic treatment of movement disorders and dysfunctions and other later stage symptoms.

It has been discovered herein that neurodegenerative disorders and diseases such as HD, PD, and AD, and in particular the neuropsychiatric aspects thereof, are treatable with selective vasopressin V1a antagonists. In one embodiment, the vasopressin receptor antagonists are of the formula

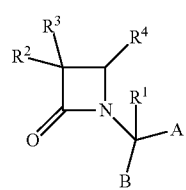

and pharmaceutically acceptable salts thereof; wherein
A is a carboxylic acid, an ester, or an amide;
B is a carboxylic acid, an ester, or an amide; or B is an alcohol or thiol, or a derivative thereof;

$R^1$ is hydrogen or $C_1$-$C_6$ alkyl;

$R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form a heterocyclyl group; and where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);

$R^3$ is an amino, amido, acylamido, or ureido group, which is optionally substituted; or $R^3$ is a nitrogen-containing heterocyclyl group attached at a nitrogen atom; and $R^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl.

In another embodiment, pharmaceutical compositions containing one or more of the compounds are also described herein. In one aspect, the compositions include a therapeutically effective amount of the one or more compounds for treating a host animal with a neurodegenerative disease. It is to be understood that the compositions may include other components and/or ingredients, including, but not limited to, other therapeutically active compounds, and/or one or more carriers, diluents, excipients, and the like, and combinations thereof. In another embodiment, methods for using the compounds and pharmaceutical compositions for treating host animals with a neurodegenerative disease are also described herein. In one aspect, the methods include the step of administering one or more of the compounds and/or compositions described herein to the host animal. In another aspect, the methods include administering a therapeutically effective amount of the one or more compounds and/or compositions described herein for treating host animals a neurodegenerative disease. In another embodiment, uses of the compounds and compositions in the manufacture of a medicament for treating host animals with a neurodegenerative disease are also described herein. In one aspect, the medicaments include a therapeutically effective amount of the one or more compounds and/or compositions described herein.

It is to be understood herein that the compounds described herein may be used alone or in combination with other compounds useful for treating neurodegenerative diseases, including those compounds that may be therapeutically effective by the same or different modes of action. In addition, it is to be understood herein that the compounds described herein may be used in combination with other compounds that are administered to treat other symptoms of a neurodegenerative disease, such as compounds administered to treat chorea or other movement disorders, and the like.

DETAILED DESCRIPTION

Figure 1:
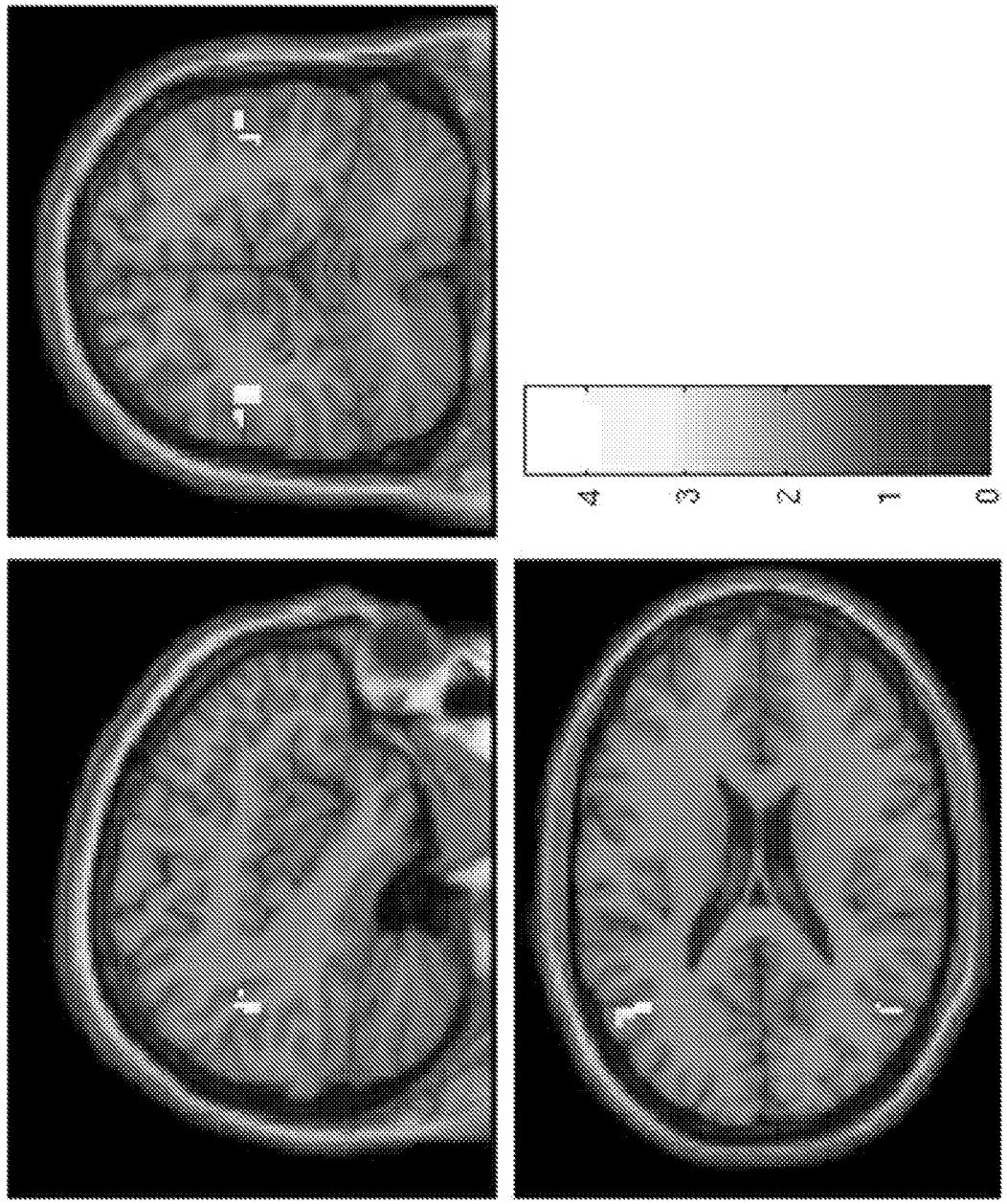
FIG. 1 shows a high resolution structural template of the decrease in BOLD signal in the temporoparietal cortex (Brodmann Area 39).

Described herein is the use of one or more vasopressin V1a recepor antagonists as a therapeutic approach for treating neurodegenerative diseases. The compounds described herein may have the potential to greatly improve the lives of those suffering from neurodegenerative diseases, such as AD, PD, and HD. The debeilitating nature of and mortality associated with neurodegenerative diseases, such as AD, PD, and HD is not only due to the movement disorders and dysfunction that accompany neurodegenerative diseases, but also due to the neuropsychiatric disorders, such as uncontrollable or inappropriate aggression, anger, irritability, and related symptoms.

Several illustrative embodiments of the invention are described by the following illustrative clauses:

A method for treating a neurodegenerative disease or disorder, such as HD, AD, or PD, in a host animal, the method comprising the step of administering a composition comprising one or more selective vasopressin V1a receptor antagonists to the host animal.

A method for treating the neuropsychiatric aspects of a neurodegenerative disease or disorder, such as HD, AD, or PD, in a host animal, the method comprising the step of administering one or more selective vasopressin V1a receptor antagonists to the host animal.

The method of any one of the preceding clauses wherein the neuropsychiatric aspects include aggression.

The method of any one of the preceding clauses wherein the neuropsychiatric aspects include irritability.

The method of any one of the preceding clauses wherein the neuropsychiatric aspects include anger.

The method of any one of the preceding clauses wherein the method results in improved scores in Aberrant Behavior Checklist (ABCi), Cohen-Mansfield Aggression Inventory (CMAI), Problem Behaviors Assessment short form (PBA-s), and/or Irritability Scale (IS).

The method of any one of the preceding clauses wherein one or more of the antagonists are selected from compounds of the formula:

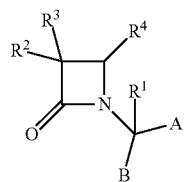

and pharmaceutically acceptable salts thereof, wherein

A is a carboxylic acid, an ester, or an amide;

B is a carboxylic acid, an ester, or an amide; or B is an alcohol or thiol, or a derivative thereof;

$R^1$ is hydrogen or $C_1$-$C_6$ alkyl;

$R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form a heterocyclyl group; and where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);

$R^3$ is an amino, amido, acylamido, or ureido group, which is optionally substituted; or $R^3$ is a nitrogen-containing heterocyclyl group attached at a nitrogen atom; and $R^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl.

The method of any one of the preceding clauses wherein one or more of the antagonists are selected from compounds of the formula:

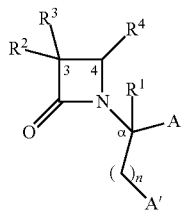

(I)

and pharmaceutically acceptable salts thereof, wherein
A and A' are each independently selected from —$CO_2H$, or an ester or amide derivative thereof;
n is an integer selected from 0 to about 3;
$R^1$ is hydrogen or $C_1$-$C_6$ alkyl;
$R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form an heterocycle; and where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);

$R^3$ is an amino, amido, acylamido, or ureido group, which is optionally substituted; or $R^3$ is a nitrogen-containing heterocyclyl group attached at a nitrogen atom; and $R^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl.

The method of any one of the preceding clauses wherein one or more of the antagonists are selected from compounds of the formula:

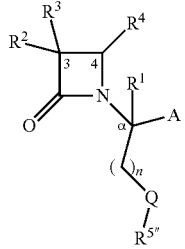

(II)

and pharmaceutically acceptable salts thereof, wherein
A is —$CO_2H$ or an ester or amide derivative thereof;
Q is oxygen; or Q is sulfur or disulfide, or an oxidized derivative thereof;
n is an integer from 1 to 3;
$R^1$, $R^2$, $R^3$, and $R^4$ are as defined in formula I; and
$R^{5''}$ is selected from hydrogen, alkyl, cycloalkyl, alkoxyalkyl, optionally substituted arylalkyl, optionally substituted heterocyclyl or optionally substituted heterocyclylalkyl, and optionally substituted aminoalkyl.

The method of any one of the preceding clauses wherein A is —$CO_2R^5$; where $R^5$ is selected from hydrogen, alkyl, cycloalkyl, alkoxyalkyl, optionally substituted arylalkyl, heterocyclyl, heterocyclyl($C_1$-$C_4$ alkyl), and $R^6R^7N$—($C_2$-$C_4$ alkyl).

The method of any one of the preceding clauses wherein A is monosubstituted amido, disubstituted amido, or an optionally substituted nitrogen-containing heterocyclylamido.

The method of any one of the preceding clauses wherein heterocyclyl is independently selected from tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally substituted aryl($C_1$-$C_4$ alkyl). It is to be understood that in each occurrence of the various embodiments described herein, heterocyclyl is independently selected in each instance.

The method of any one of the preceding clauses wherein $R^6$ is independently selected from hydrogen or alkyl; and $R^7$ is independently selected in each instance from alkyl, cycloalkyl, optionally substituted aryl, or optionally substituted arylalkyl. The method of any one of the preceding clauses wherein $R^6$ and $R^7$ are taken together with the attached nitrogen atom to form an optionally substituted heterocycle, such as pyrrolidinyl, piperidinyl, morpholinyl, piperazinyl, and homopiperazinyl; where said piperazinyl or homopiperazinyl is also optionally N-substituted with $R^{13}$; where $R^{13}$ is independently selected in each instance from hydrogen, alkyl, cycloalkyl, alkoxycarbonyl, optionally substituted aryloxycarbonyl, optionally substituted arylalkyl, and optionally substituted aryloyl. It is also to be understood that in each occurrence of the various embodiments described herein, $R^6$ and $R^7$ are each independently selected in each instance.

The method of any one of the preceding clauses wherein A and/or A' is an amide. The method of any one of the preceding clauses wherein both A and A' are amides. The method of any one of the preceding clauses wherein A and/or A' is an amide of a secondary amine, also refered to herein as a secondary amide. The method of any one of the preceding clauses wherein both A and A' are secondary amides. It is to be understood that secondary amides include amides of cyclic amines attached at nitrogen.

The method of any one of the preceding clauses wherein A is an amide. The method of any one of the preceding clauses wherein A is an amide of a secondary amine, also refered to herein as a secondary amide.

The method of any one of the preceding clauses wherein the antagonists are diesters, acid-esters, or diacids, including pharmaceutically acceptable salts thereof, where each of A and A' is independently selected. The method of any one of the preceding clauses wherein the antagonists are ester-amides, where one of A and A' is an ester, and the other is an amide. The method of any one of the preceding clauses wherein the antagonists are diamides, where each of A and A' are independently selected from monosubstituted amido, disubstituted amido, and optionally substituted nitrogen-containing heterocyclylamido.

The method of any one of the preceding clauses wherein A and/or A' is an independently selected monosubstituted amido of the formula C(O)NHX—, where X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N$—, and $R^6R^7N$—($C_2$-$C_4$ alkyl), where each heterocyclyl is independently selected.

The method of any one of the preceding clauses wherein A and/or A' is an independently selected disubstituted amido of the formula C(O)NR$^{14}$X—, where R$^{14}$ is selected from hydroxy, alkyl, alkoxycarbonyl, and benzyl; and X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N$—, and $R^6R^7N$—($C_2$-$C_4$ alkyl), where each heterocyclyl is independently selected.

The method of any one of the preceding clauses wherein A and/or A' is an amide of an independently selected optionally substituted nitrogen-containing heterocycle attached at a nitrogen. Illustrative nitrogen-containing heterocycles include but are not limited to pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl; each of which is optionally substituted. Such optional substitutions include the groups $R^{10}$, $R^{12}$, $R^6R^7N$—, and $R^6R^7N$—($C_1$-$C_4$ alkyl), as defined herein.

The method of any one of the preceding clauses wherein A and/or A' is independently selected from pyrrolidinonyl, piperidinonyl, 2-(pyrrolidin-1-ylmethyl)pyrrolidin-1-yl, or 1,2,3,4-tetrahydroisoquinolin-2-yl, each of which is optionally substituted, and attached at a nitrogen.

The method of any one of the preceding clauses wherein A and/or A' is an independently selected amide of an optionally substituted piperidinyl attached at the nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl).

The method of any one of the preceding clauses wherein A and/or A' is an independently selected piperidinyl substituted at the 4-position and attached at the nitrogen.

The method of any one of the preceding clauses wherein A and/or A' is an independently selected amide of an optionally substituted piperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl).

The method of any one of the preceding clauses wherein A and/or A' is an independently selected piperazinyl substituted at the 4-position and attached at a nitrogen.

The method of any one of the preceding clauses wherein A and/or A' is an independently selected amide of an optionally substituted homopiperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). The method of any one of the preceding clauses wherein A and/or A' is an independently selected homopiperazinyl substituted at the 4-position and attached at a nitrogen. The method of any one of the preceding clauses wherein A and/or A' is an independently selected homopiperazinyl substituted at the 4-position with alkyl, aryl, aryl ($C_1$-$C_4$ alkyl), and attached at a nitrogen.

The method of any one of the preceding clauses wherein A' is monosubstituted amido, disubstituted amido, or an optionally substituted nitrogen-containing heterocyclylamido. The method of any one of the preceding clauses wherein A' is —$CO_2R^{5'}$; where $R^{5'}$ is selected from hydrogen, alkyl, cycloalkyl, alkoxyalkyl, optionally substituted arylalkyl, heterocyclyl, heterocyclyl($C_1$-$C_4$ alkyl), and $R^6R^7N$—($C_2$-$C_4$ alkyl); where heterocyclyl is in each occurrence independently selected from tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally substituted aryl($C_1$-$C_4$ alkyl). The method of any one of the preceding clauses wherein $R^{5'}$ is optionally substituted heterocyclylalkyl or optionally substituted aminoalkyl, including $R^6R^7N$—($C_2$-$C_4$ alkyl).

The method of any one of the preceding clauses wherein A is of the formula

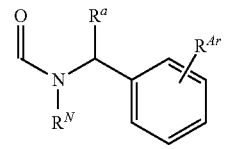

where $R^N$ is hydrogen or optionally substituted alkyl, or an amide prodrug forming group; $R^a$ is hydrogen or optionally substituted alkyl; and $R^{Ar}$ is hydrogen or one or more aryl substituents, such as but not limited to halo, hydroxy, optionally substituted alkyl, optionally substituted alkoxy, nitro, and the like. The method of any one of the preceding clauses wherein at least one of $R^N$, $R^a$, and $R^{Ar}$ is not hydrogen. The method of any one of the preceding clauses wherein at least one of $R^N$ and $R^a$ is not hydrogen. In another embodiment, A is of the formula

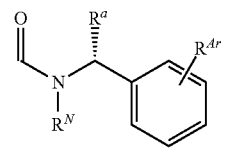

where $R^N$, $R^a$, and $R^{Ar}$ are as defined herein.

The method of any one of the preceding clauses wherein A is selected from monosubstituted amido, disubstituted amido, and optionally substituted nitrogen-containing heterocyclylamido. The method of any one of the preceding clauses wherein A is an amide of optionally substituted 1-tetrahydronaphthylamine.

The method of any one of the preceding clauses wherein A and/or A' is a monosubstituted amido of the formula C(O)NHX, where X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N$—, and $R^6R^7N$—($C_2$-$C_4$ alkyl), where each heterocyclyl is independently selected.

The method of any one of the preceding clauses wherein A and/or A' is a disubstituted amido of the formula C(O)NR$^{14}$X, where $R^{14}$ is selected from hydroxy, alkyl, alkoxycarbonyl, and benzyl; and X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N$—, and $R^6R^7N$—($C_2$-$C_4$ alkyl), where each heterocyclyl is independently selected.

The method of any one of the preceding clauses wherein A and/or A' is an amide of an optionally substituted nitrogen-containing heterocycle attached at a nitrogen. Illustrative nitrogen-containing heterocycles include but are not limited to pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl; each of which is optionally substituted. Such optional substitutions include the groups $R^{10}$, $R^{12}$, $R^6R^7N$—, and $R^6R^7N$—($C_1$-$C_4$ alkyl), as defined herein. The method of any one of the preceding clauses wherein A is pyrrolidinonyl, piperidinonyl, 2-(pyrrolidin-1-ylmethyl)pyrrolidin-1-yl, or 1,2,3,4-tetrahydroisoquinolin-2-yl, each of which is optionally substituted, and attached at a nitrogen.

The method of any one of the preceding clauses wherein A and/or A' is an amide of an optionally substituted piperidinyl attached at the nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). The method of any one of the preceding clauses wherein A and/or A' is piperidinyl substituted at the 4-position and attached at the nitrogen.

The method of any one of the preceding clauses wherein A and/or A' is an amide of an optionally substituted piperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). The method of any one of the preceding clauses wherein A and/or A' is piperazinyl substituted at the 4-position and attached at a nitrogen.

The method of any one of the preceding clauses wherein A and/or A' is an amide of an optionally substituted homopiperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). The method of any one of the preceding clauses wherein A and/or A' is homopiperazinyl substituted at the 4-position and attached at a nitrogen. The method of any one of the preceding clauses wherein A and/or A' is homopiperazinyl substituted at the 4-position with alkyl, aryl, aryl($C_1$-$C_4$ alkyl), and attached at a nitrogen.

The method of any one of the preceding clauses wherein A and/or A' is an amide of a heterocycle attached at a nitrogen, where the heterocycle is substituted with heterocyclyl, heterocyclylalkyl, cycloalkyl, cycloalkylalkyl, aryl, arylalkyl.

The method of any one of the preceding clauses wherein A and/or A' is an amide of an optionally substituted benzyl, optionally substituted 1-naphthylmethyl, or optionally substituted 2-naphthylmethyl amine. Optional substitutions include, but are not limited to, 2,3-dichloro, 2,5-dichloro, 2,5-dimethoxy, 2-trifluoromethyl, 2-fluoro-3-trifluoromethyl, 2-fluoro-5-trifluoromethyl, 2-methyl, 2-methoxy, 3,4-dichloro, 3,5-ditrifluoromethyl, 3,5-dichloro, 3,5-dimethyl, 3,5-difluoro, 3,5-dimethoxy, 3-bromo, 3-trifluoromethyl, 3-chloro-4-fluoro, 3-chloro, 3-fluoro-5-trifluoromethyl, 3-fluoro, 3-methyl, 3-nitro, 3-trifluoromethoxy, 3-methoxy, 3-phenyl, 4-trifluoromethyl, 4-chloro-3-trifluoromethyl, 4-fluoro-3-trifluoromethyl, 4-methyl, and the like.

The method of any one of the preceding clauses wherein A and/or A' is an amide of an optionally substituted benzyl-N-methylamine. In another embodiment, A in formula (I) or (II) is an amide of an optionally substituted benzyl-N-butylamine, including n-butyl, and t-butyl. The method of any one of the preceding clauses wherein A is an amide of an optionally substituted benzyl-N-benzylamine. Optional substitutions include, but are not limited to, 2,3-dichloro, 3,5-dichloro, 3-bromo, 3-trifluoromethyl, 3-chloro, 3-methyl, and the like.

The method of any one of the preceding clauses wherein A and/or A' is an amide of an optionally substituted 1-phenylethyl, 2-phenylethyl, 2-phenylpropyl, or 1-phenylbenzylamine. The method of any one of the preceding clauses wherein A and/or A' is an amide of an optionally substituted 1-phenylethyl, 2-phenylethyl, 2-phenylpropyl, 1-phenylbenzylamine-N-methylamine. The method of any one of the preceding clauses wherein A and/or A' is an amide of an optionally substituted 2-phenyl-β-alanine, or derivative thereof, 1-phenylpropanolamine, and the like. Optional substitutions include, but are not limited to, 3-trifluoromethoxy, 3-methoxy, 3,5-dimethoxy, 2-methyl, and the like.

The method of any one of the preceding clauses wherein A and/or A' is an amide of an optionally substituted 1-phenylcyclopropyl, 1-phenylcyclopentyl, or 1-phenylcyclohexylamine. Optional substitutions include, but are not limited to, 3-fluoro, 4-methoxy, 4-methyl, 4-chloro, 2-fluoro, and the like.

The method of any one of the preceding clauses wherein A and/or A' is an amide of an optionally substituted heteroarylmethylamine, including but not limited to 2-furyl, 2-thienyl, 2-pyridyl, 3-pyridyl, 4-pyridyl, and the like. Optional substitutions include, but are not limited to, 5-methyl, 3-chloro, 2-methyl, and the like.

The method of any one of the preceding clauses wherein A and/or A' is an amide of a partially saturated bicyclic aryl, including but not limited to 1-, 2-, 4-, and 5-indanylamine, 1- and 2-tetrahydronaphthylamine, indolinyl, tetrahydroquinolinyl, tetrahydroisoquinolinyl, and the like, each of which is optionally substituted.

The method of any one of the preceding clauses wherein A and/or A' is an amide of a substituted piperidine or piperazine. Substituents on the piperidine or piperazine include heterocyclyl, heterocyclylalkyl, optionally substituted aryl, and optionally substituted arylalkyl. Illustrative piperidines and piperazines include the formulae:

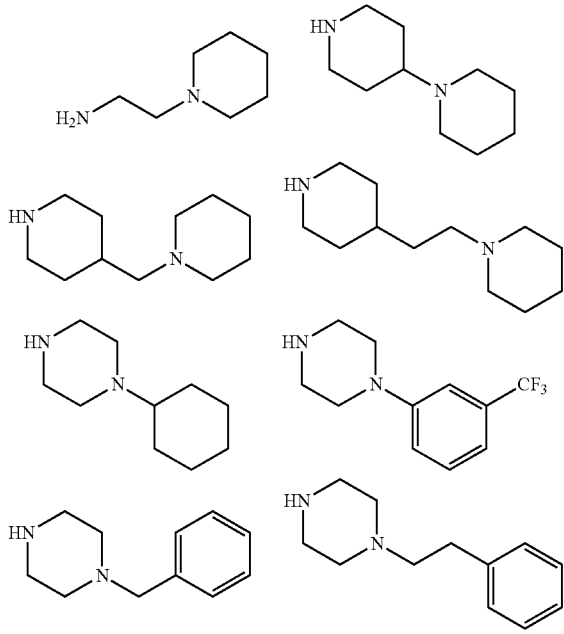

The method of any one of the preceding clauses wherein A' is an amide of a substituted heterocycle attached at nitrogen. Substituents include alkyl, cycloalkyl, cycloalkylalkyl, heterocyclyl, heterocyclylalkyl, aryl, and arylalkyl. The method of any one of the preceding clauses wherein A' is an amide of a heterocycle attached at nitrogen substituented with alkyl, cycloalkyl, cycloalkylalkyl, heterocyclyl, or heterocyclylalkyl.

The method of any one of the preceding clauses wherein A' is an amide of an optionally substituted arylheterocyclylamine, arylalkylheterocyclylamine, heterocyclylalkylamine, or heteroarylalkylamine. The method of any one of the preceding clauses wherein A' is an amide of piperidin-1-ylpiperidine or piperidin-1-ylalkylpiperidine. In another embodiment, alkyl is $C_1$-$C_2$-alkyl.

The method of any one of the preceding clauses wherein Q is oxygen or sulfur. The method of any one of the preceding clauses wherein R" is optionally substituted arylalkyl. The method of any one of the preceding clauses wherein A is an amide of a substituted piperidine or piperazine.

The method of any one of the preceding clauses wherein n is 1 or 2. The method of any one of the preceding clauses wherein n is 1.

The method of any one of the preceding clauses wherein $R^2$ is hydrogen, alkyl, alkoxy, alkylthio, cyano, formyl, alkylcarbonyl, or a substituent selected from the group consisting of —$CO_2R^8$ and —$CONR^8R^{8'}$, where $R^8$ and $R^{8'}$ are each independently selected from hydrogen and alkyl. The method of any one of the preceding clauses wherein $R^2$ is hydrogen or alkyl. The method of any one of the preceding clauses wherein $R^2$ is hydrogen.

The method of any one of the preceding clauses wherein $R^1$ is hydrogen. The method of any one of the preceding clauses wherein $R^1$ is methyl. The method of any one of the preceding clauses wherein both $R^1$ and $R^2$ are hydrogen.

The method of any one of the preceding clauses wherein $R^3$ is of the formulae:

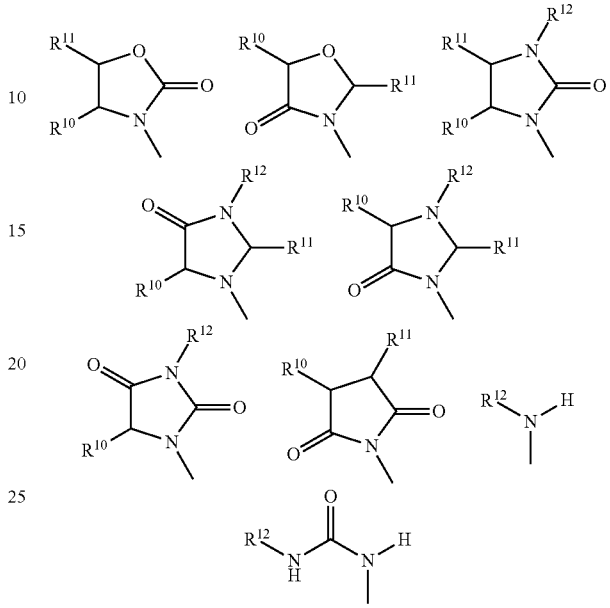

wherein $R^{10}$ and $R^{11}$ are each independently selected from hydrogen, optionally substituted alkyl, optionally substituted cycloalkyl, alkoxycarbonyl, alkylcarbonyloxy, optionally substituted aryl, optionally substituted arylalkyl, optionally substituted arylalkyloxy, optionally substituted arylalkylcarbonyloxy, diphenylmethoxy, triphenylmethoxy, and the like; and $R^{12}$ is selected from hydrogen, alkyl, cycloalkyl, alkoxycarbonyl, optionally substituted aryloxycarbonyl, optionally substituted arylalkyl, optionally substituted aryloyl, and the like.

The method of any one of the preceding clauses wherein $R^3$ is of the formulae:

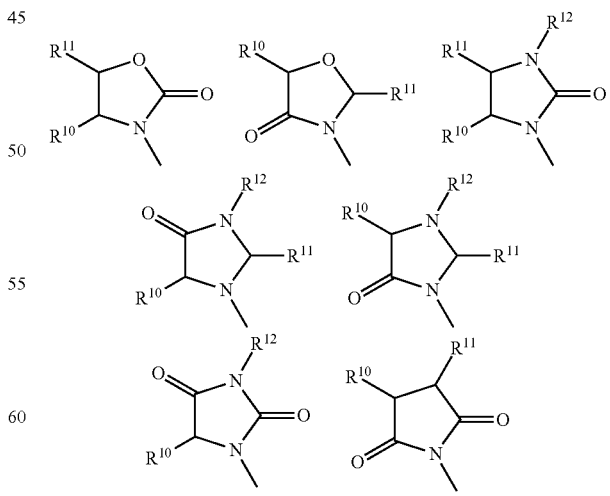

wherein $R^{10}$, $R^{11}$, and $R^{12}$ are as defined herein.

The method of any one of the preceding clauses wherein $R^3$ is of the formulae:

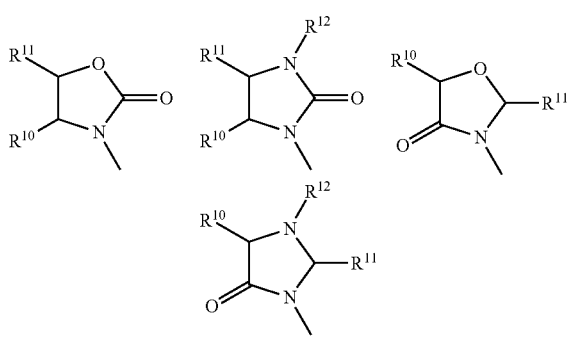

wherein $R^{10}$, $R^{11}$, and $R^{12}$ are as defined herein.

The method of any one of the preceding clauses wherein $R^3$ is of the formula:

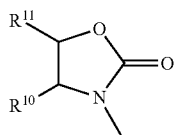

wherein $R^{10}$ and $R^{11}$ are as defined herein.

The method of any one of the preceding clauses wherein $R^4$ is of the formulae:

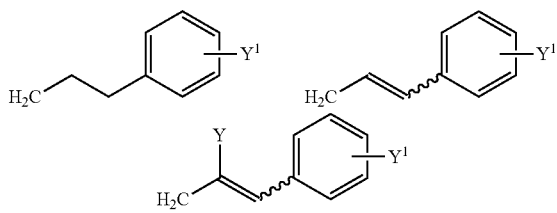

wherein Y an electron withdrawing group, such as halo, and $Y^1$ is hydrogen or one or more aryl substituents, such as but not limited to halo, hydroxy, amino, nitro, optionally substituted alkyl, optionally substituted alkoxy, and the like. It is to be understood that the double bond in the formulae may be all or substantially all (E), all or substantially all (Z), or a mixture thereof. The method of any one of the preceding clauses wherein the double bond in the formulae is all or substantially all (E). The method of any one of the preceding clauses wherein $R^4$ is of the formulae:

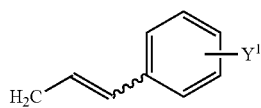

wherein $Y^1$ is as defined herein. In another embodiment, $Y^1$ is not hydrogen.

The method of any one of the preceding clauses wherein n is 1, the stereochemistry of the α-carbon is (S) or (R), or is an epimeric mixture. The method of any one of the preceding clauses wherein n is 1, the stereochemistry of the α-carbon is (R). The method of any one of the preceding clauses wherein n is 2, the stereochemistry of the α-carbon is (S). The method of any one of the preceding clauses wherein n is 1 and Q is oxygen, the stereochemistry of the α-carbon is (R). The method of any one of the preceding clauses wherein n is 1 and Q is sulfur, the stereochemistry of the α-carbon is (S). It is appreciated that the compounds of formulae (I) and (II) are chiral at the α-carbon, except when A=A', and n=0.

The method of any one of the preceding clauses wherein $R^{5"}$ is optionally substituted aryl($C_2$-$C_4$ alkyl). The method of any one of the preceding clauses wherein $R^{5"}$ is optionally substituted aryl($C_1$-$C_2$ alkyl). The method of any one of the preceding clauses wherein $R^{5"}$ is optionally substituted benzyl. The method of any one of the preceding clauses wherein $R^{5"}$ is optionally substituted alkyl.

The method of any one of the preceding clauses wherein at least one compound is SRX228 (Example 233).

The method of any one of the preceding clauses wherein at least one compound is SRX246 (Example 224).

The method of any one of the preceding clauses wherein at least one compound is SRX251 (Example 225).

The method of any one of the preceding clauses wherein at least one compound is SRX296 (Example 232E).

The method of any one of the preceding clauses wherein at least one compound is SRX576 (Example 266).

The method of any one of the preceding clauses wherein the administration step includes a total daily dose of about 160 to about 700 mg total of one or more compounds of any one of the foregoing clauses, in single or divided form.

The method of any one of the preceding clauses wherein the administration step includes a total daily dose of about 160 to about 500 mg total of one or more compounds of any one of the foregoing clauses, in single or divided form.

The method of any one of the preceding clauses wherein the administration step includes a total daily dose of about 160 to about 400 mg total of one or more compounds of any one of the foregoing clauses, in single or divided form.

The method of any one of the preceding clauses wherein the administration step includes a total daily dose of about 160 to about 320 mg total of one or more compounds of any one of the foregoing clauses, in single or divided form.

The method of any one of the preceding clauses wherein the administration step includes a total daily dose of about 160 to about 240 mg total of one or more compounds of any one of the foregoing clauses, in single or divided form.

The method of any one of the preceding clauses wherein the administration step includes a q.d. dosing protocol.

The method of any one of the preceding clauses wherein the administration step includes a b.i.d. dosing protocol.

The method of any one of the preceding clauses wherein the administration step includes an extended release dosing protocol.

A pharmaceutical composition adapted for or capable of treating a neurodegenerative disease or disorder, such as HD, AD, or PD, in a host animal, the composition comprising one or more compounds of any one of the foregoing clauses, and optionally, one or more carriers, diluents, or adjuvants, or a combination thereof.

A unit dose or unit dosage form adapted for or capable of treating a neurodegenerative disease or disorder, such as HD, AD, or PD, in a host animal, the composition comprising one or more compounds of any one of the foregoing clauses, and optionally, one or more carriers, diluents, or adjuvants, or a combination thereof.

The unit dose or unit dosage form of any one of the preceding clauses comprising about 80 to about 350 mg total of one or more compounds of any one of the foregoing clauses, in single or divided form.

The unit dose or unit dosage form of any one of the preceding clauses comprising about 80 to about 250 mg total of one or more compounds of any one of the foregoing clauses, in single or divided form.

The unit dose or unit dosage form of any one of the preceding clauses comprising about 80 to about 200 mg total of one or more compounds of any one of the foregoing clauses, in single or divided form.

The unit dose or unit dosage form of any one of the preceding clauses comprising about 80 to about 160 mg total of one or more compounds of any one of the foregoing clauses, in single or divided form.

The unit dose or unit dosage form of any one of the preceding clauses comprising about 80 to about 120 mg total of one or more compounds of any one of the foregoing clauses, in single or divided form.

The unit dose or unit dosage form of any one of the preceding clauses adapted for oral delivery.

The unit dose or unit dosage form of any one of the preceding clauses adapted for extended release.

It is to be understood that each of the foregoing clauses and in each of the embodiments described herein of formula (I), the various genera, subgenera, and species of each of A, A', Y, Y$^1$, n, R$^1$, R$^2$, R$^3$, R$^4$, R$^5$, and the like, may be combined without limitation, and therefore each such additional embodiment of the invention is thereby described by the combination. It is also to be understood that each of the foregoing clauses and in each of the embodiments described herein of formula (II), the various genera, subgenera, and species of each of A, Q, Y, Y$^1$, n, R$^1$, R$^2$, R$^3$, R$^4$, R$^5$, R$^{5\prime\prime\prime}$, and the like may be combined without limitation, and therefore each such additional embodiment of the invention is thereby described by the combination. For example, the method of any one of the preceding clauses wherein compounds of formula (I) are described where (a) A is of the formula

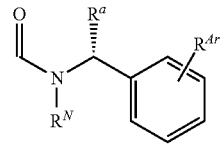

where R$^N$, R$^a$, and R$^{Ar}$ are as defined herein; and n is 1;

(b) n is 1, and R$^1$ is hydrogen;

(c) A is of the formula

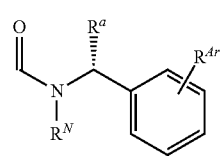

where R$^N$, R$^a$, and R$^{Ar}$ are as defined herein; n is 1; and R$^1$ is hydrogen;

(d) R$^1$ and R$^3$ are both hydrogen;

(e) R$^1$ and R$^2$ are both hydrogen; and R$^3$ is of the formula

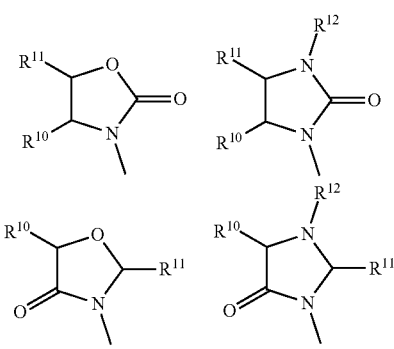

wherein R$^{10}$, R$^{11}$, and R$^{12}$ are as defined herein;

(f) A is of the formula

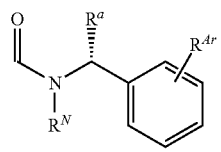

where R$^N$, R$^a$, and R$^{Ar}$ are as defined herein; n is 1; R$^1$ and R$^2$ are both hydrogen; and R$^3$ is of the formula

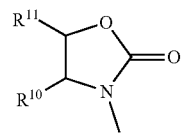

wherein R$^{10}$ and R$^{11}$ are as defined herein;

(g) A is of the formula

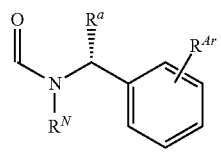

where R$^N$, R$^a$, and R$^{Ar}$ are as defined herein; n is 1; R$^1$ and R$^2$ are both hydrogen; and A' is of the formula

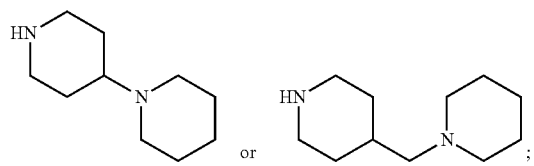 [SMILES: C1CCN(C2CCNCC2)CC1 ; C1CCN(CC2CCNCC2)CC1]

and the like.

It is appreciated that in the illustrative clauses and embodiments described herein, A and/or A' may include a chiral center, either of the optically pure enantiomers may be included in the compounds described herein; alternatively, the racemic form may be used. For example, either or both of the following enatiomers may be included in the compounds described herein (R)-1-(3-methoxyphenyl)ethylamine, (R)-1-(3-trifluoromethylphenyl)ethylamine, (R)-1,2,3,4-tetrahydro-1-naphtylamine, (R)-1-indanylamine, (R)-α,N-dimethylbenzylamine, (R)-α-methylbenzylamine, (S)-1-(3-methoxyphenyl)ethylamine, (S)-1-(3-trifluoromethylphenyl)ethylamine, (S)-1,2,3,4-tetrahydro-1-naphtylamine, (S)-1-indanylamine, and (S)-α-methylbenzylamine, and the like.

Without being bound by theory, it is believed herein that AVP and related peptides represent a family of chemical signals in vertebrates and serve an important function in the control of social behaviors and emotions. AVP is synthesized in neurons in the hypothalamus of all mammals. It is released from nerve endings in the median eminence and transported to the pituitary gland, where it enhances the release of adrenocorticotrophic hormone (ACTH) and ultimately the level of stress hormones in the circulation through its actions at pituitary AVP receptors. From nerve endings in the pituitary, AVP also enters the general blood stream where it acts on the heart and blood vessels to affect cardiac performance and on the kidneys to decrease urine volume. AVP neurons and nerve fibers also are found throughout the limbic system of the brain. AVP exerts its physiological and behavioral effects by binding to specific G-Protein Coupled Receptors (GPCRs) in the central nervous system and certain peripheral tissues/sites. Three distinct AVP receptor subtypes have been identified—V1a, V1b, and V2. V1a is the predominant AVP receptor found in the limbic system and cortex, V1b receptor is located in limbic system and pituitary gland, although it is less widespread than V1a. The V2 receptor is localized in kidney, where it mediates the antidiuretic effects of vasopressin. It is generally believed herein that V2 is not expressed in the nervous systems of adult animals or humans.

In another embodiment, compounds described herein are selectively active at the V1a AVP receptor. In another embodiment, compounds described herein are selectively active at the V1a AVP receptor, and are less active, substantially less active, and/or inactive at other AVP receptors, such as the V1b and/or V2 subtypes of AVP receptors. In another embodiment, compounds described herein are 10-fold selective for the V1a receptor compared to the V1b and/or V2 receptor. In another embodiment, compounds described herein are 100-fold selective for the V1a receptor compared to the V1b and/or V2 receptor. In another embodiment, compounds described herein are 1000-fold selective for the V1a receptor compared to the V1b and/or V2 receptor. In another embodiment, compounds described herein are 10,000-fold selective for the V1a receptor compared to the V1b and/or V2 receptor.

In another embodiment, compounds described herein cross the blood-brain-barrier (BBB) and show high CNS permeability. In another embodiment, compounds described herein show efficacious dose levels in the brain for treating neurodegenerative disorders. In another embodiment, compounds described herein exhibit plasma levels at or in excess of those necessary for clinical efficacy in treating neurodegenerative disorders. In another embodiment, compounds described herein exhibit pharmacokinetics consistent with twice per day (b.i.d.) dosing. In another embodiment, compounds described herein exhibit pharmacokinetics consistent with once per day (q.d.) dosing. It is appreciated herein that both b.i.d. and q.d. dosing may be an important feature in improving patient compliance, leading to overall enhanced clinical effectiveness. In another embodiment, compounds described herein are metabolically stable in stomach and blood. In another embodiment, compounds described herein exhibit cardiovascular safety profiles both in vivo and in vitro consistent with the treatment of neurodegenerative disorders. In another embodiment, compounds described herein exhibit respiratory safety in vivo.

In another embodiment, compounds described herein, and pharmaceutical compositions and medicaments containing them, exhibit high plasma levels and high brain levels, including with oral administration. In another embodiment, compounds described herein, and pharmaceutical compositions and medicaments containing them, capable of crossing the blood brain barrier (BBB), including with oral administration. In another embodiment, compounds described herein, and pharmaceutical compositions and medicaments containing them, exhibit high CNS bioavailability and high affinity without significant or competitive binding to other predetermined GPCRs, or other predetermined receptors, including but not limited to neurotransmitter related receptors, steroid receptors, ion channels, second messenger receptors, prostaglandin receptors, growth factor and hormone receptors, other brain and gastrointestinal tract peptide receptors, other enzymes, and the like. In one aspect, compounds described herein, and pharmaceutical compositions and medicaments containing them, are inactive or substantially inactive at 100 nM against a standard panel of 64 receptors including 35 GPCRs (Novascreen panel), including neurotransmitter related receptors, steroidal receptors, ion channels, second messenger receptors, prostaglandin receptors, growth factor receptors, hormonal receptors, brain/gut peptides (not including vasopressin 1), and enzymes.

In another embodiment, compounds described herein, and pharmaceutical compositions and medicaments containing them, have specific behavioral effects that are context dependent (see, for example, Ferris & Potegal Physiology and Behavior, 44:235-239 (1988)). For example, in another embodiment, compounds described herein, and pharmaceutical compositions and medicaments containing them are effective in modulating neuropsychiatric disorders, but have little or no effect on sexual behavior.

In each of the foregoing clauses and each of the embodiments described herein, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to be a description of such hydrates and/or solvates, including pharmaceutically acceptable solvates.

In each of the clauses and embodiments described herein, it is also to be understood that the formulae include and represent each possible isomer, such as stereoisomers and geometric isomers, both individually and in any and all possible mixtures. In each of the foregoing and each of the following embodiments, it is also to be understood that the formulae include and represent any and all crystalline forms, partially crystalline forms, and non-crystalline and/or amorphous forms of the compounds.

As used herein, the term "solvates" refers to compounds described herein complexed with a solvent molecule. It is appreciated that compounds described herein may form such complexes with solvents by simply mixing the compounds with a solvent, or dissolving the compounds in a solvent. It is appreciated that where the compounds are to be used as pharmaceuticals, such solvents are pharmaceutically acceptable solvents. It is further appreciated that where the compounds are to be used as pharmaceuticals, the relative amount of solvent that forms the solvate should be less than established guidelines for such pharmaceutical uses, such as less than International Conference on Harmonization (ICH) Guidelines. It is to be understood that the solvates may be isolated from excess solvent by evaporation, precipitation, and/or crystallization. In some embodiments, the solvates are amorphous, and in other embodiments, the solvates are crystalline.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the terms "alkenyl" and "alkynyl" each include a chain of carbon atoms, which is optionally branched, and include at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$, and $C_2$-$C_{24}$, $C_2$-$C_{12}$, $C_2$-$C_8$, $C_2$-$C_6$, and $C_2$-$C_4$, and the like. Illustratively, such particularly limited length alkyl groups, including $C_1$-$C_8$, $C_1$-$C_6$, and $C_1$-$C_4$, and $C_2$-$C_8$, $C_2$-$C_6$, and $C_2$-$C_4$, and the like may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$, and $C_3$-$C_{24}$, $C_3$-$C_{12}$, $C_3$-$C_8$, $C_3$-$C_6$, and $C_3$-$C_4$, and the like. Illustratively, such particularly limited length alkenyl and/or alkynyl groups, including $C_2$-$C_8$, $C_2$-$C_6$, and $C_2$-$C_4$, and $C_3$-$C_8$, $C_3$-$C_6$, and $C_3$-$C_4$, and the like may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$, and $C_2$-$C_{24}$, $C_2$-$C_{12}$, $C_7$-$C_8$, $C_2$-$C_6$, and $C_2$-$C_4$, and the like. Illustratively, such particularly limited length alkylene groups, including $C_1$-$C_8$, $C_1$-$C_6$, and $C_1$-$C_4$, and $C_2$-$C_8$, $C_2$-$C_6$, and $C_2$-$C_4$, and the like may be referred to as lower alkylene. It is to be further understood that in certain embodiments, alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$, and $C_3$-$C_{24}$, $C_3$-$C_{12}$, $C_3$-$C_8$, $C_3$-$C_6$, and $C_3$-$C_4$, and the like. Illustratively, such particularly limited length alkenylene and/or alkynylene groups, including $C_2$-$C_8$, $C_2$-$C_6$, and $C_2$-$C_4$, and $C_3$-$C_8$, $C_3$-$C_6$, and $C_3$-$C_4$, and the like may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopenyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylic acid and derivatives thereof" includes the group $CO_2H$ and salts thereof, and esters and amides thereof, and CN.

As used herein, the term "sulfinic acid or a derivative thereof" includes $SO_2H$ and salts thereof, and esters and amides thereof.

As used herein, the term "sulfonic acid or a derivative thereof" includes $SO_3H$ and salts thereof, and esters and amides thereof.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical —$(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl) aminoalkyl, alkylcarbonylaminoalkyl, N—($C_1$-$C_6$ alkyl) alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165. It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl and optionally substituted heteroaryl($C_2$-$C_{16}$)alkanoyl, such as the aryl or heteroaryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "leaving group" refers to a reactive functional group that generates an electrophilic site on the atom to which it is attached such that nucleophiles may be added to the electrophilic site on the atom. Illustrative leaving groups include, but are not limited to, halogens, optionally substituted phenols, acyloxy groups, sulfonoxy groups, and the like. It is to be understood that such leaving groups may be on alkyl, acyl, and the like.

Such leaving groups may also be referred to herein as activating groups, such as when the leaving group is present on acyl. In addition, conventional peptide, amide, and ester coupling agents, such as but not limited to PyBop, BOP-Cl, BOP, pentafluorophenol, isobutylchloroformate, and the like, form various intermediates that include a leaving group, as defined herein, on a carbonyl group.

It is to be understood that in every instance disclosed herein, the recitation of a range of integers for any variable describes the recited range, every individual member in the range, and every possible subrange for that variable. For example, the recitation that n is an integer from 0 to 8, describes that range, the individual and selectable values of 0, 1, 2, 3, 4, 5, 6, 7, and 8, such as n is 0, or n is 1, or n is 2, etc. In addition, the recitation that n is an integer from 0 to 8 also describes each and every subrange, each of which may for the basis of a further embodiment, such as n is an integer from 1 to 8, from 1 to 7, from 1 to 6, from 2 to 8, from 2 to 7, from 1 to 3, from 2 to 4, etc.

As used herein, the terms "treating", "contacting" or "reacting" when referring to a chemical reaction generally mean to add or mix two or more reagents under appropriate conditions that allows a chemical transformation or chemical reaction to take place, and/or to produce the indicated and/or the desired product. It is to be understood that the reaction which produces the indicated and/or the desired product may not necessarily result directly from the combination of two reagents which were initially added. In other words, there may be one or more intermediates which are produced in the mixture which ultimately leads to the formation of the indicated and/or the desired product.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. In addition, it is to be understood that the compositions may be prepared from various co-crystals of the compounds described herein.

Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

In addition to the illustrative dosages and dosing protocols described herein, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The dosage of each compound of the claimed combinations depends on several factors, including: the administration method, the condition to be treated, the severity of the condition, whether the condition is to be treated or prevented, and the age. weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the coadministered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "administering" as used herein includes all means of introducing the compounds and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and/or vehicles.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

The term "antagonist," as used herein, refers to a full or partial antagonist. While a partial antagonist of any intrinsic activity may be useful, the partial antagonists illustratively show at least about 50% antagonist effect, or at least about 80% antagonist effect. The term also includes compounds that are full antagonists of one or more vasopressin receptors. It is appreciated that illustrative methods described herein require therapeutically effective amounts of vasopressin receptor antagonists; therefore, compounds exhibiting partial antagonism at one or more vasopressin receptors may be administered in higher doses to exhibit sufficient antagonist activity to inhibit the effects of vasopressin or a vasopressin agonist.

The effective use of the compounds, compositions, and methods described herein for treating or ameliorating one or more effects of a neurodegenerative disease using one or more compounds described herein may be based upon animal models, such as murine, canine, porcine, and non-human primate animal models of disease. For example, it is understood that neurodegenerative diseases in humans may be characterized by a loss of function, and/or the development of symptoms, each of which may be elicited in animals, such as mice, and other surrogate test animals. In particular the mouse models described herein may be used to evaluate the methods of treatment and the pharmaceutical compositions described herein to determine the therapeutically effective amounts described herein.

Each publication cited herein is incorporated herein by reference.

The following examples further illustrate specific embodiments of the invention; however, the following illustrative examples should not be interpreted in any way to limit the invention.

EXAMPLES

Method Examples

Example

Human vasopression $V_{1a}$ receptor binding assay. A cell line expressing the human $V_{1a}$ receptor in CHO cells (henceforth referred to as the $hV_{1a}$ cell line) was obtained from Dr. Michael Brownstein, NIMH, Bethesda, Md., USA. The $hV_{1a}$ cDNA sequence is described by Thibonnier et al., Journal of Biological Chemistry, 269, 3304-3310 (1994), and the expression method was the same as described by Morel et al. (1992). The $hV_{1a}$ cell line was grown in alpha-MEM with 10% fetal bovine serum and 250 ug/ml G418 (Gibco, Grand Island, N.Y., USA). For competitive binding assay, hV1a cells were plated into 6-well culture plate at 1:10 dilution from a confluency flask, and maintained in culture for at least two days. Culture medium was then removed, cells were washed with 2 ml binding buffer (25 mM Hepes, 0.25% BSA, 1× DMEM, PH=7.0). To each well, 990 µl binding buffer containing 1 nM 3H-AVP was added, and followed by 10 µl series diluted Example compounds dissolved in DMSO. All incubations were in triplicate, and dose-inhibition curves consisted of total binding (DMSO) and 5 concentrations (0.1, 1.0, 10, 100, and 1000 nM) of test agents encompassing the $IC_{50}$. 100 nM cold AVP (Sigma) was used to assess non-specific binding. Cells were incubated for 45 minutes at 37° C., assay mixture was removed and each well was washed three times with PBS (pH=7.4). 1 ml 2% SDS was added per well and plates were let sit for 30 minutes. The whole content in a well was transferred to a scintillation vial. Each well was rinsed with 0.5 ml PBS which was then added to the corresponding vial. Scintillation fluid (Ecoscint, National Diagnostics, Atlanta, Ga.) was then added at 3 ml per vial. Samples were counted in a liquid scintillation counter (Beckman LS3801). $IC_{50}$ values were calculated by Prism Curve fitting software.

All of the alkanedioic esters and amides exemplified in the foregoing examples dissolved in DMSO were tested in this assay. Binding curves were generated according to methods described by Thibonnier et al. (1994). [$^3$H]-AVP was added to the hV1a cell cultures followed by 10-fold dilutions of each test compound. All active compounds showed a dose-dependent competitive binding curve, with $IC_{50}$ and $K_i$ values characteristic of high affinity binding to $V_{1a}$ receptors in CHO cells expressing the human $V_{1a}$ receptor (the hV1a cell line). For example, Example 225 showed a dose-dependent competitive binding curve, with $IC_{50}$ (1.86-2.13 nM) and $K_i$ (1.14-1.30 nM) values.

Binding affinities ($IC_{50}$) and inhibition constants ($K_i$) for illustrative compounds are shown in the following Table.

| Example | $V_{1a}$ Binding Affinity $IC_{50}$ (nM) | $V_{1a}$ $K_i$ (nM) |
| --- | --- | --- |
| 18 | 35 | — |
| 19 | 35 | — |
| 20 | 35 | — |
| 35 | 1.9 | 1.17 |
| 37 | 5.5 | 3.39 |

-continued

| Example | V$_{1a}$ Binding Affinity IC$_{50}$ (nM) | V$_{1a}$ K$_i$ (nM) |
|---|---|---|
| 38 | <25 | 85 |
| 39 | 23 | 13.3 |
| 40 | 11 | 6.5 |
| 41 | <20 | 18.2 |
| 42 | <20 | 26.4 |
| 42A | 1.77 | 1.17 |
| 44 | 3.1 | 1.89 |
| 47 | ~50 | — |
| 59 | <100 | — |
| 63 | 1.84 | 1.13 |
| 66 | ~50 | — |
| 77 | <100 | — |
| 78 | <100 | — |
| 81 | <100 | — |
| 82 | <50 | 5.12 |
| 85 | 5.87 | 3.6 |
| 86A | 9.79 | 6 |
| 87 | 15 | — |
| 88 | 2.4 | 1.45 |
| 91 | 3.24 | 1.99 |
| 95 | 1.76 | 1.08 |
| 96 | 4.35 | 2.66 |
| 100 | <100 | — |
| 101 | ~100 | — |
| 102 | <100 | — |
| 103 | 0.81 | 0.49 |
| 104 | 1.85 | 1.13 |
| 106 | ~100 | — |
| 107 | <50 | — |
| 108 | ~100 | — |
| 109 | ~100 | — |
| 110 | 0.49 | 0.27 |
| 111 | 1.31 | 0.82 |
| 112 | 1.34 | 0.8 |
| 120 | 0.75 | 0.46 |
| 120A | 16.2 | 9.9 |
| 120B | 2.93 | 1.79 |
| 120E | 3.2 | 1.95 |
| 120H | 2.75 | 1.68 |
| 132D | 6.3 | 3.9 |
| 132F | 4.8 | 3 |
| 133 | 2.43 | 1.49 |
| 134A | 12.9 | 7.9 |
| 134B | 44.8 | 27.5 |
| 134C | 9.1 | 5.58 |
| 134G | 6 | 3.7 |
| 134J | 5.29 | 3.25 |
| 135 | ~50 | — |
| 136 | 11 | 33 |
| 137 | 17 | 10.5 |
| 138 | 21 | 13 |
| 139 | 9.5 | 5.84 |
| 172 | 4.5 | 2.78 |
| 173 | <100 | — |
| 174 | 1.46 | 0.89 |
| 175 | 4.56 | 2.79 |
| 176 | 0.61 | 0.38 |
| 177 | 0.67 | 0.41 |
| 178 | <50 | — |
| 179 | 0.81 | 0.51 |
| 180 | 0.33 | 0.2 |
| 181 | <50 | — |
| 182 | 1.52 | 0.93 |
| 183 | <10 | — |
| 184 | <10 | — |
| 185 | 1.27 | 0.82 |
| 186 | <10 | — |
| 187 | 1 | 0.66 |
| 188 | 7.26 | 4.45 |
| 189 | 1.7 | 1.04 |
| 190 | 0.88 | 0.54 |
| 191 | 2.92 | 1.79 |
| 192 | <10 | — |
| 193 | 1.17 | 0.72 |
| 194 | <100 | — |
| 195 | <50 | — |
| 196 | <100 | — |
| 198 | ~100 | — |
| 199 | <10 | — |
| 200 | 5.08 | 3.11 |
| 201 | 10.5 | 6.43 |
| 203 | 2.46 | 1.5 |
| 204 | 6 | 3.7 |
| 205 | 0.34 | 0.21 |
| 206 | 1.58 | 0.97 |
| 207 | 4.48 | 2.74 |
| 208 | 16.3 | 10 |
| 209 | 16 | 9.8 |
| 210 | 29.5 | 18.1 |
| 211 | 5.37 | 3.29 |
| 212 | 0.95 | 0.58 |
| 213 | 0.78 | 0.48 |
| 214 | 1.86 | 1.14 |
| 215 | 0.61 | 0.38 |
| 216 | 1.83 | 1.12 |
| 217 | 3.17 | 1.94 |
| 218 | 7.7 | 4.7 |
| 219 | 0.63 | 0.39 |
| 220 | 5.3 | 3.26 |
| 221 | 5.1 | 3.1 |
| 221A | 2.71 | 1.66 |
| 221B | 0.59 | 0.36 |
| 221C | 3 | 1.84 |
| 221D | 2.41 | 1.48 |
| 221E | 20.2 | 12.4 |
| 221F | 1.7 | 1.04 |
| 221G | 1.5 | 0.93 |
| 221H | 4 | 2.5 |
| 221I | 12 | 7.4 |
| 221K | ~5 | — |
| 221O | 8.4 | 5.1 |
| 221P | 1.7 | 1.1 |
| 221Q | 18.1 | 11.1 |
| 221R | 5.13 | 3.14 |
| 221S | 5.03 | 3.08 |
| 221X | 11.6 | 7.2 |
| 221Y | 7.6 | 4.7 |
| 221AB | <10 | — |
| 221AC | <10 | — |
| 221AD | ~50 | — |
| 221AE | ~50 | — |
| 221AI | ~50 | — |
| 221AL | ~100 | — |
| 221AM | — | 2.7 |
| 221AP | — | 3.8 |
| 221AO | ~100 | — |
| 221AQ | ~50 | — |
| 221AS | ~20 | — |
| 221AX | 83 | 51 |
| 221AY | ~30 | — |
| 221BD | 2.7 | 1.66 |
| 221BI | 56 | 35 |
| 222 | 1.83 | 1.13 |
| 224 (SRX246) (AVN246) | 0.49 | 0.3 |
| 225 (SRX251) (AVN251) | 1.08 | 0.66 |
| 225-HCl | — | 1.36 |
| 225-MeI | 4.8 | 3 |
| 226 | 0.49 | 0.3 |
| 227 | 11 | 6.71 |
| 228 | 13.6 | 8.35 |
| 229 | 1.53 | 0.94 |
| 230 | 7.07 | 4.33 |
| 230F | ~100 | — |
| 230L | 12.7 | 7.8 |
| 231 | 6.12 | 3.75 |
| 232 | 1.37 | 0.84 |

-continued

| Example | $V_{1a}$ Binding Affinity $IC_{50}$ (nM) | $V_{1a}$ $K_i$ (nM) |
|---|---|---|
| 232D | 2.04 | 1.25 |
| 232E (SRX296) (AVN296) | 0.28 | 0.17 |
| 233 (SRX228) (AVN228) | 0.56 | 0.34 |
| 233A | — | 11.6 |
| 234 | 2.37 | 1.45 |
| 234A | 8.6 | 5.25 |
| 235 | 37 | 23 |
| 236 | 1.68 | 1.03 |
| 236A | 9 | 5.5 |
| 238 | 0.11 | 0.07 |
| 239 | 6.6 | 4 |
| 240 | 25 | 15.5 |
| 241 | 2.0 | 1.24 |
| 242 | 2.2 | 1.36 |
| 243 | 0.5 | 0.3 |
| 244 | 3.4 | 2.1 |
| 245 | 1.1 | 0.68 |
| 246 | 2.1 | 1.3 |
| 247 | 0.6 | 0.39 |
| 248 | 5.3 | 3.3 |
| 249 | 1.7 | 1 |
| 250 | 6.5 | 4 |
| 251 | 0.5 | 0.3 |
| 252 | 1.8 | 1.1 |
| 253 | 9.5 | 5.8 |
| 254 | 10 | 6.2 |
| 255 | 1.9 | 1.2 |
| 256 | 2.8 | 1.7 |
| 266 (SRX576) (AVN576) | 1.8 | 1.1 |
| 559 | 0.12 | 0.073 |
| 594 | — | 19 |
| 597 | 6.2 | 3.8 |
| 599 | 1.2 | 0.73 |
| 600 | 14.4 | 8.8 |
| 601 | 1 | 0.62 |
| 606 | 0.53 | 0.32 |
| 617 | — | 0.69 |
| 623 | — | 0.85 |
| 626 | — | 0.27 |
| 670 | — | 3.1 |
| 672 | — | 1.1 |
| 677 | — | 3 |
| 682 | — | 0.9 |
| 778 | — | 0.63 |

Example

Human vasopression $V_{1b}$ receptor-expressing cells. Human vasopressin receptor 1b (hV1b) cDNA (see, Lolait et al., "Extrapituitary expression of the rat V1b vasopressin receptor gene" Proc. Natl. Acad. Sci. USA. 92:6783-7 (1995); de Keyzer et al., "Cloning and characterization of the human V3(V1b) pituitary vasopressin receptor" FEBS Lett. 356:215-20 (1994); Sugimoto et al., "Molecular cloning and functional expression of a cDNA encoding the human V1b vasopressin receptor" J. Biol. Chem. 269: 27088-92 (1994)) was inserted into a mammalian cell expression vector PCI-neo (Promega) at EcoR1 site. The recombinant plasmid carrying hV1b cDNA was identified from transformed E. Coli clones and used for the transfection of Chinese hamster ovary cell (CHO-K1, ATCC). Two micrograms of hV1b receptor DNA was introduced into $10^5$ CHO cells cultured in 6-well plate, using Fugene-6 mediated transfection technique (Boehringer Mannheim). Twenty-four hrs post transfection, Cells were then cultured under selection of G-418 (0.25 mg/ml) supplemented to the culture medium. Three days later, limited dilution was carried out to obtain single cell clones in 96-well plates. After a period of 2-weeks of growth, monoclones were expanded into two sets of 12-well plates. When confluence was reached, one set of wells were assayed for their ability to bind tritium-labeled arginine-vasopressin (NEN). Nine positive clones were initially identified out of 60 clones screened, and clones that demonstrated highest AVP binding were saved as permanent cell lines for hV1b affinity screening.

Example

Human or rat vasopression $V_{1b}$ cell-based receptor binding assay. The V1b cell lines (cells expressing either the human or rat $V_{1b}$ receptor) were grown in alpha-MEM medium supplemented with 10% fetal bovine serum and 250 ug/ml G418 (Gibco, Grand Island, N.Y.) in 75 cm² flask. For competitive binding assay, hV1b cells were dissociated with enzyme-free, PBS based cell dissociation solution (Specialty Media, Phillipursburg, N.J.), following the manufacturer's protocol. Cells were plated into 12-well culture plates at a rate of one flask to 18 plates (rate should be adjusted according to the extent of confluency), and maintained in culture for 2-3 days. Culture medium was then removed, cells were washed once with 2 ml binding buffer (25 mM Hepes, 0.25% BSA, 1× DMEM, PH=7.0) at room temperature. To each well, 990 ul binding buffer containing 1 nM ³H-AVP was added, and followed by the addition of 10 ul series diluted testing compounds or cold AVP, all dissolved in DMSO. All incubations were in triplicate, and dose-inhibition curves consisted of total binding (DMSO only) and 5 concentrations (0.1, 1.0, 10, 100, and 1000 nm) of test agent, or cold AVP, encompassing the IC50. Cells were incubated for 30 min at 37° C. in a moisturized incubator. Assay mixture was then removed and each well was washed three times with PBS (pH=7.4). After washing, 1 ml 2% SDS was added per well and plates were let sit for 15 min at RT. Gently pat the plate to make sure that lysed cells were detached. The whole content in a well was transferred to a scintillation vial. Each well was then rinsed with 0.5 ml PBS and added to the corresponding vial. Scintillation fluid (Ecoscint, National Diagnostics, Atlanta, Ga.) was then added at 3 ml per vial. Samples were counted in a liquid scintillation counter (Beckman LS3801). IC50 and Ki values were calculated using Prism Curve fitting software. Illustrative compounds shown in the previous table show a binding constant greater than 100 nM, or greater than 1000 nM. Illustrative inhibition data (Ki, nM) are shown in the following table for selected Example compounds.

| Receptor | Example 224 (AVN246) | Example 225 (AVN251) | Example 266 (AVN576) |
|---|---|---|---|
| V1a | 0.30 | 0.66 | 1.1 |
| V1b | >1000 | >1000 | >100 |
| V2 | >1000 | >1000 | >1000 |

EXAMPLE. Inhibition of phosphatidylinositol turnover ($V_{1a}$). The physiological effects of vasopressin are mediated through specific G-protein coupled receptors. The vasopressin $V_{1a}$ receptor is coupled to the $G_q/G_{11}$ family of G proteins and mediates phosphatidylinositol turnover. The agonist or antagonist character of the compounds of the invention may be determined by their ability to inhibit vasopressin-mediated turnover of phosphatidylinositol by the procedure described in the following paragraphs. Illustrative compounds, Examples 35, 44, 88, 110, and 133, were tested in this assay and found to be vasopressin $V_{1a}$ antagonists.

EXAMPLE. Inhibition of vasopressin $V_{1b}$-mediated phosphatidylinositol turnover, a functional assay for antagonist activity. The physiological effects of vasopressin are mediated through specific G-protein coupled receptors. The vasopressin $V_{1b}$ receptor is coupled to a G protein, which is coupled to cAMP. The agonist or antagonist character of the compounds described herein may be determined by their ability to inhibit vasopressin-mediated turnover of phosphatidylinositol by using conventional methods, including the procedure described in the following paragraphs.

Cell culture and labeling of cells. Three days prior to the assay, near-confluent cultures of hV1a or hV1b cells were dissociated and seeded in 6-well tissue culture plates, about 100 wells being seeded from each 75 cm$^2$ flask (equivalent to 12:1 split ratio). Each well contained 1 mL of growth medium with 2 µCi of [$^3$H]myo-inositol (American Radiolabeled Chemicals, St. Louis, Mo., USA).

Cells expressing the human or rat $V_{1b}$ receptors are grown in alpha-modified minimal essential medium containing 10% fetal bovine serum and 0.25 mg/ml G418. Three days prior to the assay, near-confluent cultures are dissociated and seeded in 6-well tissue culture plates, about 100 wells being seeded from each 75 cm$^2$ flask (equivalent to 12:1 split ratio). Each well contains 1 ml of growth medium with 2 µCi of [$^3$H] myo-inositol (American Radiolabeled Chemicals, St. Louis, Mo.).

Incubations ($V_{1a}$ and $V_{1b}$). All assays were in triplicate except for basal and 10 nM AVP (both n=6). AVP ((arginine vasopressin), Peninsula Labs, Belmont, Calif., USA (#8103)) was dissolved in 0.1N acetic acid. Test agents were dissolved in DMSO and diluted in DMSO to 200 times the final test concentration. Test agents and AVP (or corresponding volumes of DMSO) were added separately as 5 µL in DMSO to 12×75 mm glass tubes containing 1 mL of assay buffer (Tyrode's balanced salt solution containing 50 mM glucose, 10 mM LiCl, 15 mM HEPES pH 7.4, 10 µM phosphoramidon, and 100 µM bacitracin). The order of incubations was randomized. Incubations were initiated by removing the prelabeling medium, washing the monolayer once with 1 mL of 0.9% NaCl, and transferring the contents of the assay tubes to corresponding wells. The plates were incubated for 1 hour at 37° C. Incubations were terminated by removing the incubation medium and adding 500 µL of ice cold 5% (w/v) trichloroacetic acid and allowing the wells to stand for 15 mM.

Measurement of [$^3$H]inositol phosphates ($V_{1a}$ and $V_{1b}$). BioRad Poly-Prep Econo-Columns were packed with 0.3 mL of AG 1 X-8 100-200 formate form resin. Resin was mixed 1:1 with water and 0.6 mL added to each column. Columns were then washed with 10 mL water. Scintillation vials (20 mL) were placed under each column. For each well, the contents were transferred to a minicolumn, after which the well was washed with 0.5 mL distilled water, which was also added to the minicolumn. The columns were then washed twice with 5 mL of 5 mM myo-inositol to elute free inositol. Aliquots (1 mL) were transferred to 20 mL scintillation vials and 10 mL of Beckman Ready Protein Plus added. After the myo-inositol wash was complete, empty scintillation vials were placed under the columns, and [$^3$H] inositol phosphates were eluted with three additions of 1 mL 0.5 M ammonium formate containing 0.1 N formic acid. Elution conditions were optimized to recover inositol mono-, bis-, and trisphosphates, without eluting the more metabolically inert tetrakis-, pentakis-, and hexakis-phosphates. To each sample was added 10 mL of a high salt capacity scintillation fluid such as Tru-Count High Salt Capacity or Packard Hionic-Fluor. Inositol lipids were measured by adding 1 mL of 2% sodium dodecyl sulfate (SDS) to each well, allowing the wells to stand for at least 30 min., and transferring the solution to 20 mL scintillation vials, to which 10 mL Beckman Ready Protein Plus scintillation fluid was then added. Samples were counted in a Beckman LS 3801 liquid scintillation counter for 10 min. Total inositol incorporation for each well was calculated as the sum of free inositol, inositol phosphates, and inositol lipids.

Data analysis ($V_{1a}$ and $V_{1b}$): concentration-inhibition experiments. Concentration-response curves for AVP and concentration-inhibition curves for test agents versus 10 nM AVP were analyzed by nonlinear least-squares curve-fitting to a 4-parameter logistic function. Parameters for basal and maximal inositol phosphates, $EC_{50}$ or $IC_{50}$, and Hill coefficient were varied to achieve the best fit. The curve-fitting was weighted under the assumption that the standard deviation was proportional to dpm of radioactivity. Full concentration-response curves for AVP were run in each experiment. $IC_{50}$ values were converted to $K_i$ values, which reflect the antagonistic activities against AVP in the production of signaling molecule IP3, by application of the Cheng-Prusoff equation, based on the $EC_{50}$ for AVP in the same experiment. Inositol phosphates were expressed as dpm per $10^6$ dpm of total inositol incorporation.

Data analysis ($V_{1a}$ and $V_{1b}$): competitivity experiments. Experiments to test for $V_{1a}$ competitivity of test agents consisted of concentration-response curves for AVP in the absence and presence of two or more concentrations of test agent. Experiments to test for $V_{1b}$ competition by test agents consist of concentration-response curves for AVP in the absence and presence of at least five concentrations of test agent. Data were fit to a competitive logistic equation $$Y = B + \frac{M \times \{A/[E+(D/K)]\}^Q}{1 + \{A/[E+(D/K)]\}^Q}$$

where Y is dpm of inositol phosphates, B is concentration of basal inositol phosphates, M is the maximal increase in concentration of inositol phosphates, A is the concentration of agonist (AVP), E is the $EC_{50}$ for agonist, D is the concentration of antagonist (test agent), K is the $K_i$ for antagonist, and Q is the cooperativity (Hill coefficient).

Compound Example 225 produces a dose-dependent suppression of the action of AVP with $IC_{50}$ (2.68 nM) and $K_i$ (0.05 nM). These values are consistent with high affinity binding of Example 225 and its inhibition of inositol lipid synthesis via the human $V_{1a}$ receptor.

EXAMPLE. AVPR1A expression in HD brain. It has been surprisingly discovered that AVPR1A expression in HD brain is equivalent to normal brain. High quality RNA (Integrity Number>7) was prepared from cerebral cortical samples from post-mortem HD brain and age/sex matched with post-mortem normal brain using standard methods. Reverse transcription (RT) was performed (12 control RNAs, 10 HD RNAs) and Real Time quantitative PCR was conducted following manufacturer's protocols. Samples were loaded in quadruplicate; no-template (negative) and no-RT controls were included. The expression levels of V1a mRNA were normalized to β-actin. Data analysis was performed using the CFX Manager™ Software, showing that V1a receptor mRNA levels in HD and control brains were similar. Therefore, though the neurodegeneration in HD has resulted in the loss of significant tissue and function, vasopressin signaling is still functioning at levels equivalent to healthy controls. Nonetheless, because of the neurodegeneration, it is believed herein that such otherwise normal levels of AVP and AVPR1a represent an excessive signaling condition in the HD patient.

EXAMPLE. AVP signaling modulation in human brain, a model of the neuropsychiatric aspects of neurodegenerative disease. It has been discovered herein that selective antagonists of AVPR1a are efficacious in treating the neuropsychiatric symptoms of HD, AD, and PD. Compounds described herein, including SRX228, SRX246, SRX251, SRX296, and SRX576, achieve therapeutically effective concentrations in the areas of the brain where an excessive signaling condition exists in neurodegenerative disease, and therefore, are efficacious in correcting the dysfunction in HD, AD, and PD.

EXAMPLE. Neurodegenerative disease (ND) model. Test subjects are randomized to an ND model group (for example, n=15), and a baseline control group (for example, n=14). The ND model group is administered intranasal arginine vasopressin (IN-AVP), 40 IU Pitressin (JHP Pharmaceuticals) in a sterile aqueous solution. IN-AVP doses are administered in 3 mL intranasal atomizers (MAD300; Wolfe Tory Medical, Salt Lake City) 45 minutes prior to fMRI imaging. The baseline control group is administered intranasal vehicle only. All test subjects are evaluated by fMRI imaging.

EXAMPLE. fMRI imaging. Data are acquired with a Philips Achieva Quasar dual 16 Channel 3T MRI scanner at the University of Chicago Brain Research Imaging Center using a reverse spiral imaging sequence to minimize ventral brain signal dropout. The Blood Oxygen Level Dependent (BOLD) signal is acquired while each test subject views 4 blocks of each unfamiliar emotional facial expression (Ekman faces), with each block lasting 20 seconds and consisting of 5 faces of each emotion category displayed for 4 seconds. Categories include: angry faces, neutral faces, happy faces, and a fixation point. Test subjects are given the "implicit" task of identifying the gender of each image by button press. Statistical parametric maps are generated based on pre-processed 3 mm³ images that are spatially smoothed with an 8 mm kernel, bandpass filtered to remove drift, checked for excessive movement, and movement-corrected. Images from each individual are warped to an echoplanar image template in Montreal Neurological Institute space. Voxelwise whole brain analysis is conducted on data thresholded at >10 contiguous voxels, with small volume correction $p<0.05$, to examine effects of test compound versus placebo on BOLD activity in a priori regions of interest (ROI). ROIs of the identified clusters of BOLD differences are extracted as parameter estimates of average BOLD signal intensity in anatomically defined substructures and exported into SPSS (IBM; Armont, N.Y.) for ANCOVA, covarying for baseline parameter estimates in matching ROIs. Extracted parameter estimates of a priori ROIs are also examined with RM-ANOVA in SPSS with the within subjects factor and between subjects factors of all combinations of test compound versus placebo, and IN-AVP versus intranasal placebo. Comparisons are made between emotion conditions (angry faces) and various neutral conditions (neutral faces, happy faces, fixation points). Comparisons are also made between emotion conditions (neutral faces) and various neutral conditions (happy faces, fixation points).

All test subjects in both the baseline control group and the ND model group show increased BOLD signal in specific regions of the brain, as messured by fMRI, when viewing angry faces. All test subjects in both the baseline control group and the ND model group show decreased BOLD signal in those same regions when viewing happy faces or a fixation point. Increased BOLD signal is observed specifically in the right and left temporoparietal cortex (TPC), the precuneus, the anterior cingulate cortex and medial prefrontal cortex, the amygdala, and the putamen. Those regions of the brain are involved in social recognition and emotional processing. In particular, activation of the left TPC reflects attentiveness, and activation of the right TPC is associated with thinking about the thoughts and motives of others. Neurons in this region send their axons to the anterior cingulate and medial prefrontal cortices where executive decisions are made about the nature of the perceived emotional input, to identify threats, and to make decisions and appropriate responses. Under conditions representing excessive signaling, such executive functions or decisions are compromised, resulting in inappropriate aggressive behavior, irritability, and/or anger.

Consistent with the foregoing theory of mind, when viewing angry faces, test subjects in the ND model group receiveing IN-AVP show an amplified BOLD signal compared to the baseline control group receiveing intranasal placebo. Moreover, test subjects in the ND model group show increased BOLD signal when viewing neutral faces compared to the baseline control group, where BOLD signal is similar when viewing neutral faces, happy faces, and fixation points. An increased BOLD signal when viewing neutral faces is consistent with a misinterpretation of the emotional condition represented by the neutral face as a perceived threat, and the triggering of aggressive behavior, irritability, and/or anger. Such misinterpretation of the emotional condition is observed with the loss of control of executive functions in neurodegenerative diseases, including HD, AD, and PD. The foregoing supports the conclusion that an excessive vasopressin signaling condition is present in neurodegenerative diseases, such as HD, AD, and PD.

EXAMPLE. Neuropsychiatric symptom treatment with vasopressin antagonists. A first group of test subjects in a baseline control group receiving intranasal placebo is randomized to test compound or placebo. A second group of test subjects in a ND model group receiving IN-AVP is randomized to test compound or placebo. Test compound, such as SRX228, SRX246, SRX251, SRX296, or SRX576, or placebo is administered in blinded form for 5-10 days (mean 7.3+/−1.3 days; minimum 5 days; maximum 11 days) prior to fMRI. Alternatively, test compound, such as SRX228. SRX246, SRX251, SRX296, anord SRX576, or placebo is administered in blinded form after IN-AVP or intranasal placebo administration, and prior to fMRI. All subjects randomized to test compound (n=15) show demonstrable levels of test compound, and all subjects randomized to placebo (n=14) do not show detectable levels of test compound. For example, test compound is SRX246 (n=15; 80, 120, or 160 mg po bid) versus placebo (n=14) in oral capsules; or test compound is SRX251 (n=15; 80, 120, or 160 mg po bid) versus placebo (n=14) in oral capsules.

BOLD signal is significantly decreased in all test subjects pretreated with test compound compared to placebo, when viewing angry faces. BOLD signal is significantly decreased in all test subjects posttreated with test compound compared to placebo, when viewing angry faces. BOLD signal is significantly decreased in the ND model test subjects receiving IN-AVP pretreated with test compound compared to placebo, when viewing neutral faces. BOLD signal is significantly decreased in ND model test subjects receiving IN-AVP posttreated with test compound compared to placebo, when viewing neutral faces.

FIG. 1 shows a high resolution structural template of the decrease in BOLD signal in the temporoparietal cortex (Brodmann Area 39) after pretreatment with SRX246 in the ND model group receiving IN-AVP. Compared to placebo, pretreatment with SRX246 significantly decreases (p<0.001, >10 contiguous voxels) the BOLD activation signal following IN-AVP in the temporoparietal cortex (Brodmann Area 39) (block white areas showing the T-statistic value) and amygdala when viewing angry faces versus a fixation point. The grayscale bar indicates the T-statistic value, where the observed activity changes within this region survived regional correction for Type II error (Family Wise Error (FEW) corrected p=0.017; T (1, 27)=4.59).

Compared to placebo, posttreatment with SRX246 significantly decreases (p<0.05, >10 contiguous voxels) the BOLD activation signal following IN-AVP in the temporoparietal cortex (Brodmann Area 39) and amygdala when viewing angry faces versus happy faces (data not shown).

Figure 2:
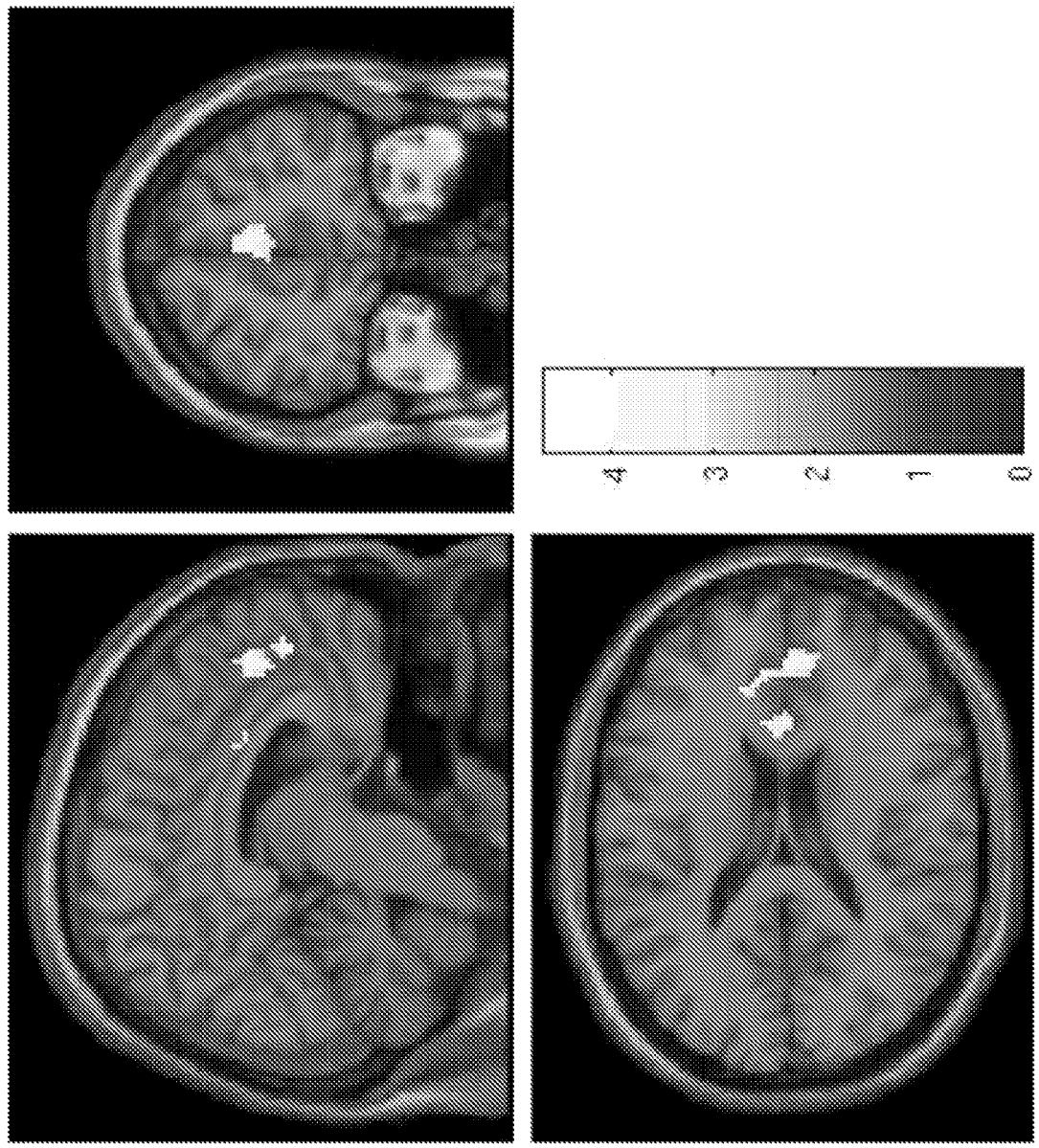
FIG. 2 shows a high resolution structural template of the decrease in BOLD signal in the anterior cingulate cortex and medial prefrontal cortex.

FIG. 2 shows a high resolution structural template of the decrease in BOLD signal in the anterior cingulate cortex and medial prefrontal cortex after pretreatment with SRX246 in the ND model group receiving IN-AVP. Compared to placebo, pretreatment with SRX246 significantly decreases (p<0.005, >10 contiguous voxels) the BOLD activation signal following IN-AVP in the medial prefrontal cortex when viewing angry faces versus a fixation point, and significantly attenuated cortical reactivity to angry faces in the anterior cingulate cortex and medial superior prefrontal cortex (block white areas showing the T-statistic value). The grayscale bar indicates the T-statistic value, where the observed activity changes within this region survived regional correction for Type II error (FWE corrected p=0.015; T (1, 27)=4.66).

Compared to placebo, posttreatment with SRX246 significantly decreases the BOLD activation signal following IN-AVP in the anterior cingulate cortex and medial prefrontal cortex when viewing angry faces versus happy faces.

EXAMPLE. Resident-intruder model of stress and aggression in rats. Neuroimaging is used to assess the blockade of stress/arousal with test compound compared to control. The effect of AVN251-HCl on functional circuitry was examined using the imaging method for awake rats. Additional details of the assay are described in Ferris et al. Imaging the neural circuitry and chemical control of aggressive motivation. BMC Neuroscience 9: 111 (2008). A representation of CNS effects of AVN251-HCl and differentiated neurobiological changes produced by AVN251-HCl are compared to fluoxetine. AVN251-HCl leaves sexual motivation intact while fluoxetine markedly diminishes activation of this circuit resulting in a decrease in libido and reaction to a receptor female.

Male rats in the company of a female cage mate piloerect in the presence of a male intruder. Piloerection is a sign of stress and aggressive intent and is associated with activation of stress/arousal circuits in the brain. Stress circuit activation in response to an intruder male is assessed by obtaining brain scans viewed from a caudal/dorsal perspective as translucent shells. The localization of activated voxels is mapped as 3D volumes of activation, which are composed of 10 subjects each. Once fully registered and segmented, the statistical responses for each subject are averaged on a voxel-by-voxel basis. Those averaged voxels exceeding a 2.0% threshold are shown in their appropriate spatial location. Functional images are acquired on awake rats at 4.7 T.

Resident male rats from six male/female pairs are imaged while fully awake, and presented with their mate, or their mate+an intruder, a highly stressful stimulus. During a single imaging session, males are treated with oral administration of Example 225 (AVN251) (5 mg/kg), Example 224 (AVN246) (5 mg/kg), or vehicle by oral gavage. The total volume of brain activation for resident males confronted with their mate alone, mate plus intruder, and mate plus intruder in the presence of AVN251-HCl are viewed as 3D models. AVN251-HCl treatment (5 mg/kg) blocks activation of this stress circuit. There is a general decrease in BOLD signal in major regions with AVN251-HCl treatment that are responsible for inappropriate behavior. However, sexual motivation, as assessed by the presentation of a novel receptive female, is unaffected by V1a receptor blockade. The mesocorticolimbic dopamine reward system function in response to a sexually motivating stimulus (an estrogen-progesterone primed female) remains intact in the presence of AVN251-HCl. Imaging shows robust activation of the different brain regions when the novel female is presented as a stimulus. Further, male residents treated with AVN251-HCl show normal sexual behavior toward receptive females (estrogen/progesterone treated ovariectomized novel females) in their home cage environment. In particular, SRX251-HCl selectively blocks aggressive motivation but not sexual motivation, as evidenced by minimal changes in the BOLD signal in the primary olfactory system, and reward pathways in the mesocorticolimbic dopaminergic system, including the prelimbic cortex, accumbens, ventral pallidum, medial dorsal thalamus, and ventral tegmentum. In contrast, treatment with fluoxetine results in decreased activation of both the stress circuits and the mesocorticolimbic dopamine reward system.

Figure 3:
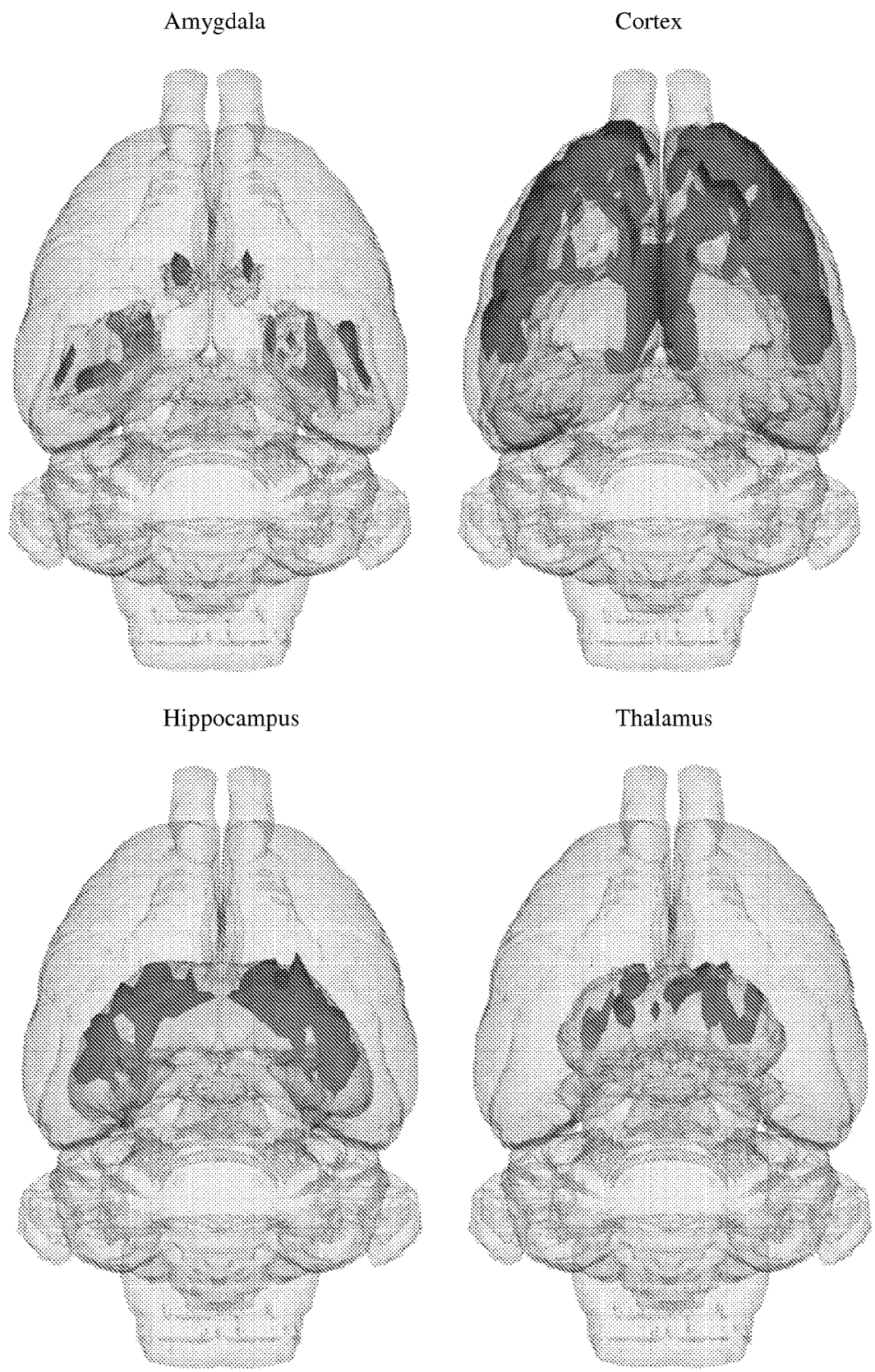
FIG. 3 shows the brain scans for the amygdala, cortex, hippocampus, and thalamus for untreated controls during the mate+intruder stress paradigm.
Figure 4:
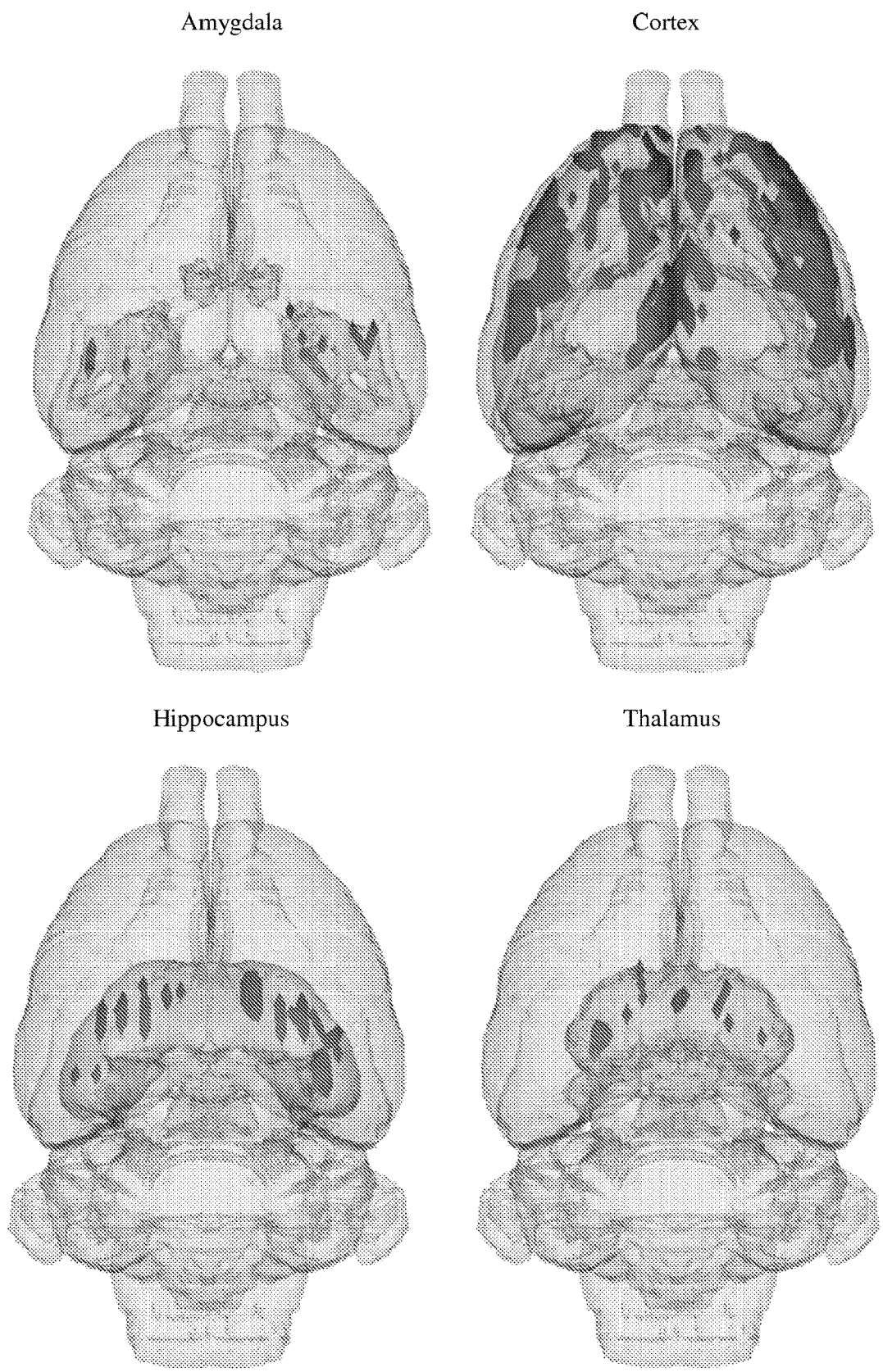
FIG. 4 shows the brain scans for the amygdala, cortex, hippocampus, and thalamus for animals pretreated with SRX251 during the mate+intruder stress paradigm.

EXAMPLE. Neuroimaging of specific brain regions showing blockade of stress. Awake rats are imaged when presented with their mate, or their mate+an intruder. Pretreatment with AVN251 (5 mg/kg) or AVN246 (5 mg/kg) 90 minutes before the test session blocked the stress/arousal response specifically in regions of the brain responsible for emotional processing and threat evaluation, including the amygdala, cortex (temporoparietal cortex, anterior cingulate cortex, and medial prefrontal cortex), hippocampus, and thalamus. Similar results are observed with SRX228, SRX246, SRX251, SRX296, and SRX576. Sexual motivation and behavior remained intact. Separate areas of the brain were evaluated, including amygdala, cortex, hippocampus, and thalamus, each showing similar results. FIG. 3 shows the brain scans for the amygdala, cortex, hippocampus, and thalamus for untreated controls during the mate+intruder stress paradigm. FIG. 4 shows the brain scans for the amygdala, cortex, hippocampus, and thalamus for animals pretreated with SRX251 during the mate+intruder stress paradigm. In each scan, the dark shaded areas represent activation of vasopressin receptor signaling. In each case, the treated animals (FIG. 4) showed lower activation of vasopressin receptor signaling than the untreated controls (FIG. 3) in each of the brain regions.

EXAMPLE. Resident-Intruder Model in Hamster. Placing an unfamiliar male hamster into the home cage of another male hamster elicits a well-defined sequence of agonistic behaviors from the resident that includes offensive aggression. Male Syrian golden hamsters (*Mesocricetus auratus*) (140-150 g) obtained from Harlan Sprague-Dawley Laboratories (Indianapolis, Ind.) are housed individually in Plexiglas cages (24 cm×24 cm×20 cm), maintained on a reverse light/dark cycle (14L:10D; lights on at 19:00 hr) and provided food and water ad libitum. Animals are acclimated to the reverse light:dark cycle for at least two weeks before testing. All behavioral tests are conducted during the dark phase of the circadian cycle.

Behavioral Measures and Analysis. Hamsters are nocturnal and as such behavioral tests are performed during the first four hours of the dark phase under dim red illumination. The resident is scored for stress, e.g., latency to bite the intruder, total contact time with the intruder, the total number of bites, and flank marking, over a 10 minute test period (Ferris & Potegal (1988)). Flank marking is a form of olfactory communication in which a hamster arches its back and rubs pheromone producing flank glands against objects in the environment (Johnston, R. E. Communication, In: The Hamster Reproduction and Behavior. Ed Siegel, H. I. Plenum Press, New York, pp 121-154 (1985)). Flank marking frequency is greatly enhanced during aggressive encounters and is particularly robust in dominant animals initiating and winning fights (Ferris et al., Physiology and Behavior, 40:661-664 (1987)).

The compounds described herein are tested using five groups of five animals each over a range of doses (100 ng/kg, 10 µg/kg, 1 mg/kg, 10 mg/kg, and saline vehicle as control). Ninety min after oral gavage an intruder is placed into the home cage and the resident scored for offensive aggression. Following aggression testing, animals are screened for motor activity in an open field paradigm and sexual motivation.

Parametric data, i.e., latencies and contact time, are analyzed with a one-way ANOVA followed by Newman-Keuls post hoc tests. Non-parametric data, i.e., number of bites and flank marks, are analyzed with Kruskal-Wallis tests followed by Mann-Whitney U tests to determine differences between groups.

The latency to bite is increased and the number of bites decreased by the administration of compounds described herein, indicating a lower stress level in treated animals. Contact time may also be increased.

EXAMPLE. Mouse Chronic Subordination Model of Depression. Social stress is a factor in the etiology of several psychopathologies, with individuals differing in vulnerability. Adult male mice are subjected to a model of chronic psychosocial stress in which resident/intruder dyads live chronically in sensory contact and physically interact on a daily basis. The intruder animals chronically subordinated by this procedure exhibit behaviors characteristic of depression and depression-related disorders.

EXAMPLE. Anti-depressant Effect in the Social Interaction Test. Chronic social subjugation is a standard method for producing animals that exhibit depression-like physiological and behavioral profiles. A rapid subjugation paradigm in mice lead to diminished social interaction behavior, where the dependent measures are distance traveled and time in the Interaction Zone. A 28-day treatment regimen with chlordiazepoxide (CDP), a standard anxiolytic, had no effect on deficits produced by chronic subordination. Additional details are described in Berton et al. Essential role of BDNF in the mesolimbic dopamine pathway in social defeat stress. Science 311(5762):864-8 (Feb. 10, 2006).

Briefly, C57B1/6J males are defeated daily for 10 days by resident, highly aggressive CF-1 males. After 5 minutes of direct exposure, a perforated plastic partition is inserted into the cage that allowed olfactory and visual contact without physical defeat for the remaining 23 hr 55 min each day. The C57 males are exposed to a different resident male in a different cage each day to increase the stress of the procedure (it is observed that all CF-1 males attacked the intruder each day). At the end of the 10 day defeat procedure, the C57 males are tested in an open field apparatus during the dark phase. A dominant male is caged in an area of the open field apparatus termed the "social interaction zone." Time and distance traveled in the zone are recorded. The C57 males are then divided randomly among the following treatments: AVN246-HCl (2 mg/kg), saline vehicle (0.45%), or chlordiazepoxide (10 mg/kg). Treatments are given daily (i.p.) for 28 days and the animals are retested. Behavioral changes are determined by calculating difference scores (Post-Pretest) and these scores are analyzed.

As shown in the Table, AVN251-HCl treatment significantly increased both distance traveled and time in the interaction zone, indicating that the compounds described herein reverse deficits in social interaction behaviors after social subjugation.

| Example | Time | Distance |
| --- | --- | --- |
| SRX251-HCl | 35 ± 10 [a] | 22 ± 6 [a] |
| CDP | 0.0 ± 5 | 1.0 ± 5 |
| Saline | 10 ± 10 | −15 ± 8 |

[a] significantly different from CDP and Saline ($p < 0.05$).

Figure 5:
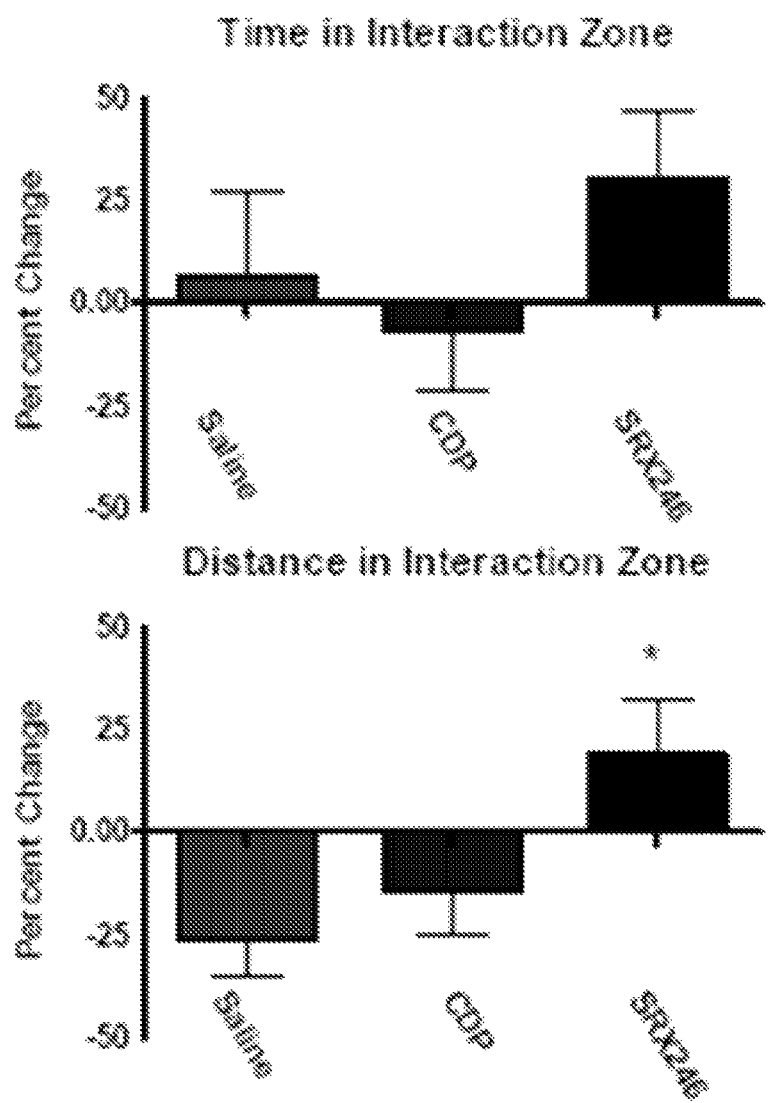
FIG. 5 shows a comparison of vehicle treated, chlordiazepoxide (CDP), and treatment with SRX246 in social interaction test.

(a) significantly different from CDP and Saline (p<0.05). A statistically significant difference (p<0.05) was observed between the test compound and both the untreated control (saline) and negative control chlordiazepoxide (CDP). CDP, a standard anxiolytic, had no effect. The results confirm that deficits in the social interaction induced by chronic subordination are responsive to compounds described herein, but not anxiolytics. AVN246 is observed to give similar results, as shown in FIG. 5. A statistically significant difference (*, p<0.05) was observed between the test compound and untreated control (saline) and negative control chlordiazepoxide (CDP) in the distance travelled in the interaction zone.

Figure 6:
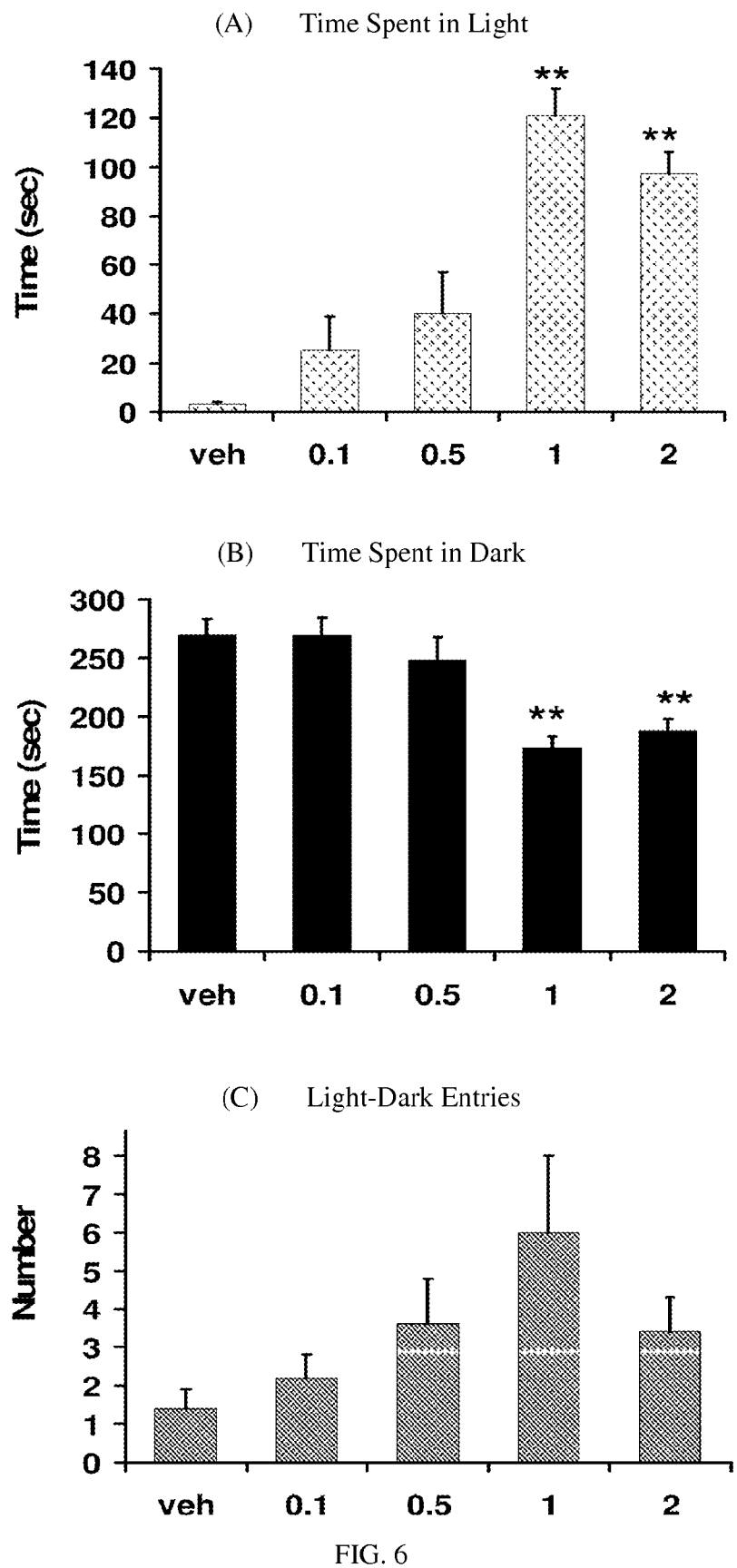
FIG. 6A, FIG. 6B, and FIG. 6C show time test animals spent in the light, time test animals spent in the dark, and the number of light-dark entrres in a light/dark shuttle box test.

EXAMPLE. Anxiolytic Effect in the Light/Dark Shuttle Box. The light/dark shuttle box is a standard and well characterized assay for anxiolytic effects of a test compound. Rats naturally avoid the light side of the box because it is stressful. Increased time on the light side by the treatment group compared to control reflects an anxiolytic effect (Bourin and Hascoet, 2003). Adult male Long Evans rats are administered AVN251 (0.1-2 mg/kg) by oral gavage 90 min prior to testing in a light/dark shuttle box. A dose dependent decrease in anxiety is observed in response to AVN251 compared to vehicle. In a dose dependent manner, test animals spent significantly p<0.01) more time in the light (FIG. 6A), significantly (, p<0.01) less time in the dark (FIG. 6B), and made more light-dark entries (FIG. 6C**) following treatment with 1 or 2 mg/kg AVN251.

EXAMPLE. Pharmacokinetics. Compounds described herein are rapidly absorbed after oral administration. Compounds described herein cross the blood-brain-barrier and achieve therapeutically effective concentrations in the CNS. Compounds described herein may be dosed according to a wide variety of protocols, including but not limited to q.d., b.i.d., and the like. Compounds described herein exhibit dose-related increases in Cmax and AUC when dosed according to various protocols, including but not limited to q.d., b.i.d. For example, b.i.d. dosing shows a 1.7-fold accumulation and improved $T_{1/2}$ for SRX246.

EXAMPLE. General Synthetic Routes. Proximal amide approach which permits synthetic variation at the distal amide site; proximal amide is set first, followed by distal amide diversity by parallel synthesis.

43
44
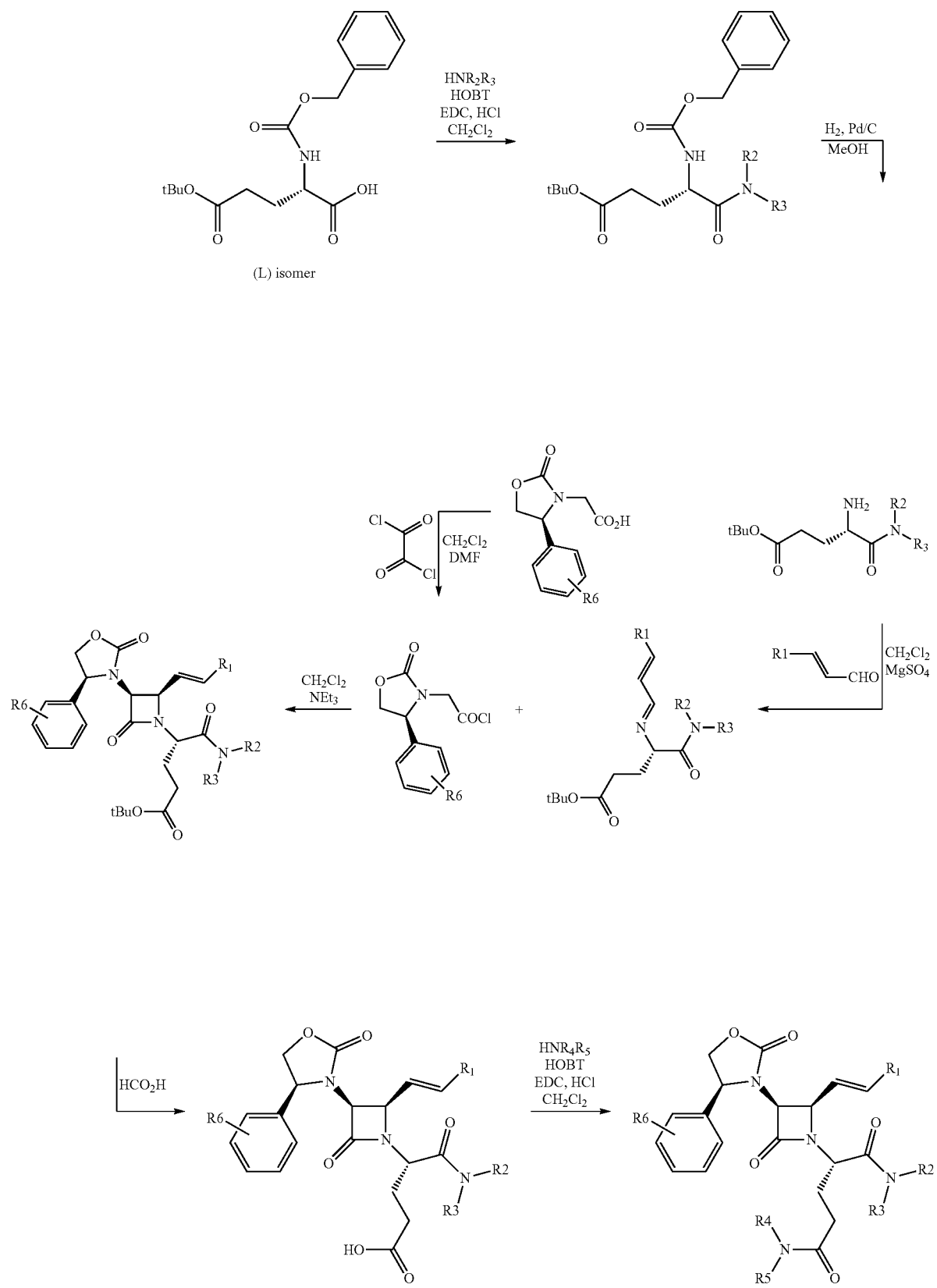

Distal amide approach which permits synthetic variations at the proximal site; distal amide is set first, followed by proximal amide diversity by parallel synthesis.
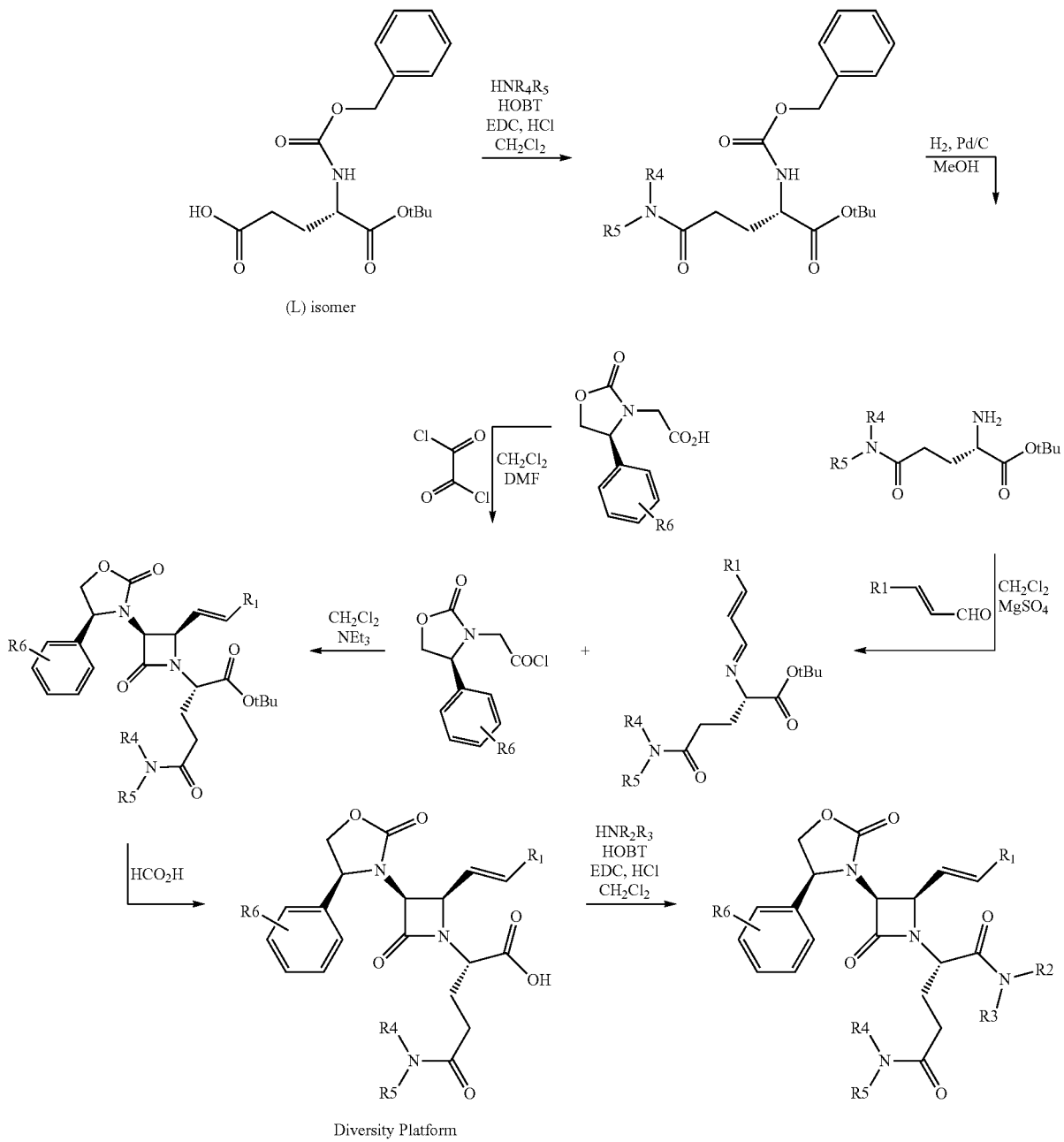
Synthesis of AVN251 is shown below. All other compounds are prepared in an analogous manner with the appropriate selecteoin of starting materials.
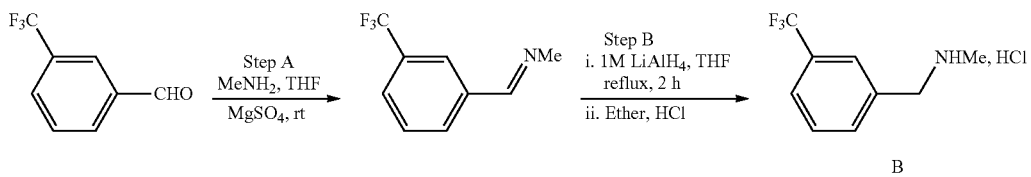
B

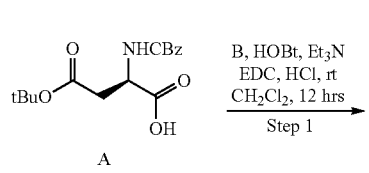
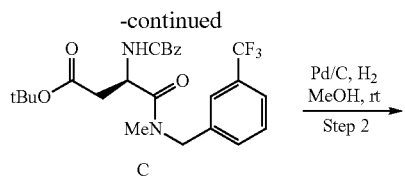
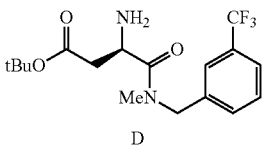
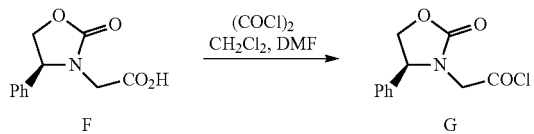
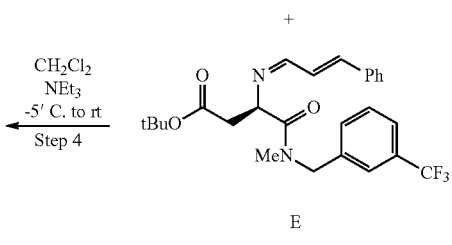
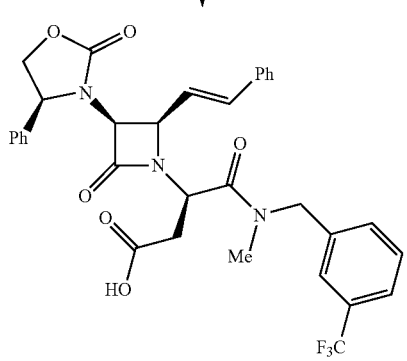
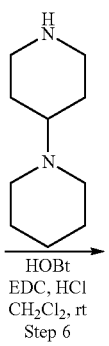
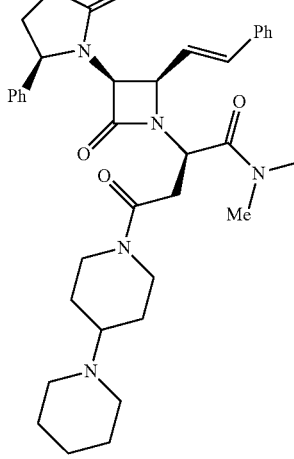
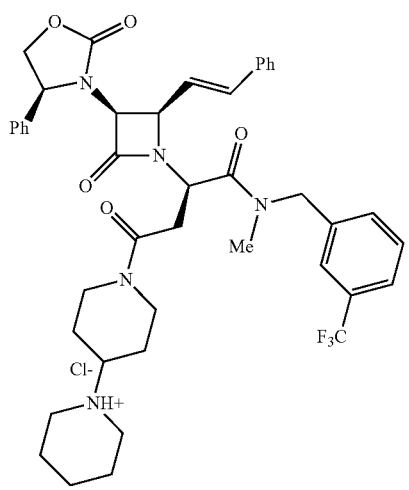

Additional details and alternative syntheses for preparing compounds described herein are described in U.S. Pat. No. 7,119,083, the disclosure of which are incorporated herein by reference in their entirety. The compounds described herein may be formulated and administered according to the processes described in U.S. Pat. No. 7,119,083. Additional details are described in Guillon, C. D., et al., Azetidinones as vasopressin V1a antagonists. Bioorg Med Chem, 15(5): 2054-80 (2007).

COMPOUND EXAMPLES

Example 1. (4(S)-phenyloxazolidin-2-on-3-yl)acetyl chloride

A solution of 1.0 equivalent of (4(S)-phenyloxazolidin-2-on-3-yl)acetic acid (Evans, U.S. Pat. No. 4,665,171) and 1.3 equivalent of oxalyl chloride in 200 mL dichloromethane was treated with a catalytic amount of anhydrous dimethylformamide (85 µL/milliequivalent of acetic acid derivative) resulting in vigorous gas evolution. After 45 minutes all gas evolution had ceased and the reaction mixture was concentrated under reduced pressure to provide the title compound as an off-white solid after drying for 2 h under vacuum.

Example 1A.
(4(R)-phenyloxazolidin-2-on-3-yl)acetyl chloride

Example 1A was prepared following the procedure of Example 1, except that (4(R)-phenyloxazolidin-2-on-3-yl) acetic acid was used instead of (4(S)-phenyloxazolidin-2-on-3-yl)acetic acid (see, Evans & Sjogren, Tetrahedron Lett. 26:3783 (1985)).

Example 1B. Methyl (4(S)-phenyloxazolidin-2-on-3-yl)acetate

A solution of (4(S)-phenyloxazolidin-2-on-3-yl)acetic acid (1 g, 4.52 mmol) (prepared according to Evans in U.S. Pat. No. 4,665,171) in 20 mL of anhydrous methanol was treated hourly with 5 equivalents of acetyl chloride, for a total of 20 equivalents. The resulting solution was stirred overnight. The residue obtained after evaporation of the MeOH was redissolved in 30 mL of $CH_2Cl_2$ and treated with 50 mL of saturated aqueous $Na_2CO_3$. The organic layer was evaporated and dried ($MgSO_4$) to yield the title compound as a colorless oil (1.001 g, 94%); $^1$H NMR ($CDCl_3$) δ 3.37 (d, J=18.0 Hz, 1H), 3.69 (s, 3H), 4.13 (t, J=8.3 Hz, 1H), 4.28 (d, J=18.0 Hz, 1H), 4.69 (t, J=8.8 Hz, 1H), 5.04 (t, J=8.4 Hz, 1H), 7.26-7.29 (m, 2H), 7.36-7.42 (m, 3H).

Example 1C. Methyl 2-(4(S)-phenyloxazolidin-2-on-3-yl)propanoate

A solution of methyl (4(S)-phenyloxazolidin-2-on-3-yl) acetate (1 g, 4.25 mmol) in 10 mL of anhydrous THF at −78° C. was treated with 4.68 mL (4.68 mmol) of a 1 M solution of lithium bis(trimethylsilyl)amide in THF. The reaction mixture was stirred for 1 h. at about −70° C. before adding MeI (1.59 mL, 25.51 mmol). Upon complete conversion of the azetidinone, the reaction was quenched with saturated aqueous $NH_4Cl$ and partitioned between EtOAc and water. The organic layer was washed sequentially with saturated aqueous sodium bisulfite, and saturated aqueous NaCl. The resulting organic layer was dried ($MgSO_4$) and evaporated to afford the title compound (a mixture of diasteromers) as a white solid (1.06 g, 93%); $^1$H NMR ($CDCl_3$) δ 1.07/1.53 (d/d, J=7.5 Hz, 3H), 3.59/3.74 (s/s, 3H), 3.85/4.48 (q/q. J=7.5 Hz, 1H), 4.10-4.14 (m, 1H), 4.60-4.64/4.65-4.69 (m/m, 1H), 4.88-4.92/4.98-5.02 (m/m, 1H), 7.24-7.40 (m, 5H).

Example 1D.
2-(4(S)-Phenyloxazolidin-2-on-3-yl)propanoic acid

To a solution of methyl 2-(4(S)-phenyloxazolidin-2-on-3-yl)propanoate (1 g, 4.01 mmol) in 35 mL of MeOH was added, at 0° C., 14.3 mL (12.04 mmol) of a 0.84 M solution of LiOH in water. The reaction mixture was then stirred for 3 h. at ambient temperature. Upon complete hydrolysis of the azetidinone, the MeOH was removed by evaporation, the crude residue dissolved in $CH_2Cl_2$ and treated with saturated aqueous NaCl. The resulting organic layer was dried ($MgSO_4$) and evaporated to afford the title compound (racemic mixture) as a white solid (0.906 g, 96%); $^1$H NMR ($CDCl_3$) δ 1.13/1.57 (d/d, J=7.5 Hz, 3H), 3.75/4.50 (q/q, J=7.5 Hz, 1H), 4.10-4.16 (m, 1H), 4.62-4.72 (m, 1H), 4.92-5.03 (m, 1H), 7.32-7.43 (m, 5H).

Example 1E.
2-(4(S)-Phenyloxazolidin-2-on-3-yl)propanoyl chloride

A solution of 1 equivalent of Example 1D and 1.3 equivalent of oxalyl chloride in 200 mL $CH_2Cl_2$ (150 mL/g of propanoic acid derivative) was treated with a catalytic amount of anhydrous DMF (85 µL/mmole of propanoic acid derivative) resulting in vigorous gas evolution. After 45 min., all gas evolution had ceased and the reaction mixture was concentrated under reduced pressure to provide the title compound as an off-white solid after drying for 2 h. under vacuum.

Example 2. General Procedure for Amide Formation from an Activated Ester Derivative N-Benzyloxycarbonyl-L-aspartic acid β-t-butyl ester α-(3-trifluoromethyl)benzylamide. A solution of N-benzyloxycarbonyl-L-aspartic acid β-t-butyl ester α-N-hydroxysuccinimide ester (1.95 g, 4.64 mmol, Advanced ChemTech) in 20 mL of dry tetrahydrofuran was treated with 0.68 mL (4.74 mmol) of 3-(trifluoromethyl)benzyl amine. Upon completion (TLC, 60:40 hexanes/ethyl acetate), the mixture was evaporated, and the resulting oil was partitioned between dichloromethane and a saturated aqueous solution of sodium bicarbonate. The organic laer was evaporated to give 2.23 g (quantitative yield) of the title compound as a white solid; $^1$H NMR ($CDCl_3$) δ 1.39 (s, 9H), 2.61 (dd, J=6.5 Hz, J=17.2 Hz, 1H), 2.98 (dd, J=3.7 Hz, J=17.0 Hz, 1H), 4.41 (dd, J=5.9 Hz, J=15.3 Hz, 1H), 4.50-4.57 (m, 2H), 5.15 (s, 2H), 5.96-5.99 (m, 1H), 6.95 (s, 1H), 7.29-7.34 (m, 5H), 7.39-7.43 (m, 2H), 7.48-7.52 (m, 2H).

Examples 2A-2C and 3-5 were prepared according to the procedure of Example 2, except that N-benzyloxycarbonyl-L-aspartic acid β-t-butyl ester α-N-hydroxysuccinimide ester was replaced by the appropriate amino acid derivative, and 3-(trifluoromethyl)benzyl amine was replaced with the appropriate amine.

Example 2A. N-Benzyloxycarbonyl-L-aspartic acid β-t-butyl ester α-[4-(2-phenylethyl)]piperazinamide N-benzyloxycarbonyl-L-aspartic acid β-t-butyl ester α-N-hydroxysuccinimide ester (5.0 g, 12 mmol, Advanced ChemTech) and 4-(phenylethyl)piperazine 2.27 mL (11.9 mmol) gave 5.89 g (quantitative yield) of the title compound as an off-white oil; $^1$H NMR (CDCl$_3$) δ 1.40 (s, 9H), 2.45-2.80 (m, 10H), 3.50-3.80 (m, 4H), 4.87-4.91 (m, 1H), 5.08 (s, 2H), 5.62-5.66 (m, 1H), 7.17-7.33 (m, 10H).

Example 2B. N-Benzyloxycarbonyl-L-glutamic acid γ-butyl ester α-(3-trifluoromethyl)benzylamide N-benzyloxycarbonyl-L-glutamic acid β-t-butyl ester α-N-hydroxysuccinimide ester (4.83 g, 11.1 mmol, Advanced ChemTech) and 3-(trifluoromethyl)benzylamine) 1.63 mL (11.4 mmol) gave 5.41 g (98%) of the title compound as an off-white solid; $^1$H NMR (CDCl$_3$) δ 1.40 (s, 9H), 1.88-1.99 (m, 1H), 2.03-2.13 (m, 1H), 2.23-2.33 (m, 1H), 2.38-2.47 (m, 1H), 4.19-4.25 (s, 1H), 4.46-4.48 (m, 2H), 5.05-5.08 (m, 2H), 5.67-5.72 (m, 1H), 7.27-7.34 (m, 5H), 7.39-7.43 (m, 2H), 7.48-7.52 (m, 2H).

Example 2C. N-Benzyloxycarbonyl-L-glutamic acid γ-butyl ester α-[4-(2-phenylethyl)]piperazinamide N-benzyloxycarbonyl-L-glutamic acid γ-t-butyl ester α-N-hydroxysuccinimide ester (5.0 g, 12 mmol, Advanced ChemTech) and 4-(phenylethyl)piperazine 2.19 mL (11.5 mmol) gave 5.87 g (quantitative yield) of the title compound as an off-white oil; $^1$H NMR (CDCl$_3$) δ 1.43 (s, 9H); 1.64-1.73 (m, 1H); 1.93-2.01 (m, 1H); 2.23-2.40 (m, 2H); 2.42-2.68 (m, 6H); 2.75-2.85 (m, 2H); 3.61-3.74 (m, 4H); 4.66-4.73 (m, 1H); 5.03-5.12 (m, 2H); 5.69-5.72 (m, 1H); 7.16-7.34 (m, 10H).

Example 3. N-Benzyloxycarbonyl-L-aspartic acid β-t-butyl ester α-[4-(2-phenylethyl)]piperazinamide N-benzyloxycarbonyl-L-aspartic acid β-t-butyl ester α-N-hydroxysuccinimide ester (5.0 g, 12 mmol, Advanced ChemTech) and 4-(phenylethyl)piperazine 2.27 mL (11.9 mmol) gave 5.89 g (quantitative yield) of the title compound as an off-white oil; $^1$H NMR (CDCl$_3$) δ 1.40 (s, 9H), 2.45-2.80 (m, 10H), 3.50-3.80 (m, 4H), 4.87-4.91 (m, 1H), 5.08 (s, 2H), 5.62-5.66 (m, 1H), 7.17-7.33 (m, 10H).

Example 4. N-Benzyloxycarbonyl-L-glutamic acid γ-t-butyl ester α-(3-trifluoromethyl)benzylamide N-benzyloxycarbonyl-L-glutamic acid β-t-butyl ester α-N-hydroxysuccinimide ester (4.83 g, 11.1 mmol, Advanced ChemTech) and 3-(trifluoromethyl)benzylamine) 1.63 mL (11.4 mmol) gave 5.41 g (98%) of the title compound as an off-white solid; $^1$H NMR (CDCl$_3$) δ 1.40 (s, 9H), 1.88-1.99 (m, 1H), 2.03-2.13 (m, 1H), 2.23-2.33 (m, 1H), 2.38-2.47 (m, 1H), 4.19-4.25 (s, 1H), 4.46-4.48 (m, 2H), 5.05-5.08 (m, 2H), 5.67-5.72 (m, 1H), 7.27-7.34 (m, 5H), 7.39-7.43 (m, 2H), 7.48-7.52 (m, 2H).

Example 5. N-Benzyloxycarbonyl-L-glutamic acid γ-t-butyl ester α-[4-(2-phenylethyl)]piperazinamide N-benzyloxycarbonyl-L-glutamic acid γ-t-butyl ester α-N-hydroxysuccinimide ester (5.0 g, 12 mmol, Advanced ChemTech) and 4-(phenylethyl)piperazine 2.19 mL (11.5 mmol) gave 5.87 g (quantitative yield) of the title compound as an off-white oil; $^1$H NMR (CDCl$_3$) δ 1.43 (s, 9H); 1.64-1.73 (m, 1H); 1.93-2.01 (m, 1H); 2.23-2.40 (m, 2H); 2.42-2.68 (m, 6H); 2.75-2.85 (m, 2H); 3.61-3.74 (m, 4H); 4.66-4.73 (m, 1H); 5.03-5.12 (m, 2H); 5.69-5.72 (m, 1H); 7.16-7.34 (m, 10H).

Example 5A. N-[(9H-Fluoren-9-yl)methoxycarbonyl]-O-(benzyl)-D-serine t-Butyl ester N-[(9H-Fluoren-9-yl)methoxycarbonyl]-O-(benzyl)-D-serine (0.710 g, 1.70 mmole) in dichloromethane (8 mL) was treated with t-butyl acetate (3 mL) and concentrated sulfuric acid (40 µL) in a sealed flask at 0° C. Upon completion (TLC), the reaction was quenched with of dichloromethane (10 mL) and saturated aqueous potassium bicarbonate (15 mL). The organic layer was washed with distilled water, and evaporated. The resulting residue was purified by flash column chromatography (98:2 dichloromethane/methanol) to yield the title compound as a colorless oil (0.292 g, 77%); $^1$H NMR (CDCl$_3$) δ 1.44 (s, 9H); 3.68 (dd, J=2.9 Hz, J=9.3 Hz, 1H); 3.87 (dd, J=2.9 Hz, J=9.3 Hz, 1H); 4.22 (t, J=7.1 Hz, 1H); 4.30-4.60 (m, 5H); 5.64-5.67 (m, 1H); 7.25-7.39 (m, 9H); 7.58-7.61 (m, 2H); 7.73-7.76 (m, 2H).

Example 5B. O-(Benzyl)-D-serine t-Butyl ester

Example 5A (0.620 g, 1.31 mmol) in dichloromethane (5 mL) was treated with tris(2-aminoethyl)amine (2.75 mL) for 5 h. The resulting mixture was washed twice with a phosphate buffer (pH=5.5), once with saturated aqueous potassium bicarbonate, and evaporated to give 0.329 g (quantitative yield) of the title compound as an off-white solid; $^1$H NMR (CD$_3$OD) δ 1.44 (s, 9H); 3.48 (dd, J=J'=4.2 Hz, 1H); 3.61 (dd, J=4.0 Hz, J=9.2 Hz, 1H); 3.72 (dd, J=4.6 Hz, J=9.2 Hz, 1H); 4.47 (d, J=12.0 Hz, 1H); 4.55 (d, J=12.0 Hz, 1H); 7.26-7.33 (m, 5H).

Example 6. General Procedure for Amide Formation from a Carboxylic Acid

N-Benzyloxycarbonyl-D-aspartic acid β-t-butyl ester α-(3-trifluoromethyl)benzylamide. A solution of 1 g (2.93 mmol) of N-benzyloxycarbonyl-D-aspartic acid β-t-butyl ester monohydrate (Novabiochem) in 3-4 mL of dichloromethane was treated by sequential addition of 0.46 mL (3.21 mmol) of 3-(trifluoromethyl)benzylamine, 0.44 g (3.23 mmol) of 1-hydroxy-7-benzotriazole, and 0.62 g (3.23 mmol) of 1-[3-(dimethylamino)propyl]-3-ethylcarbodiimide hydrochloride. After at least 12 hours at ambient temperature or until complete as determined by thin layer chromatography (95:5 dichloromethane/methanol eluent), the reaction mixture was washed sequentially with a saturated aqueous sodium bicarbonate solution and with distilled water. The organic layer was evaporated to give 1.41 g (quantitative yield) of the title compound as an off-white solid; $^1$H NMR (CDCl$_3$) δ 1.39 (s, 9H); 2.61 (dd, J=6.5 Hz, J=17.2 Hz, 1H); 2.98 (dd, J=4.2 Hz, J=17.2 Hz, 1H); 4.41 (dd, J=5.9 Hz, J=15.3 Hz, 1H); 4.50-4.57 (m, 2H); 5.10 (s, 2H); 5.96-6.01 (m, 1H); 6.91-7.00 (m, 1H); 7.30-7.36 (m, 5H); 7.39-7.43 (m, 2H); 7.48-7.52 (m, 2H).

Examples 7-7H were prepared according to the procedure of Example 6, except that N-benzyloxycarbonyl-D-aspartic acid β-t-butyl ester monohydrate was replaced by the appropriate amino acid derivative, and 3-(trifluoromethyl)benzyl amine was replaced with the appropriate amine.

Example 7. N-Benzyloxycarbonyl-D-glutamic acid γ-t-butyl ester α-(3-trifluoromethyl)benzylamide N-benzyloxycarbonyl-D-glutamic acid γ-t-butyl ester (1.14 g, 3.37 mmol) and 0.53 mL (3.70 mmol, Novabiochem) of 3-(trifluoromethyl)benzylamine gave 1.67 g (quantitative yield) of Example 7 as an off-white solid. Example 7 exhibited an $^1$H NMR spectrum consistent with the assigned structure.

Example 7A. N-Benzyloxycarbonyl-L-glutamic acid α-t-butyl ester γ-(4-cyclohexyl)piperazinamide N-benzyloxycarbonyl-L-glutamic acid α-t-butyl ester (1.36 g, 4.03 mmol) and 0.746 g (4.43 mmol) of 1-cyclohexylpiperazine gave 1.93 g (98%) of Example 7A as an off-white solid; $^1$H NMR (CDCl$_3$) δ 1.02-1.12 (m, 5H); 1.43 (s, 9H), 1.60-1.64 (m, 1H); 1.80-1.93 (m, 5H); 2.18-2.52 (m, 8H); 3.38-3.60 (m, 4H); 4.20-4.24 (m, 1H); 5.03-5.13 (m, 2H); 5.53-5.57 (m, 1H); 7.28-7.34 (m, 5H).

Example 7B. N-Benzyloxycarbonyl-D-aspartic acid β-t-butyl ester α-(2-fluoro-3-trifluoromethyl)benzylamide N-benzyloxycarbonyl-D-aspartic acid β-t-butyl ester monohydrate (Novabiochem) (0.25 g, 0.73 mmol) and 0.12 mL of (2-fluoro-3-trifluoromethyl)benzylamine gave 0.365 g (quantitative yield) of Example 7B as an off-white solid; $^1$H NMR (CDCl$_3$) δ 1.38 (s, 9H); 2.59 (dd, J=6.5 Hz, J=17.0 Hz, 1H); 2.95 (dd, J=4.3 Hz, J=17.0 Hz, 1H); 4.46-4.56 (m, 3H); 5.11 (s, 2H); 5.94-5.96 (m, 1H); 7.15 (t, J=8.0 Hz, 1H); 7.30-7.36 (m, 5H); 7.47-7.52 (m, 2H).

Example 7C. N-Benzyloxycarbonyl-D-aspartic acid β-t-butyl ester α-[(S)-α-methylbenzyl]amide N-benzyloxycarbonyl-D-aspartic acid β-t-butyl ester monohydrate (Novabiochem) (0.25 g, 0.73 mmol) and 0.094 mL of (S)-α-methylbenzylamine gave 0.281 g (90%) of Example 7C as an off-white solid; $^1$H NMR (CDCl$_3$) δ 1.41 (s, 9H); 1.44 (d, J=7.0 Hz, 3H); 2.61 (dd, J=7.0 Hz, J=17.0 Hz, 1H); 2.93 (dd, J=4.0 Hz, J=17.5 Hz, 1H); 4.50-4.54 (m, 1H); 5.04-5.14 (m, 3H); 5.94-5.96 (m, 1H); 6.76-6.80 (m, 1H); 7.21-7.37 (m, 10H).

Example 7D. N-Benzyloxycarbonyl-D-aspartic acid β-t-butyl ester α-[(R)-α-methylbenzyl]amide N-benzyloxycarbonyl-D-aspartic acid β-t-butyl ester monohydrate (Novabiochem) (0.25 g, 0.73 mmol) and 0.094 mL of (R)-α-methylbenzylamine gave 0.281 g (90%) of Example 7D as an off-white solid; $^1$H NMR (CDCl$_3$) δ 1.38 (s, 9H); 1.43 (d, J=6.9 Hz, 3H); 2.54 (dd, J=7.3 Hz, J=17.2 Hz, 1H); 2.87 (dd, J=4.1 Hz, J=17.3 Hz, 1H); 4.46-4.50 (m, 1H); 4.99-5.15 (m, 3H); 5.92-5.96 (m, 1H); 6.78-6.82 (m, 1H); 7.21-7.33 (m, 10H).

Example 7E. N-Benzyloxycarbonyl-D-aspartic acid γ-butyl ester α-[N-methyl-N-(3-trifluoromethylbenzy)]amide N-benzyloxycarbonyl-D-aspartic acid γ-butyl ester (0.303 g, 0.89 mmol, Novabiochem) and 0.168 g (0.89 mmol) of N-methyl-N-(3-trifluoromethylbenzyl)amine gave 0.287 g (65%) of Example 7E as an off-white solid; $^1$H NMR (CDCl$_3$) δ 1.40 (s, 9H); 2.55 (dd, J=5.8 Hz, J=15.8 Hz, 1H); 2.81 (dd, J=7.8 Hz, J=15.8 Hz, 1H); 3.10 (s, 3H); 4.25 (d, J=15.0 Hz, 1H); 4.80 (d, J=15.5 Hz, 1H); 5.01-5.13 (m, 3H); 5.52-5.55 (m, 1H); 7.25-7.52 (m, 10H).

Example 7F. N-Benzyloxycarbonyl-D-aspartic acid β-t-butyl ester α-[(S)-1-(3-trifluoromethylphenyl)ethyl]amide N-benzyloxycarbonyl-D-aspartic acid β-t-butyl ester monohydrate (Novabiochem) (84 mg, 0.25 mmol) and 47 mg of (S)-1-(3-trifluoromethylphenyl)ethylamine gave 122 mg (quantitative yield) of Example 7F as an off-white solid. Example 7F exhibited an $^1$H NMR spectrum consistent with the assigned structure.

Example 7G. N-Benzyloxycarbonyl-D-aspartic acid β-t-butyl ester α-[(R)-1-(3-trifluoromethylphenyl)ethyl]amide N-benzyloxycarbonyl-D-aspartic acid β-t-butyl ester monohydrate (Novabiochem) (150 mg, 0.44 mmol) and 83 mg of (R)-1-(3-trifluoromethylphenyl)ethylamine gave 217 mg (quantitative yield) of Example 7G as an off-white solid. Example 7G exhibited an $^1$H NMR spectrum consistent with the assigned structure.

Example 7H. N-Benzyloxycarbonyl-D-glutamic acid α-methyl ester γ-(3-trifluoromethyl)benzylamide N-benzyloxycarbonyl-D-glutamic acid α-methyl ester (508 mg, 1.72 mmol) and 317 mg (1.81 mmol) of 3-(trifluoromethyl)benzylamine gave 662 mg (85%) of Example 7H as an off-white solid. Example 7H exhibited an $^1$H NMR spectrum consistent with the assigned structure.

Example 8. General Procedure for Hydrogenation of a Benzyloxycarbonyl Amine

L-aspartic acid β-t-butyl ester α-(3-trifluoromethyl)benzylamide. A suspension of 2.23 g (4.64 mmol) of N-benzyloxycarbonyl-L-aspartic acid β-t-butyl ester α-(3-trifluoromethyl)benzylamide and palladium (5% wt. on activated carbon, 0.642 g) in 30 mL of methanol was held under an atmosphere of hydrogen until complete conversion as determined by thin layer chromatography (95:5 dichloromethane/methanol eluent). The reaction was filtered to remove the palladium over carbon and the filtrate was evaporated to give 1.52 g (96%) of the title compound as an oil; $^1$H NMR (CDCl$_3$) δ 1.42 (s, 9H); 2.26 (brs, 2H); 2.63-2.71 (m, 1H); 2.82-2.87 (m, 1H); 3.75-3.77 (m, 1H); 4.47-4.50 (m, 2H); 7.41-7.52 (m, 4H); 7.90 (brs, 1H).

Examples 9-13P were prepared according to the procedure of Example 8, except that N-benzyloxycarbonyl-L-aspartic acid β-t-butyl ester α-(3-trifluoromethyl)benzylamide was replaced by the appropriate amino acid derivative.

Example 9. L-aspartic acid β-t-butyl ester α-[4-(2-phenylethyl)]piperazinamide N-benzyloxycarbonyl-L-aspartic acid β-t-butyl ester α-[4-(2-phenylethyl)]piperazinamide (5.89 g, 11.9 mmol) gave 4.24 g (98%) of Example 9 as an off-white oil; $^1$H NMR (CDCl$_3$): δ 1.42 (s, 9H); 2.61-2.95 (m, 10H); 3.60-3.90 (m, 4H); 4.35-4.45 (m, 1H); 7.17-7.29 (m, 5H).

Example 10. D-aspartic acid β-t-butyl ester α-(3-trifluoromethyl)benzylamide N-benzyloxycarbonyl-D-aspartic acid β-t-butyl ester α-(3-trifluoromethyl)benzylamide (1.41 g, 2.93 mmol) gave 0.973 g (96%) of Example 10 as an off-white oil; $^1$H NMR (CDCl$_3$): δ 1.42 (s, 9H); 2.21 (brs, 2H); 2.67 (dd, J=7.1 Hz, J=16.8 Hz, 1H); 2.84 (dd, J=3.6 Hz, J=16.7 Hz, 1H); 3.73-3.77 (m, 1H); 4.47-4.50 (m, 2H); 7.41-7.52 (m, 4H); 7.83-7.87 (m, 1H).

Example 11. L-glutamic acid γ-t-butyl ester α-(3-trifluoromethyl)benzylamide N-benzyloxycarbonyl-L-glutamic acid γ-t-butyl ester α-(3-trifluoromethyl)benzylamide (5.41 g, 10.9 mmol) gave 3.94 g (quantitative yield) of Example 11 as an off-white oil; $^1$H NMR (CDCl$_3$): δ 1.41 (s, 9H); 1.73-1.89 (m, 3H); 2.05-2.16 (m, 1H); 2.32-2.38 (m, 2H); 3.47 (dd, J=5.0 Hz, J=7.5 Hz, 1H); 4.47-4.49 (m, 2H); 7.36-7.54 (m, 4H); 7.69-7.77 (m, 1H).

Example 12. L-glutamic acid γ-t-butyl ester α-[4-(2-phenylethyl)]piperazinamide N-benzyloxycarbonyl-L-glutamic acid γ-t-butyl ester α-[4-(2-phenylethyl)]piperazinamide (5.86 g, 11.50 mmol) gave 4.28 g (99%) of Example 12 as an off-white oil; $^1$H NMR (CDCl$_3$) δ 1.39 (s, 9H); 2.00-2.08 (m, 1H); 2.38-2.46 (m, 1H); 2.55-2.90 (m, 9H); 3.61-3.82 (m, 4H); 4.48-4.56 (m, 1H); 7.17-7.26 (m, 5H).

Example 13. D-glutamic acid γ-t-butyl ester α-(3-trifluoromethyl)benzylamide N-benzyloxycarbonyl-D-glutamic acid γ-t-butyl ester α-(3-trifluoromethyl)benzylamide (1.667 g, 3.37 mmol) gave 1.15 g (94%) of Example 13 as an off-white oil; $^1$H NMR (CDCl$_3$) δ 1.41 (s, 9H); 1.80-2.20 (m, 4H); 2.31-2.40 (m, 2H); 3.51-3.59 (m, 1H); 4.47-4.49 (m, 2H); 7.39-7.52 (m, 4H); 7.71-7.79 (m, 1H).

Example 13A. L-glutamic acid α-t-butyl ester γ-(4-cyclohexyl)piperazinamide

N-Benzyloxycarbonyl-L-glutamic acid α-t-butyl ester γ-(4-cyclohexyl)piperazinamide (1.93 g, 3.96 mmol) gave 1.30 g (93%) of Example 13A as an off-white oil; $^1$H NMR (CDCl$_3$) δ 1.02-1.25 (m, 5H); 1.41 (s, 9H); 1.45-1.50 (m, 1H); 1.56-1.60 (m, 1H); 1.69-1.80 (m, 6H); 3.30 (dd, J=4.8 Hz, J=8.5 Hz, 1H); 3.44 (t, J=9.9 Hz, 2H); 3.56 (t, J=9.9 Hz, 2H).

Example 13B. D-aspartic acid β-t-butyl ester α-(2-fluoro-3-trifluoromethyl)benzylamide N-benzyloxycarbonyl-D-aspartic acid β-t-butyl ester α-(2-fluoro-3-trifluoromethyl)benzylamide (0.36 g, 0.72 mmol) gave 0.256 g (92%) of Example 13B as an off-white oil; $^1$H NMR (CDCl$_3$) δ 1.39 (s, 9H); 2.50 (brs, 2H); 2.74 (dd, J=7.0 Hz, J=16.5 Hz, 1H); 2.86 (dd, J=4.8 Hz, J=16.8 Hz, 1H); 3.89 (brs, 2H); 4.47-4.57 (m, 2H); 7.16 (t, J=7.8 Hz, 1H); 7.48 (t, J=7.3 Hz, 1H); 7.56 (t, J=7.3 Hz, 1H); 7.97-8.02 (m, 1H).

Example 13C. D-aspartic acid β-t-butyl ester α-[(S)-α-methyl]benzylamide

N-benzyloxycarbonyl-D-aspartic acid β-t-butyl ester α-[(S)-α-methylbenzyl]amide (0.275 g, 0.65 mmol) gave 0.17 g (90%) of Example 13C as an off-white oil; $^1$H NMR (CDCl$_3$) δ 1.40 (s, 9H); 1.47 (d, J=6.9 Hz, 3H); 1.98 (brs, 2H); 2.49 (dd, J=7.9 Hz, J=17.7 Hz, 1H); 2.83 (dd, J=3.6 Hz, J=16.7 Hz, 1H); 3.69 (brs, 1H); 4.99-5.10 (m, 1H); 7.19-7.33 (m, 5H); 7.65-7.68 (m, 1H).

Example 13D. D-aspartic acid β-t-butyl ester α-[(R)-α-methylbenzyl]amide

N-benzyloxycarbonyl-D-aspartic acid β-t-butyl ester α-[(R)-α-methylbenzyl]amide (0.273 g, 0.64 mmol) gave 0.187 g (quantitative yield) of Example 13D as an off-white oil; $^1$H NMR (CDCl$_3$) δ 1.38 (s, 9H); 1.46 (d, J=6.9 Hz, 3H); 1.79 (brs, 2H); 2.51 (dd, J=7.8 Hz, J=17.5 Hz, 1H); 2.87 (dd, J=3.6 Hz, J=16.9 Hz, 1H); 4.19 (brs, 1H); 4.99-5.11 (m, 1H); 7.18-7.34 (m, 5H); 7.86-7.90 (m, 1H).

Example 13E. D-aspartic acid β-t-butyl ester α-[N-methyl-N-(3-trifluoromethylbenzy)]amide N-benzyloxycarbonyl-D-aspartic acid β-t-butyl ester α-[N-methyl-N-(3-trifluoromethylbenzyl)]amide (0.282 g, 0.57 mmol) gave 0.195 g (95%) of Example 13E as an off-white oil. Example 13E exhibited an $^1$H NMR spectrum consistent with the assigned structure.

Example 13F. L-aspartic acid β-t-butyl ester α-[4-(2-phenylethyl)]piperazinamide N-benzyloxycarbonyl-L-aspartic acid β-t-butyl ester α-[4-(2-phenylethyl)]piperazinamide (5.89 g, 11.9 mmol) gave 4.24 g (98%) of Example 13F as an off-white oil; $^1$H NMR (CDCl$_3$): δ 1.42 (s, 9H); 2.61-2.95 (m, 10H); 3.60-3.90 (m, 4H); 4.35-4.45 (m, 1H); 7.17-7.29 (m, 5H).

Example 13G. D-aspartic acid β-t-butyl ester α-(3-trifluoromethyl)benzylamide N-benzyloxycarbonyl-D-aspartic acid β-t-butyl ester α-(3-trifluoromethyl)benzylamide (1.41 g, 2.93 mmol) gave 0.973 g (96%) of Example 13G as an off-white oil; $^1$H NMR (CDCl$_3$): δ 1.42 (s, 9H); 2.21 (brs, 2H); 2.67 (dd, J=7.1 Hz, J=16.8 Hz, 1H); 2.84 (dd, J=3.6 Hz, J=16.7 Hz, 1H); 3.73-3.77 (m, 1H); 4.47-4.50 (m, 2H); 7.41-7.52 (m, 4H); 7.83-7.87 (m, 1H).

Example 13H. L-glutamic acid γ-t-butyl ester α-(3-trifluoromethyl)benzylamide N-benzyloxycarbonyl-L-glutamic acid γ-t-butyl ester α-(3-trifluoromethyl)benzylamide (5.41 g, 10.9 mmol) gave 3.94 g (quantitative yield) of Example 13H as an off-white oil; $^1$H NMR (CDCl$_3$): δ 1.41 (s, 9H); 1.73-1.89 (m, 3H); 2.05-2.16 (m, 1H); 2.32-2.38 (m, 2H); 3.47 (dd, J=5.0 Hz, J=7.5 Hz, 1H); 4.47-4.49 (m, 2H); 7.36-7.54 (m, 4H); 7.69-7.77 (m, 1H).

Example 13I. L-glutamic acid γ-t-butyl ester α-[4-(2-phenylethyl)]piperazinamide N-benzyloxycarbonyl-L-glutamic acid γ-t-butyl ester α-[4-(2-phenylethyl)]piperazinamide (5.86 g, 11.50 mmol) gave 4.28 g (99%) of Example 13I as an off-white oil; $^1$H NMR (CDCl$_3$) δ 1.39 (s, 9H); 2.00-2.08 (m, 1H); 2.38-2.46 (m, 1H); 2.55-2.90 (m, 9H); 3.61-3.82 (m, 4H); 4.48-4.56 (m, 1H); 7.17-7.26 (m, 5H).

Example 13J. D-glutamic acid γ-t-butyl ester α-(3-trifluoromethyl)benzylamide N-benzyloxycarbonyl-D-glutamic acid γ-t-butyl ester α-(3-trifluoromethyl)benzylamide (1.667 g, 3.37 mmol)

gave 1.15 g (94%) of Example 13J as an off-white oil; $^1$H NMR (CDCl$_3$) δ 1.41 (s, 9H); 1.80-2.20 (m, 4H); 2.31-2.40 (m, 2H); 3.51-3.59 (m, 1H); 4.47-4.49 (m, 2H); 7.39-7.52 (m, 4H); 7.71-7.79 (m, 1H).

Example 13K. L-glutamic acid α-t-butyl ester γ-(4-cyclohexyl)piperazinamide

N-Benzyloxycarbonyl-L-glutamic acid α-t-butyl ester γ-(4-cyclohexyl)piperazinamide (1.93 g, 3.96 mmol) gave 1.30 g (93%) of Example 13K as an off-white oil; $^1$H NMR (CDCl$_3$) δ 1.02-1.25 (m, 5H); 1.41 (s, 9H); 1.45-1.50 (m, 1H); 1.56-1.60 (m, 1H); 1.69-1.80 (m, 6H); 3.30 (dd, J=4.8 Hz, J=8.5 Hz, 1H); 3.44 (t, J=9.9 Hz, 2H); 3.56 (t, J=9.9 Hz, 2H).

Example 13L. D-aspartic acid β-t-butyl ester α-(2-fluoro-3-trifluoromethyl)benzylamide N-benzyloxycarbonyl-D-aspartic acid β-t-butyl ester α-(2-fluoro-3-trifluoromethyl)benzylamide (0.36 g, 0.72 mmol) gave 0.256 g (92%) of Example 13L as an off-white oil; $^1$H NMR (CDCl$_3$) δ 1.39 (s, 9H); 2.50 (brs, 2H); 2.74 (dd, J=7.0 Hz, J=16.5 Hz, 1H); 2.86 (dd, J=4.8 Hz, J=16.8 Hz, 1H); 3.89 (brs, 2H); 4.47-4.57 (m, 2H); 7.16 (t, J=7.8 Hz, 1H); 7.48 (t, J=7.3 Hz, 1H); 7.56 (t, J=7.3 Hz, 1H); 7.97-8.02 (m, 1H).

Example 13M. D-aspartic acid β-t-butyl ester α-[(S)-1-(3-trifluoromethylphenyl)ethyl]amide N-benzyloxycarbonyl-D-aspartic acid β-t-butyl ester α-[(S)-1-(3-trifluoromethylphenyl)ethyl]amide (120 mg, 0.24 mmol) gave 91 mg (91%) of Example 13M as an off-white oil, and exhibited an $^1$H NMR spectrum consistent with the assigned structure.

Example 13N. D-aspartic acid β-t-butyl ester α-[(R)-1-(3-trifluoromethylphenyl)ethyl]amide N-benzyloxycarbonyl-D-aspartic acid β-t-butyl ester α-[(R)-1-(3-trifluoromethylphenyl)ethyl]amide (217 mg, 0.44 mmol) gave 158 mg (quantitative yield) of Example 13N as an off-white oil, and exhibited an $^1$H NMR spectrum consistent with the assigned structure.

Example 13O. D-aspartic acid β-t-butyl ester α-[N-methyl-N-(3-trifluoromethylbenzyl]amide N-benzyloxycarbonyl-D-aspartic acid β-t-butyl ester α-[N-methyl-N-(3-trifluoromethylbenzyl)]amide (0.282 g, 0.57 mmol) gave 0.195 g (95%) of Example 13O as an off-white oil, and exhibited an $^1$H NMR spectrum consistent with the assigned structure.

Example 13P. D-glutamic acid α-methyl ester γ-(3-trifluoromethyl)benzylamide N-Benzyloxycarbonyl-D-glutamic acid α-methyl ester γ-(3-trifluoromethyl)benzylamide (764 mg, 1.69 mmol) gave g (516 mg, 96%) of Example 13P as an off-white oil, and exhibited an $^1$H NMR spectrum consistent with the assigned structure.

Example 14. General Procedure for Formation of a 2-Azetidinone from an Imine and an Acetyl Chloride Step 1: General procedure for formation of an imine from an amino acid derivative. A solution of 1 equivalent of an α-amino acid ester or amide in dichloromethane is treated sequentially with 1 equivalent of an appropriate aldehyde, and a dessicating agent, such as magnesium sulfate or silica gel, in the amount of about 2 grams of dessicating agent per gram of starting α-amino acid ester or amide. The reaction is stirred at ambient temperature until all of the reactants are consumed as measured by thin layer chromatography. The reactions are typically complete within an hour. The reaction mixture is then filtered, the filter cake is washed with dichloromethane, and the filtrate concentrated under reduced pressure to provide the desired imine that is used as is in the subsequent step.

Step 2: General procedure for the 2+2 cycloaddition of an imine and an acetyl chloride. A dichloromethane solution of the imine (10 mL dichloromethane/1 gram imine) is cooled to 0° C. To this cooled solution is added 1.5 equivalents of an appropriate amine, typically triethylamine, followed by the dropwise addition of a dichloromethane solution of 1.1 equivalents of an appropriate acetyl chloride, such as that described in Example 1 (10 mL dichloromethane/1 gm appropriate acetyl chloride). The reaction mixture is allowed to warm to ambient temperature over 1 h and is then quenched by the addition of a saturated aqueous solution of ammonium chloride. The resulting mixture is partitioned between water and dichloromethane. The layers are separated and the organic layer is washed successively with 1N hydrochloric acid, saturated aqueous sodium bicarbonate, and saturated aqueous sodium chloride. The organic layer is dried over magnesium sulfate and concentrated under reduced pressure. The residue may be used directly for further reactions, or purified by chromatography or by crystallization from an appropriate solvent system if desired. In each case, following the 2+2 reaction, the stereochemistry of the β-lactam may be confirmed by circular dichroism/optical rotary dispersion (CD/ORD). Illustratively, examples of the (αR,3S,4R) and (αS,3S,4R) β-lactam platform stereochemical configurations from prior syntheses may be used as CD/ORD standards.

Example 15. tert-Butyl [3(S)-(4(S)-phenyloxazolidin-2-on-3-yl)-4(R)-(2-styryl)azetidin-2-on-1-yl] acetate Using the procedure of Example 14, the imine prepared from 4.53 g (34.5 mmol) glycine tert-butyl ester and cinnamaldehyde was combined with 2-(4(S)-phenyloxazolidin-2-on-3-yl) acetyl chloride (Example 1) to give 5.5 g (30%) of Example 15 as colorless crystals (recrystallized, n-chlorobutane); mp 194-195° C.

Example 16. General Procedure for Acylation of an Azetidin-2-on-1-ylacetate

A solution of (azetidin-2-on-1-yl)acetate in tetrahydrofuran (0.22 M in azetidinone) is cooled to −78° C. and is with lithium bis(trimethylsilyl)amide (2.2 equivalents). The resulting anion is treated with an appropriate acyl halide (1.1 equivilants). Upon complete conversion of the azetidinone, the reaction is quenched with saturated aqueous ammonium chloride and partitioned between ethyl acetate and water. The organic phase is washed sequentially with 1N hydrochloric acid, saturated aqueous sodium bicarbonate, and saturated aqueous sodium chloride. The resulting organic layer is dried (magnesium sulfate) and evaporated. The residue is purified by silica gel chromatography with an appropriate eluent, such as 3:2 hexane/ethyl acetate.

Example 17. 2,2,2-Trichloroethyl 2(RS)-(tert-butoxycarbonyl)-2-[3(S)-(4(S)-phenyloxazolidin-2-on-3-yl)-4(R)-(2-styryl)azetidin-2-on-1-yl]acetate Using the procedure of Example 16, 9.0 g (20 mmol) of Example 15 was acylated with 4.2 g (20 mmol) of trichloroethylchloroformate to give 7.0 g (56%) of Example 17; mp 176-178° C.

Example 18. 2(RS)-(tert-Butoxycarbonyl)-2-[3(S)-(4(S)-phenyloxazolidin-2-on-3-yl)-4(R)-(2-styryl)azetidin-2-on-1-yl]acetic acid N-(3-trifluoromethylbenzyl)amide A solution of 0.20 g (0.32 mmol) of Example 17 and 52 μL (0.36 mmol) of (3-trifluoromethylbenzyl)amine in THF was heated at reflux. Upon complete conversion (TLC), the solvent was evaporated and the residue was recrystallized (chloroform/hexane) to give 0.17 g (82%) of Example 18 as a white solid; mp 182-184° C.

Example 18A. 2(RS)-(tert-Butoxycarbonyl)-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)amide Example 18A was prepared according to the procedure of Example 18, using 2-fluoro-3-(trifluoromethyl)benzylamine instead of (3-trifluoromethylbenzyl)amine. Example 18A was obtained as a white solid (140 mg, 41%), and exhibited an $^1$H NMR spectrum consistent with the assigned structure.

Examples 19-25AF were prepared according to the procedure of Example 14, where the appropriate amino acid derivative and aldehyde were used in Step 1, and the appropriate acetyl chloride was used in Step 2.

Example 19. 2(S)-(tert-Butoxycarbonylmethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide The imine prepared from 1.52 g (4.39 mmol) of L-aspartic acid β-t-butyl ester α-(3-trifluoromethyl)benzylamide and cinnamaldehyde was combined with 2-(4(S)-phenyloxazolidin-2-on-3-yl) acetyl chloride (Example 1) to give 2.94 g of an orange-brown oil that gave, after flash column chromatography purification (70:30 hexanes/ethyl acetate), 2.06 g (70%) of Example 19 as a white solid; $^1$H NMR (CDCl$_3$) δ 1.39 (s, 9H); 2.46 (dd, J=11.1 Hz, J=16.3 Hz, 1H); 3.18 (dd, J=3.8 Hz, J=16.4 Hz, 1H); 4.12-4.17 (m, 1H); 4.26 (d, J=5.0 Hz, 1H); 4.45 (d, J=6.0 Hz, J=14.9 Hz, 1H); 4.54 (dd, J=5.3 Hz, J=9.8 Hz, 1H); 4.58-4.66 (m, 3H); 4.69-4.75 (m, 1H); 4.81 (dd, J=3.8 Hz, J=11.1 Hz, 1H); 6.25 (dd, J=9.6 Hz, J=15.8 Hz, 1H); 6.70 (d, J=15.8 Hz, 1H); 7.14-7.17 (m, 2H); 7.28-7.46 (m, 11H); 7.62 (s, 1H); 8.27-8.32 (m, 1H).

Example 19A. 2(S)-(tert-Butoxycarbonylmethyl)-2-[3(R)-(4(R)-phenyloxazolidin-2-on-3-yl)-4(S)-(2-styryl)azetidin-2-on-1-yl]acetic acid N-(3-trifluoromethylbenzyl)amide Example 19A was prepared according to the method of Example 19 except that 2-(4(R)-phenyloxazolidin-2-on-3-yl) acetyl chloride (Example 1A) was used instead of 2-(4(S)-phenyloxazolidin-2-on-3-yl) acetyl chloride. Example 19A was obtained as a white solid (41 mg, 13%); $^1$H NMR (CDCl$_3$) δ 1.37 (s, 9H); 3.11 (dd, J=3.7 Hz, J=17.8 Hz, 1H); 3.20 (dd, J=10.6 Hz, J=17.8 Hz, 1H); 4.02 (dd, J=3.7 Hz, J=10.6 Hz, 1H); 4.10-4.17 (m, 1H); 4.24 (d, J=4.9 Hz, 1H); 4.4652-4.574 (dd, J=5.9 Hz, J=15.1 Hz, 1H); 4.58-4.76 (m, 4H); 6.27 (dd, J=9.6 Hz, J=15.8 Hz, 1H); 6.79 (d, J=15.8 Hz, 1H); 7.23-7.53 (m, 13H); 7.63 (s, 1H); 8.51-8.55 (m, 1H).

Example 20. 2(S)-(tert-Butoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide The imine prepared from 3.94 g (10.93 mmol) of L-glutamic acid γ-t-butyl ester α-(3-trifluoromethyl)benzylamide and cinnamaldehyde was combined with 2-(4(S)-phenyloxazolidin-2-on-3-yl) acetyl chloride (Example 1) to give 5.53 g (75%) of Example 20 after flash column chromatography purification (70:30 hexanes/ethyl acetate); $^1$H NMR (CDCl$_3$) δ 1.36 (s, 9H); 1.85-1.96 (m, 1H); 2.18-2.49 (m, 3H); 4.14-4.19 (m, 1H); 4.30 (d, J=4.9 Hz, 2H); 4.44 (dd, J=6.1 Hz, J=14.9 Hz, 1H); 4.56-4.67 (m, 4H); 4.71-4.75 (m, 1H); 6.26 (dd, J=9.6 Hz, J=15.8 Hz, 1H); 6.71 (d, J=15.8 Hz, 1H); 7.16-7.18 (m, 2H); 7.27-7.49 (m, 11H); 7.60 (s, 1H); 8.08-8.12 (m, 1H).

Example 21. 2(S)-(tert-Butoxycarbonylmethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide The imine prepared from 4.20 g (11.6 mmol) of L-aspartic acid β-t-butyl ester α-[4-(2-phenylethyl)]piperazinamide and cinnamaldehyde was combined with 2-(4(S)-phenyloxazolidin-2-on-3-yl) acetyl chloride (Example 1) to give 4.37 g (55%) of Example 21 after flash column chromatography purification (50:50 hexanes/ethyl acetate); $^1$H NMR (CDCl$_3$) δ 1.34 (s, 9H); 2.26-2.32 (m, 1H); 2.46-2.63 (m, 4H); 2.75-2.89 (m, 4H); 3.24-3.32 (m, 1H); 3.49-3.76 (m, 3H); 4.07-4.13 (m, 1H); 4.30 (d, J=4.6 Hz, 1H); 4.22-4.48 (m, 1H); 4.55-4.61 (m, 1H); 4.69-4.75 (m, 1H); 5.04-5.09 (m, 1H); 6.15 (dd, J=9.3 Hz, J=15.9 Hz, 1H); 6.63 (d, J=15.8 Hz, 1H); 7.18-7.42 (m, 15H).

Example 22. 2(S)-(tert-Butoxycarbonylethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide The imine prepared from 2.54 g (6.75 mmol) of L-glutamic acid γ-t-butyl ester α-[4-(2-phenylethyl)]piperazinamide and cinnamaldehyde was combined with 2-(4(S)-phenyloxazolidin-2-on-3-yl) acetyl chloride (Example 1) to give 3.55 g (76%) of Example 22 after flash column chromatography purification (50:50 hexanes/ethyl acetate); $^1$H NMR (CDCl$_3$) δ 1.32 (s, 9H); 1.96-2.07 (m, 1H); 2.15-2.44 (m, 6H); 2.54-2.62 (m, 2H); 2.69-2.81 (m, 3H); 3.28-3.34 (m, 1H); 3.59-3.68 (m, 1H); 4.08-4.13 (m, 1H); 4.33-4.44 (m, 2H); 4.48-4.60 (m, 2H); 4.67-4.77 (m, 1H); 6.14 (dd, J=8.9 Hz, J=16.0 Hz, 1H); 6.62 (d, J=16.0 Hz, 1H); 7.16-7.42 (m, 15H).

Example 23. 2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide The imine prepared from 0.973 g (2.81 mmol) of D-aspartic acid β-t-butyl ester α-(3-trifluoromethyl)benzylamide and cinnamaldehyde was combined with 2-(4(S)-phenyloxazolidin-2-on-3-yl) acetyl chloride (Example 1) to give 1.53 g (82%) of Example 23 after flash column chromatography purification (70:30 hexanes/ethyl acetate); $^1$H NMR (CDCl$_3$) δ 1.37 (s, 9H); 3.10 (dd, J=3.7 Hz, J=17.8 Hz, 1H); 3.20 (dd, J=10.7 Hz, J=17.8 Hz, 1H); 4.02 (dd, J=3.6 Hz, J=10.6 Hz, 1H); 4.11-4.17 (m, 1H); 4.24 (d, J=4.9 Hz, 1H); 4.46 (dd, J=5.8 Hz, J=15.1 Hz, 1H); 4.58-4.67 (m, 3H); 4.70-4.76 (m, 1H); 6.27 (dd, J=9.5 Hz, J=15.8 Hz, 1H); 6.79 (d, J=15.8 Hz, 1H); 7.25-7.50 (m, 13H); 7.63 (s, 1H); 8.50-8.54 (m, 1H).

Example 23A. 2(R)-(tert-Butoxycarbonylmethyl)-2-[3(R)-(4(R)-phenyloxazolidin-2-on-3-yl)-4(S)-(2-styryl)azetidin-2-on-1-yl]acetic acid N-(3-trifluoromethylbenzyl)amide Example 23A was prepared according to the method of Example 23 except that 2-(4(R)-phenyloxazolidin-2-on-3-yl) acetyl chloride (Example 1A) was used instead of 2-(4(S)-phenyloxazolidin-2-on-3-yl) acetyl chloride. Example 23A was obtained as a white solid (588 mg, 49%); $^1$H NMR (CDCl$_3$) δ 1.39 (s, 9H); 2.47 (dd, J=11.2 Hz, J=16.3 Hz, 1H); 3.18 (dd, J=3.8 Hz, J=16.3 Hz, 1H); 4.15 (t, J=8.25, Hz 1H); 4.26 (d, J=5.0 Hz, 1H); 4.45 (dd, J=6.0 Hz, J=15.0 Hz, 1H); 4.52-4.57 (m, 3H); 4.63 (t, J=9 Hz, 1H); 4.70 (t, J=8 Hz, 1H); 4.81 (dd, J=3.8 Hz, J=10.8 Hz, 1H); 6.25 (dd, J=9.8 Hz, J=15.8 Hz, 1H); 6.70 (d, J=15.8 Hz, 1H); 7.15-7.17 (m, 2H); 7.27-7.51 (m, 11H); 7.62 (s, 1H); 8.27-8.32 (m, 1H).

Example 24. 2(R)-(tert-Butoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide The imine prepared from 1.15 g (3.20 mmol) of D-glutamic acid β-butyl ester α-(3-trifluoromethyl)benzylamide and cinnamaldehyde was combined with 2-(4(S)-phenyloxazolidin-2-on-3-yl) acetyl chloride (Example 1) to give 1.84 g (85%) of Example 24 after flash column chromatography purification (70:30 hexanes/ethyl acetate); $^1$H NMR (CDCl$_3$) δ 1.37 (s, 9H); 2.23-2.39 (m, 4H); 3.71-3.75 (m, 1H); 4.13-4.18 (m, 1H); 4.31 (d, J=4.9 Hz, 1H); 4.44-4.51 (m, 2H); 4.56-4.68 (m, 2H); 4.71-4.76 (m, 1H); 6.26 (dd, J=9.5 Hz, J=15.8 Hz, 1H); 6.71 (d, J=15.8 Hz, 1H); 7.25-7.52 (m, 13H); 7.63 (s, 1H); 8.25-8.30 (m, 1H).

Example 25. 2(S)-(tert-Butoxycarbonylethyl)-2-[3(S)-(4(S)-phenyloxazolidin-2-on-3-yl)-4(R)-(2-styryl)azetidin-2-on-1-yl]acetic acid N-(4-cyclohexyl)piperazinamide The imine prepared from 2.58 g (5.94 mmol) of L-glutamic acid γ-butyl ester α-(4-cyclohexyl)piperazinamide and cinnamaldehyde was combined with 2-(4(S)-phenyloxazolidin-2-on-3-yl) acetyl chloride (Example 1) to give 3.27 g (94%) of Example 25 after flash column chromatography purification (95:5 dichloromethane/methanol); $^1$H NMR (CDCl$_3$) δ 1.32 (s, 9H); 1.10-1.18 (m, 1H); 1.20-1.31 (m, 2H); 1.38-1.45 (m, 2H); 1.61-1.66 (m, 1H); 1.84-1.89 (m, 2H); 1.95-2.01 (m, 2H); 2.04-2.14 (m, 3H); 2.20-2.24 (m, 1H); 2.29-2.35 (m, 1H); 2.85-2.92 (m, 1H); 3.24-3.32 (m, 1H); 3.36-3.45 (m, 2H); 3.80-3.86 (m, 1H); 4.08 (t, J=8.3 Hz, 1H); 4.27 (d, J=5.0 Hz, 1H); 4.31-4.55 (m, 4H); 4.71 (t, J=8.3 Hz, 1H); 4.83-4.90 (m, 1H); 6.18 (dd, J=9.1 Hz, J=15.9 Hz, 1H); 6.67 (d, J=15.9 Hz, 1H); 7.25-7.44 (m, 10H); 8.22 (brs, 1H).

Example 25A. tert-Butyl 2(S)-(2-(4-cyclohexylpiperazinylcarbonyl)ethyl)-2-[3(S)-(4(S)-phenyloxazolidin-2-on-3-yl)-4(R)-(2-styryl)azetidin-2-on-1-yl]acetate The imine prepared from 1.282 g (3.63 mmol) of L-glutamic acid α-t-butyl ester γ-(4-cyclohexyl)piperazinamide and cinnamaldehyde was combined with 2-(4(S)-phenyloxazolidin-2-on-3-yl) acetyl chloride (Example 1) to give 1.946 g (80%) of Example 25A after flash column chromatography purification (50:50 hexanes/ethyl acetate); $^1$H NMR (CDCl$_3$) δ 1.15-1.26 (m, 6H); 1.39 (s, 9H); 1.55-1.64 (m, 2H); 1.77-1.83 (m, 3H); 2.22-2.35 (m, 2H); 2.40-2.50 (m, 6H); 2.75-2.79 (m, 1H); 3.43-3.48 (m, 1H); 3.56-3.60 (m, 2H); 3.75-3.79 (m, 1H); 4.10 (t, J=8.3 Hz, 1H); 4.31-4.35 (m, 2H); 4.58 (t, J=8.8 Hz, 1H); 4.73 (t, J=8.4 Hz, 1H); 6.17 (dd, J=8.6 Hz, J=16.0 Hz, 1H); 6.65 (d, J=16.0 Hz, 1H); 7.27-7.42 (m, 10H).

Example 25B. 2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)amide The imine prepared from 0.256 g (0.70 mmol) of D-aspartic acid β-t-butyl ester α-(2-fluoro-3-trifluoromethyl)benzylamide and cinnamaldehyde was combined with 2-(4(S)-phenyloxazolidin-2-on-3-yl) acetyl chloride (Example 1) to give 0.287 g (60%) of Example 25B after flash column chromatography purification (70:30 hexanes/ethyl acetate); $^1$H NMR (CDCl$_3$) δ 1.38 (s, 9H); 3.12 (dd, J=4.0 Hz, J=17.8 Hz, 1H); 3.20 (dd, J=10.4 Hz, J=17.8 Hz, 1H); 4.05 (dd, J=3.9 Hz, J=10.4 Hz, 1H); 4.14 (dd, J=J'=8.2 Hz, 1H); 4.25 (d, J=4.9 Hz, 1H); 4.59-4.67 (m, 4H); 4.74 (t, J=8.3 Hz, 1H); 6.36 (dd, J=9.6 Hz, J=15.8 Hz, 1H); 6.83 (d, J=15.8 Hz, 1H); 7.02-7.07 (m, 1H); 7.28-7.55 (m, 12H); 8.44-8.48 (m, 1H).

Example 25C. 2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N—[(S)-α-methylbenzyl]amide The imine prepared from 0.167 g (0.57 mmol) of D-aspartic acid β-t-butyl ester [(S)-α-methylbenzyl]amide and cinnamaldehyde was combined with 2-(4(S)-phenyloxazolidin-2-on-3-yl) acetyl chloride (Example 1) to give 0.219 g (63%) of Example 25C after flash column chromatography purification (70:30 hexanes/ethyl acetate); $^1$H NMR (CDCl$_3$) δ 1.35 (s, 9H); 1.56 (d, J=7.0 Hz, 3H); 2.97 (dd, J=3.5 Hz, J=18.0 Hz, 1H); 3.15 (dd, J=11.0 Hz, J=17.5 Hz, 1H); 4.01 (dd, J=3.0 Hz, J=11.0 Hz, 1H); 4.14 (t, J=8.5 Hz, 1H); 4.24 (d, J=5.0 Hz, 1H); 4.57 (dd, J=5.0 Hz, J=9.5 Hz, 1H); 4.64 (t, J=8.8 Hz, 1H); 5.07 (t, J=8.5 Hz, 1H); 5.03-5.09 (m, 1H); 6.43 (dd, J=9.5 Hz, J=16.0 Hz, 1H); 6.83 (d, J=16.0 Hz, 1H); 7.16-7.20 (m, 1H); 7.27-7.49 (m, 14H); 8.07-8.10 (m, 1H).

Example 25D. 2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N—[(R)-α-methylbenzyl]amide The imine prepared from 0.187 g (0.46 mmol) of D-aspartic acid β-t-butyl ester [(R)-α-methylbenzyl]amide and cinnamaldehyde was combined with 2-(4(S)-phenyloxazolidin-2-on-3-yl) acetyl chloride (Example 1) to give 0.25 g (64%) of Example 25D after flash column chromatography purification (70:30 hexanes/ethyl acetate); $^1$H NMR (CDCl$_3$) δ 1.36 (s, 9H); 1.59 (d, J=7.1 Hz, 3H); 3.10 (dd, J=3.5 Hz, J=17.8 Hz, 1H); 3.22 (dd, J=10.9 Hz, J=17.8 Hz, 1H); 3.93 (dd, J=3.5 Hz, J=10.8 Hz, 1H); 4.14 (t, J=8.1 Hz, 1H); 4.24 (d, J=5.0 Hz, 1H); 4.58 (dd, J=5.0 Hz, J=9.5 Hz, 1H); 4.65 (t, J=8.7 Hz, 1H); 4.74 (t, J=8.2 Hz, 1H); 5.06-5.14 (m, 1H); 6.32 (dd, J=9.5 Hz, J=15.8 Hz, 1H); 6.74 (d, J=15.8 Hz, 1H); 7.19-7.43 (m, 15H); 8.15-8.18 (m, 1H).

Example 25E. 2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide The imine prepared from 0.195 g (0.41 mmol) of D-aspartic acid β-t-butyl ester α-[N-methyl-N-(3-trifluoromethylbenzyl)]amide and cinnamaldehyde was combined with 2-(4(S)-phenyloxazolidin-2-on-3-yl) acetyl chloride (Example 1) to give 0.253 g (69%) of Example 25E after flash column chromatography purification (70:30 hexanes/ethyl acetate); $^1$H NMR (CDCl$_3$) δ 1.36 (s, 9H); 2.53 (dd, J=4.0 Hz, J=17.0 Hz, 1H); 3.06 (dd, J=10.8 Hz, J=16.8 Hz, 1H); 3.13 (s, 3H); 4.12 (dd, J=8.0 Hz, J=9.0 Hz, 1H); 4.26 (d, J=5.0 Hz, 1H); 4.38 (d, J=15.0 Hz, 1H); 4.46 (dd, J=5.0 Hz, J=9.5 Hz, 1H); 4.56 (t, J=6.8 Hz, 1H); 4.70-4.79 (m, 2H); 5.27 (dd, J=4.0 Hz, J=11.0 Hz, 1H); 6.22 (dd, J=9.3 Hz, J=15.8 Hz, 1H); 6.73 (d, J=15.8 Hz, 1H); 7.33-7.45 (m, 14H).

Example 25F. 2(S)-(tert-Butoxycarbonylethyl)-2-[3(S)-(4(S)-phenyloxazolidin-2-on-3-yl)-4(R)-(2-chlorostyr-2-yl)azetidin-2-on-1-yl]acetic acid N-(3-trifluoromethylbenzyl)amide The imine prepared from 1.62 g (4.44 mmol) of L-glutamic acid γ-t-butyl ester α-(3-trifluoromethyl)benzylamide and α-chlorocinnamaldehyde was combined with 2-(4(S)-phenyloxazolidin-2-on-3-yl) acetyl chloride (Example 1) to give 0.708 g (22%) of Example 25F after flash column chromatography purification (70:30 hexanes/ethyl acetate); $^1$H NMR (CDCl$_3$) δ 1.35 (s, 9H); 1.68 (brs, 1H); 2.19-2.35 (m, 2H); 2.40-2.61 (m, 2H); 4.13 (dd, J=7.5 Hz, J=9.0 Hz, 1H); 4.22 (t, J=7.0 Hz, 1H); 4.34 (d, J=4.5 Hz, 1H); 4.45 (dd, J=5.5 Hz, J=15.0 Hz, 1H); 4.51-4.60 (m, 3H); 4.89 (dd, J=7.5 Hz, J=8.5 Hz, 1H); 6.89 (s, 1H); 7.28-7.54 (m, 14H).

Example 25G. 2(R)-(tert-Butoxycarbonylmethyl)-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide The imine prepared from 0.34 g (0.98 mmol) of D-aspartic acid β-t-butyl ester α-(3-trifluoromethylbenzyl)amide and 2'-methoxycinnamaldehyde was combined with 2-(4(S)-phenyloxazolidin-2-on-3-yl) acetyl chloride (Example 1) to give 0.402 g (59%) of Example 25G after flash column chromatography purification (70:30 hexanes/ethyl acetate); $^1$H NMR (CDCl$_3$) δ 1.35 (s, 9H); 1.68 (brs, 1H); 2.19-2.35 (m, 2H); 2.40-2.61 (m, 2H); 4.13 (dd, J=7.5 Hz, J=9.0 Hz, 1H); 4.22 (t, J=7.0 Hz, 1H); 4.34 (d, J=4.5 Hz, 1H); 4.45 (dd, J=5.5 Hz, J=15.0 Hz, 1H); 4.51-4.60 (m, 3H); 4.89 (dd, J=7.5 Hz, J=8.5 Hz, 1H); 6.89 (s, 1H); 7.28-7.54 (m, 14H).

Example 25H. tert-Butyl (2R)-(Benzyloxymethyl)-2-[3(S)-(4(S)-phenyloxazolidin-2-on-3-yl)-4(R)-(2-styryl)azetidin-2-on-1-yl]acetate The imine prepared from 0.329 g (1.31 mmol) of O-(benzyl)-D-serine t-butyl ester (Example 5B) and cinnamaldehyde was combined with 2-(4(S)-phenyloxazolidin-2-on-3-yl) acetyl chloride (Example 1) to give 0.543 g (73%) of Example 25H after flash column chromatography purification (90:10 hexanes/ethyl acetate); $^1$H NMR (CDCl$_3$) δ 1.39 (s, 9H); 3.56 (dd, J=2.7 Hz, J=9.5 Hz, 1H); 3.82 (dd, J=4.8 Hz, J=9.5 Hz, 1H); 4.11 (t, J=8.3 Hz, 1H); 4.21-4.29 (m, 2H); 4.50-4.58 (m, 3H); 4.71-4.78 (m, 2H); 6.19 (dd, J=9.1 Hz, J=16.0 Hz, 1H); 6.49 (d, J=16.0 Hz, 1H); 7.07-7.11 (m, 1H); 7.19-7.40 (m, 14H).

Example 25I. tert-Butyl 2(S)-(2-(4-cyclohexylpiperazinylcarbonyl)methyl)-2-[3(S)-(4(S)-phenyloxazolidin-2-on-3-yl)-4(R)-(2-styryl)azetidin-2-on-1-yl]acetate The imine prepared from 0.3 g (0.88 mmol) of L-aspartic acid α-t-butyl ester γ-(4-cyclohexyl)piperazinamide and cinnamaldehyde was combined with 2-(4(S)-phenyloxazolidin-2-on-3-yl) acetyl chloride (Example 1) to give 464 mg (80%) of Example 25I as a white solid after flash column chromatography purification (50:50 hexanes/ethyl acetate). Example 25I exhibited an $^1$H NMR spectrum consistent with the assigned structure.

Example 25J. tert-Butyl 3(R)-[3(S)-(4(S)-phenyloxazolidin-2-on-3-yl)-3-methyl-4(R)-(styr-2-yl)azetidin-2-on-1-yl]-3-[(3-trifluoromethyl)phenylmethylaminocarbonyl]propanoate The imine prepared from 0.307 g (0.89 mmol) of D-aspartic acid β-t-butyl ester α-(3-trifluoromethyl)benzylamide (Example 20) and cinnamaldehyde was combined with 2-(4(S)-phenyloxazolidin-2-on-3-yl)propanoyl chloride (Example 1E) to give 120 mg (20%) after flash column chromatography purification (hexanes 70%/EtOAc 30%); $^1$H NMR (CDCl$_3$) δ1.25 (s, 3H), 1.38 (s, 9H); 3.09 (dd, J=3.0 Hz, J=18.0 Hz, 1H); 3.33 (dd, J=12.5 Hz, J=18.0 Hz, 1H); 4.01 (dd, J=3.0 Hz, J=11.5 Hz, 1H); 4.04 (dd, J=3.5 Hz, J=8.8 Hz, 1H); 4.42 (d, J=9.0 Hz, 1H); 4.45-4.51 (m, 3H); 4.61-4.66 (m, 1H); 4.75 (dd, J=3.5 Hz, J=8.5 Hz, 1H); 6.23 (dd, J=9.0 Hz, J=15.5 Hz, 1H); 6.78 (d, J=15.5 Hz, 1H); 7.23-7.53 (m, 13H); 7.64 (s, 1H).

Example 25K. 2(R)-(tert-Butoxycarbonylmethyl)-2-[3(S)-(4(S)-phenyloxazolidin-2-on-3-yl)-4(R)-(prop-1-enyl)azetidin-2-on-1-yl]acetic acid N-(3-trifluoromethylbenzyl)amide The imine prepared from 0.289 g (0.83 mmol) of D-aspartic acid β-t-butyl ester α-(3-trifluoromethyl)benzylamide and crotonaldehyde was combined with 2-(4(S)-phenyloxazolidin-2-on-3-yl) acetyl chloride (Example 1) to give 381 mg (76%) of Example 25K after flash column chromatography purification (99:1 CH$_2$Cl$_2$/MeOH); $^1$H NMR (CDCl$_3$) δ 1.36 (s, 9H), 1.69 (dd, J=2 Hz, J=6.5 Hz, 3H); 3.08 (dd, J=3.3 Hz, J=17.8 Hz, 1H); 3.18 (dd, J=11 Hz, J=17.5 Hz, 1H); 3.94 (dd. J=3.5 Hz, J=11 Hz, 1H); 4.12 (d, J=5 Hz, 1H); 4.15 (dd, J=7 Hz, J=8 Hz, 1H); 4.35 (dd, J=4.8 Hz, J=9.8 Hz, 1H); 4.44 (dd, J=6 Hz, J=15 Hz, 1H); 4.61 (dd, J=6 Hz, J=15

Hz, 1H); 4.67-4.75 (m, 2H); 5.52-5.58 (m, 1H); 5.92-6.00 (m, 1H); 7.33-7.60 (m, 9H); 8.47-8.50 (m, 1H).

Example 25O. Methyl 2(S)-(tert-Butoxycarbonyl-ethyl)-2-[3(S)-(4(S)-phenyloxazolidin-2-on-3-yl)-4(R)-(2-styryl)azetidin-2-on-1-yl]acetate The imine prepared from 433 mg (1.99 mmol) of L-glutamic acid β-butyl ester α-methyl ester and cinnamaldehyde was combined with 2-(4(S)-phenyloxazolidin-2-on-3-yl) acetyl chloride (Example 1) to give 682 mg (64%) of Example 25O after flash column chromatography purification (70:30 hexanes/ethyl acetate); $^{1}$H NMR (CDCl$_3$) δ 1.32 (s, 9H); 2.10-2.26 (m, 1H); 2.30-2.41 (m, 3H); 3.66 (s, 3H); 3.95-3.99 (m, 1H); 4.16 (dd, J=7.5 Hz, J=9 Hz, 1H); 4.38 (dd, J=5 Hz, J=9 Hz, 1H); 4.55 (d, J=5 Hz 1H); 4.61 (t, J=9 Hz, 1H); 4.86 (dd, J=7.5 Hz, J=9 Hz, 1H); 6.00 (dd, J=9 Hz, J=16 Hz, 1H); 6.60 (d, J=16 Hz, 1H); 7.26-7.43 (m, 10H).

Example 25M. tert-Butyl 2(S)-(methoxycarbonyl-ethyl)-2-[3(S)-(4(S)-phenyloxazolidin-2-on-3-yl)-4(R)-(2-styryl)azetidin-2-on-1-yl]acetate The imine prepared from 428 mg (1.97 mmol) of L-glutamic acid β-butyl ester α-methyl ester and cinnamaldehyde was combined with 2-(4(S)-phenyloxazolidin-2-on-3-yl) acetyl chloride (Example 1) to give 864 mg (82%) of Example 25M after flash column chromatography purification (70:30 hexanes/ethyl acetate); $^{1}$H NMR (CDCl$_3$) δ 1.40 (s, 9H); 2.12-2.27 (m, 1H); 2.32-2.55 (m, 3H); 3.50 (s, 3H); 3.72 (dd, J=4.6 Hz, J=10.4 Hz, 1H); 4.12-4.17 (m, 1H); 4.34 (dd, J=5 Hz, J=9 Hz, 1H); 4.50 (d, J=5 Hz, 1H); 4.60 (t, J=8.9 Hz, 1H); 4.81-4.86 (m, 1H); 6.06 (dd, J=9 Hz, J=16 Hz, 1H); 6.59 (d, J=16 Hz, 1H); 7.25-7.42 (m, 10H).

Example 25P. Methyl 2(S)-(tert-Butoxycarbonylm-ethyl)-2-[3(S)-(4(S)-phenyloxazolidin-2-on-3-yl)-4(R)-(2-styryl)azetidin-2-on-1-yl]acetate The imine prepared from 424 mg (2.09 mmol) of L-aspartic acid γ-t-butyl ester α-methyl ester and cinnamaldehyde was combined with 2-(4(S)-phenyloxazolidin-2-on-3-yl) acetyl chloride (Example 1) to give 923 mg (85%) of Example 25P after after recrystallization from CH$_2$Cl$_2$/hexanes; $^{1}$H NMR (CDCl$_3$) δ 1.41 (s, 9H); 2.77 (dd, J=7.5 Hz, J=16.5 Hz, 1H); 3.00 (dd, J=7 Hz, J=16.5 Hz, 1H); 4.16 (dd, J=7.5 Hz, J=9 Hz, 1H); 4.41-48 (m, 2H); 4.55 (d, J=5 Hz, 1H); 4.60 (t, J=8.8 Hz, 1H); 4.86 (dd, J=7.5 Hz, J=9 Hz, 1H); 5.93 (dd, J=9.5 Hz, J=15.5 Hz, 1H); 6.61 (d, J=15.5 Hz, 1H); 7.25-7.43 (m, 10H).

Example 25L. 2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N—[(R)-1-(3-trifluoromethylpheny)ethyl]amide The imine prepared from 160 mg (0.44 mmol) of D-aspartic acid β-t-butyl ester α-[(R)-1-(3-trifluoromethyl-pheny)ethyl]amide and cinnamaldehyde was combined with 2-(4(S)-phenyloxazolidin-2-on-3-yl) acetyl chloride (Example 1) to give 166 mg (55%) of Example 25L after flash column chromatography purification (70:30 hexanes/EtOAc). Example 25L exhibited an $^{1}$H NMR spectrum consistent with the assigned structure.

Example 25N. 2(R)-(tert-Butoxycarbonylmethyl)-2-[3(S)-(4(S)-phenyloxazolidin-2-on-3-yl)-4(R)-(2-styryl)azetidin-2-on-1-yl]acetic acid N—[(S)-1-(3-trifluoromethylpheny)ethyl]amide The imine prepared from 120 mg (0.22 mmol) of D-aspartic acid β-t-butyl ester α-[(S)-1-(3-trifluoromethylpheny)ethyl]amide and cinnamaldehyde was combined with 2-(4(S)-phenyloxazolidin-2-on-3-yl) acetyl chloride (Example 1) to give 75 mg (50%) of Example 25N after flash column chromatography purification (70:30 hexanes/EtOAc). Example 25N exhibited an $^{1}$H NMR spectrum consistent with the assigned structure.

Example 25Q. Methyl 2(R)-(2-(3-trifluoromethyl-benzyl)aminocarbonyl)ethyl)-2-[3(S)-(4(S)-pheny-loxazolidin-2-on-3-yl)-4(R)-(2-styryl)azetidin-2-on-1-yl]acetate The imine prepared from 517 mg (1.62 mmol) of D-glutamic acid α-methyl ester γ-(3-trifluoromethyl)benzylamide and cinnamaldehyde was combined with 2-(4(S)-phenyloxazolidin-2-on-3-yl) acetyl chloride (Example 1) to give 527 mg (51%) of Example 25Q after flash column chromatography purification (50:50 hexanes/EtOAc). Example 25Q exhibited an $^{1}$H NMR spectrum consistent with the assigned structure.

The following compounds were prepared according to the processes described herein:

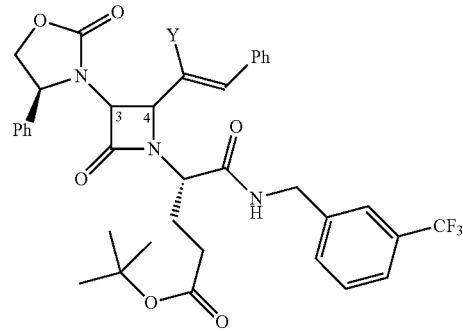

| Example | Y | C(3)-C(4) Stereochemistry |
|---------|---|---------------------------|
| 25R | F | (3S,4R) |
| 25S | F | not determined |
| 25T | Br | not determined |
| 25U | Br | not determined |

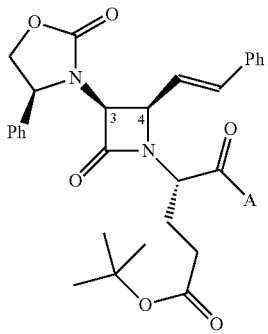

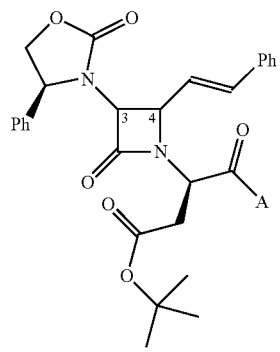

| Example | A |
|---|---|
| 25V | (R)-1,2,3,4-tetrahydro-1-naphtylamide |
| 25W | 1-phenyl-cyclopentylamide |

| Example | C(3)-C(4) Stereochemistry | A | A' |
|---|---|---|---|
| 25AB | (3S,4R) | α,α-dimethylbenzylamino | t-butyl ester |
| 25AC | not determined | N-methyl-3-CF3-benzylamino | t-butyl ester |
| 25AD | not determined | (R)-α-methylbenzylamino | t-butyl ester |
| 25AE | (3S,4R) | (R)-α,N-dimethylbenzylamino | t-butyl ester |

Example 25AF t-Butyl 2(S)-(2-(3-trifluoromethyl-benzyl)aminocarbonyl)ethyl)-2-[3(S)-(4(S)-phenyloxazolidin-2-on-3-yl)-4(R)-(2-styryl)azetidin-2-on-1-yl]acetate Example 26. General Procedure for Hydrolysis of a Tert-Butyl Ester A solution of tert-butyl ester derivative in formic acid, typically 1 g in 10 mL, is stirred at ambient temperature until no more ester is detected by thin layer chromatography (dichloromethane 95%/methanol 5%), a typical reaction time being around 3 hours. The formic acid is evaporated under reduced pressure; the resulting solid residue is partitioned between dichloromethane and saturated aqueous sodium bicarbonate. The organic layer is evaporated to give an off-white solid that may be used directly for further reactions, or recrystallized from an appropriate solvent system if desired.

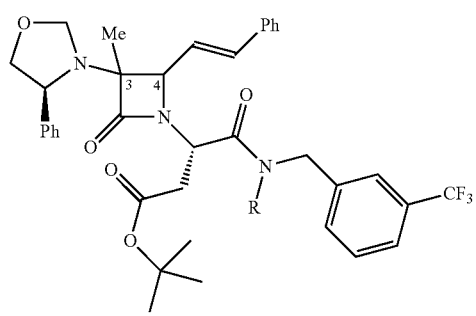

| Example | C(3)-C(4) Stereochemistry | R |
|---|---|---|
| 25X | (3S)-cis | Me |
| 25Y | not determined | H |

Examples 27-34AE were prepared from the appropriate tert-butyl ester according to the procedure used in Example 26.

Example 27. 2(R,S)-(Carboxy)-2-[3(S)-(4(S)-phenyloxazolidin-2-on-3-yl)-4(R)-(2-styryl)azetidin-2-on-1-yl]acetic acid N-(3-trifluoromethylbenzyl)amide Example 18 (0.30 g, 0.46 mmol) was hydrolyzed to give 0.27 g (quantitative yield) of Example 27 as an off-white solid; $^1$H NMR (CDCl$_3$) δ 4.17-5.28 (m, 9H); 6.21-6.29 (m, 1H), 6.68-6.82 (m, 1H); 7.05-7.75 (m, 13H); 9.12-9.18 (m, 1H).

| Example | A |
|---|---|
| 25Z | 1-phenyl-cyclopent-1-ylamino |
| 25AA | (R)-1-phenylethy-1-amino |

Example 28. 2(S)-(Carboxymethyl)-2-[3(S)-(4(S)-phenyloxazolidin-2-on-3-yl)-4(R)-(2-styryl)azetidin-2-on-1-yl]acetic acid N-(3-trifluoromethylbenzyl) amide Example 19 (1.72 g, 2.59 mmol) was hydrolyzed to give 1.57 g (quantitative yield) of Example 28 as an off-white solid; $^1$H NMR (CDCl$_3$) δ 2.61 (dd, J=9.3 Hz, J=16.6 Hz, 1H); 3.09-3.14 (m, 1H); 4.10-4.13 (m, 1H); 4.30 (d, J=4.5 Hz, 1H); 4.39-4.85 (m, 6H); 6.20 (dd, J=9.6 Hz, J=15.7 Hz, 1H); 6.69 (d, J=15.8 Hz, 1H); 7.12-7.15 (m, 2H); 7.26-7.50 (m, 11H); 7.61 (s, 1H); 8.41-8.45 (m, 1H).

Example 28A. 2(S)-(Carboxymethyl)-2-[3(R)-(4(R)-phenyloxazolidin-2-on-3-yl)-4(S)-(2-styryl)azetidin-2-on-1-yl]acetic acid N-(3-trifluoromethylbenzyl) amide Example 19A (41 mg, 0.06 mmol) was hydrolyzed to give 38 mg (quantitative yield) of Example 28A as an off-white solid; $^1$H NMR (CDCl$_3$) δ 2.26 (d, J=7 Hz, 1H); 4.03 (t, J=7 Hz, 1H); 4.16 (t, J=8 Hz, 1H); 4.26 (d, J=4.3 Hz, 1H); 4.46 (dd, J=5.7 Hz, J=15.1 Hz, 1H); 4.53-4.75 (m, 5H); 6.25 (dd. J=9.5 Hz, J=15.7 Hz, 1H); 6.77 (d, J=15.7 Hz, 1H); 7.28-7.53 (m, 13H); 7.64 (s, 1H); 8.65-8.69 (m, 1H).

Example 29. 2(S)-(Carboxyethyl)-2-[3(S)-(4(S)-phenyloxazolidin-2-on-3-yl)-4(R)-(2-styryl)azetidin-2-on-1-yl]acetic acid N-(3-trifluoromethylbenzyl) amide Example 20 (4.97 g, 7.34 mmol) was hydrolyzed to give 4.43 g (97%) of Example 29 as an off-white solid; $^1$H NMR (CDCl$_3$) δ 1.92-2.03 (m, 1H); 2.37-2.51 (m, 3H); 4.13-4.19 (m, 1H); 3.32 (d, J=4.9 Hz, 1H); 4.35-4.39 (m, 1H); 4.44 (dd, J=5.9 Hz, J=14.9 Hz, 1H); 4.50-4.57 (m, 2H); 4.61-4.67 (m, 1H); 4.70-4.76 (m, 1H); 6.24 (dd, J=9.6 Hz, J=15.8 Hz, 1H); 6.70 (d, J=15.8 Hz, 1H); 7.18-7.47 (m, 14H).

Example 30. 2(S)-(Carboxymethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide Example 21 (1.88 g, 2.78 mmol) was hydrolyzed to give 1.02 g (60%) of Example 30 as an off-white solid; $^1$H NMR (CDCl$_3$) δ 2.63 (dd, J=6.0 Hz, J=16.5 Hz, 1H); 2.75-2.85 (m, 1H); 3.00 (dd, J=8.2 Hz, J=16.6 Hz, 1H); 3.13-3.26 (m, 4H); 3.37-3.56 (m, 4H); 3.86-4.00 (m, 1H); 4.05-4.11 (m, 1H); 4.24 (d, J=5.0 Hz, 1H); 4.46-4.66 (m, 1H); 4.65-4.70 (m, 1H); 5.10-5.15 (m, 1H); 6.14 (dd, J=9.3 Hz, J=15.9 Hz, 1H); 6.71 (d, J=15.9 Hz, 1H); 7.22-7.41 (m, 15H); 12.02 (s, 1H).

Example 31. 2(S)-(Carboxyethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide Example 22 (0.383 g, 0.55 mmol) was hydrolyzed to give 0.352 g (quantitative yield) of Example 31 as an off-white solid; $^1$H NMR (CDCl$_3$) δ 1.93-2.01 (m, 1H); 2.07-2.36 (m, 6H); 2.82-2.90 (m, 1H); 3.00-3.20 (m, 4H); 3.36-3.54 (m, 4H); 3.74-3.82 (m, 1H); 4.06-4.11 (m, 1H); 4.29 (d, J=4.9 Hz, 1H); 4.33-4.46 (m, 2H); 4.50-4.58 (m, 2H); 4.67-4.72 (m, 1H); 4.95-5.00 (m, 1H); 6.18 (dd, J=9.2 Hz, J=16.0 Hz, 1H); 6.67 (d, J=15.9 Hz, 1H); 7.19-7.42 (m, 15H); 8.80 (brs, 1H).

Example 32. 2(R)-(Carboxymethyl)-2-[3(S)-(4(S)-phenyloxazolidin-2-on-3-yl)-4(R)-(2-styryl)azetidin-2-on-1-yl]acetic acid N-(3-trifluoromethylbenzyl) amide Example 23 (1.51 g, 2.27 mmol) was hydrolyzed to give 1.38 g (quantitative yield) of Example 32 as an off-white solid.

Example 32A. 2(R)-(Carboxymethyl)-2-[3(R)-(4(R)-phenyloxazolidin-2-on-3-yl)-4(S)-(2-styryl)azetidin-2-on-1-yl]acetic acid N-(3-trifluoromethylbenzyl)amide Example 23A (550 mg, 0.83 mmol) was hydrolyzed to give 479 mg (95%) of Example 32A as an off-white solid. Example 32A exhibited an $^1$H NMR spectrum consistent with the assigned structure.

Example 33. 2(R)-(Carboxyethyl)-2-[3(S)-(4(S)-phenyloxazolidin-2-on-3-yl)-4(R)-(2-styryl)azetidin-2-on-1-yl]acetic acid N-(3-trifluoromethylbenzyl) amide Example 24 (0.604 g, 0.89 mmol) was hydrolyzed to give 0.554 g (quantitative yield) of Example 33 as an off-white solid.

Example 34. 2(S)-(Carboxyethyl)-2-[3(S)-(4(S)-phenyloxazolidin-2-on-3-yl)-4(R)-(2-styryl)azetidin-2-on-1-yl]acetic acid N-(4-cyclohexyl)piperazinamide Example 25 (0.537 g, 0.80 mmol) was hydrolyzed to give 0.492 g (quantitative yield) of Example 34 as an off-white solid; $^1$H NMR (CDCl$_3$) δ 1.09-1.17 (m, 1H); 1.22-1.33 (m, 2H); 1.40-1.47 (m, 2H); 1.63-1.67 (m, 1H); 1.85-1.90 (m, 2H); 1.95-2.00 (m, 1H); 2.05-2.15 (m, 3H); 2.20-2.24 (m, 1H); 2.30-2.36 (m, 1H); 2.85-2.93 (m, 1H); 3.25-3.33 (m, 1H); 3.36-3.46 (m, 2H); 3.81-3.87 (m, 1H); 4.08 (t, J=8.3 Hz, 1H); 4.28 (d, J=5.0 Hz, 1H); 4.33-4.56 (m, 4H); 4.70 (t, J=8.3 Hz, 1H); 4.83-4.91 (m, 1H); 6.17 (dd, J=9.1 Hz, J=15.9 Hz, 1H); 6.67 (d, J=15.9 Hz, 1H); 7.25-7.44 (m, 10H); 8.22 (brs, 1H).

Example 34A. 2(S)-(2-(4-Cyclohexylpiperazinylcarbonyl)ethyl)-2-[3(S)-(4(S)-phenyloxazolidin-2-on-3-yl)-4(R)-(2-styryl)azetidin-2-on-1-yl]acetic acid Example 25A (0.787 g, 1.28 mmol) was hydrolyzed to give 0.665 g (92%) of Example 34A as an off-white solid; $^1$H NMR (CDCl$_3$) δ 1.05-1.13 (m, 1H); 1.20-1.40 (m, 5H); 1.60-1.64 (m, 1H); 1.79-1.83 (m, 2H); 2.00-2.05 (m, 2H); 2.22-2.44 (m, 3H); 2.67-2.71 (m, 1H); 2.93-3.01 (m, 4H); 3.14-3.18 (m, 1H); 3.38-3.42 (m, 1H); 3.48-3.52 (m, 1H); 3.64-3.69 (m, 1H); 4.06-4.14 (m, 2H); 4.34-4.43 (m, 2H); 4.56 (t, J=8.8 Hz, 1H); 4.73 (t, J=8.4 Hz, 1H); 6.15 (dd, J=9.1 Hz, J=16.0 Hz, 1H); 6.65 (d, J=16.0 Hz, 1H); 7.25-7.42 (m, 10H).

Example 34B. 2(R)-(Carboxymethyl)-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)carboxamide Example 25B (0.26 g, 0.38 mmol) was hydrolyzed to give 0.238 g (quantitative yield) of Example 34B as an off-white solid; ¹H NMR (CDCl₃) δ 3.27 (d, J=7.2 Hz, 1H); 4.06 (t, J=7.2 Hz, 1H); 4.15 (t, J=8.1 Hz, 1H); 4.27 (d, J=4.8 Hz, 1H); 4.56-4.76 (m, 5H); 6.34 (dd, J=9.5 Hz, J=15.7 Hz, 1H); 6.80 (d, J=15.7 Hz, 1H); 7.06 (t, J=7.7 Hz, 1H); 7.31-7.54 (m, 12H); 8.58 (t, J=5.9 Hz, 1H).

Example 34C. 2(R)-(Carboxymethyl)-2-[3(S)-(4(S)-phenyloxazolidin-2-on-3-yl)-4(R)-(2-styryl)azetidin-2-on-1-yl]acetic acid N—[(S)-α-methylbenzyl]amide Example 25C (0.215 g, 0.35 mmol) was hydrolyzed to give 0.195 g (quantitative yield) of Example 34C as an off-white solid; ¹H NMR (CDCl₃) δ 1.56 (d, J=7.0 Hz, 1H); 3.10 (dd, J=4.5 Hz, J=17.9 Hz, 1H); 3.18 (dd, J=9.8 Hz, J=17.9 Hz, 1H); 4.00 (dd, J=4.5 Hz, J=9.7 Hz, 1H); 4.14 (t, J=8.2 Hz, 1H); 4.26 (d, J=4.7 Hz, 1H); 5.02-5.09 (m, 1H); 6.41 (dd, J=9.4 Hz, J=15.8 Hz, 1H); 6.78 (d, J=15.8 Hz, 1H); 7.18 (t, J=7.3 Hz, 1H); 7.26-7.43 (m, 12H); 8.29 (d, J=8.2 Hz, 1H).

Example 34D. 2(R)-(Carboxymethyl)-2-[3(S)-(4(S)-phenyloxazolidin-2-on-3-yl)-4(R)-(2-styryl)azetidin-2-on-1-yl]acetic acid N—[(R)-α-methylbenzyl]amide Example 25D (0.22 g, 0.35 mmol) was hydrolyzed to give 0.20 g (quantitative yield) of Example 34D as an off-white solid; ¹H NMR (CDCl₃) δ 1.59 (d, J=7.0 Hz, 1H); 3.25 (d, J=7.0 Hz, 2H); 3.92 (t, J=7.3 Hz, 1H); 4.15 (t, J=8.3 Hz, 1H); 4.26 (d, J=5.0 Hz, 1H); 4.52 (dd, J=4.8 Hz, J=9.3 Hz, 1H); 4.65 (t, J=8.8 Hz, 1H); 4.72 (t, J=8.3 Hz, 1H); 5.07-5.28 (m, 1H); 6.29 (dd, J=9.5 Hz, J=15.6 Hz, 1H); 6.71 (d, J=16.0 Hz, 1H); 7.20-7.43 (m, 13H); 8.31 (d, J=8.0 Hz, 1H).

Example 34E. 2(R)-(Carboxymethyl)-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide Example 25E (0.253 g, 0.37 mmol) was hydrolyzed to give 0.232 g (quantitative yield) of Example 34E as an off-white solid; ¹H NMR (CDCl₃) δ 3.07-3.15 (m, 4H); 4.13 (t, J=8.2 Hz, 1H); 4.30 (d, J=4.9 Hz, 1H); 4.46-4.78 (m, 5H); 5.23 (dd, J=4.6 Hz, J=9.7 Hz, 1H); 6.20 (dd, J=9.4 Hz, J=15.9 Hz, 1H); 6.73 (d, J=15.9 Hz, 1H); 7.25-7.43 (m, 15H).

Example 34F. 2(S)-(Carboxyethyl)-2-[3(S)-(4(S)-phenyloxazolidin-2-on-3-yl)-4(R)-(2-chlorostyr-2-yl)azetidin-2-on-1-yl]acetic acid N-(3-trifluoromethylbenzyl)amide Example 25F (0.707 g, 0.99 mmol) was hydrolyzed to give 0.648 g (99%) of Example 34F as an off-white solid; ¹H NMR (CDCl₃) δ 2.22-2.28 (m, 2H); 2.49-2.64 (m, 2H); 4.09 (t, J=8.0 Hz, 1H); 4.25-4.62 (m, 6H); 4.87 (t, J=8.0 Hz, 1H); 6.88 (s, 1H); 7.25-7.66 (m, 15H).

Example 34G. 2(R)-(Carboxymethyl)-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide Example 25G (0.268 g, 0.39 mmol) was hydrolyzed to give 0.242 g (98%) of Example 34G as an off-white solid; ¹H NMR (CDCl₃) δ 3.26 (d, J=7.1 Hz, 1H); 3.79 (s, 3H); 4.14 (t, J=8.2 Hz, 1H); 4.25 (d, J=4.5 Hz, 1H); 4.51 (dd, J=5.9 Hz, J=15.5 Hz, 1H); 4.53-4.66 (m, 4H); 6.36 (dd, J=9.4 Hz, J=15.8 Hz, 1H); 8.88 (t, J=8.2 Hz, 1H); 6.70 (d, J=15.8 Hz, 1H); 7.18 (d, J=6.5 Hz, 1H); 7.25-7.48 (m, 10H); 7.48 (s, 1H); 8.66-8.69 (m, 1H).

Example 34H. (2R)-(Benzyloxymethyl)-2-[3(S)-(4(S)-phenyloxazolidin-2-on-3-yl)-4(R)-(2-styryl)azetidin-2-on-1-yl]acetic acid Example 25H (0.16 g, 0.28 mmol) was hydrolyzed to give 0.144 g (quantitative yield) of Example 34H as an off-white solid; ¹H NMR (CDCl₃) δ 3.65 (dd, J=4.0 Hz, J=9.5 Hz, 1H); 3.82 (dd, J=5.5 Hz, J=9.5 Hz, 1H); 4.11 (dd, J=7.8 Hz, J=8.8 Hz, 1H); 4.33 (s, 2H); 4.50 (d, J=5.0 Hz, 1H); 4.57 (t, J=9.0 Hz, 1H); 4.67 (dd, J=4.0 Hz, J=5.0 Hz, 1H); 4.69 (dd, J=5.0 Hz, J=9.5 Hz, 1H); 4.75 (t, J=8.0 Hz, 1H); 6.17 (dd, J=9.3 Hz, J=15.8 Hz, 1H); 6.55 (d, J=16.0 Hz, 1H); 7.09-7.12 (m, 2H); 7.19-7.42 (m, 13H).

Example 34I. 2(S)-(2-(4-Cyclohexylpiperazinylcarbonyl)methyl)-2-[3(S)-(4(S)-phenyloxazolidin-2-on-3-yl)-4(R)-(2-styryl)azetidin-2-on-1-yl]acetic acid Example 25I (737 mg, 1.12 mmol) was hydrolyzed to give 640 mg (95%) of Example 34I as an off-white solid. Example 34I exhibited an ¹H NMR spectrum consistent with the assigned structure.

Example 34J. 3(R)-[3(S)-(4(S)-Phenyloxazolidin-2-on-3-yl)-3-methyl-4(R)-(styr-2-yl)azetidin-2-on-1-yl]-3-[(3-trifluoromethyl)phenylmethylaminocarbonyl]propanoic acid Using the general method of Example 26, 120 mg (0.18 mmol) of Example 25J was hydrolyzed to give 108 mg (98%) of Example 34J as an off-white solid; ¹H NMR (CDCl₃) δ 1.22 (s, 3H); 3.25 (dd, J=3.5 Hz, J=18.0 Hz, 1H); 3.36 (dd, J=10.8 Hz, J=18.2 Hz, 1H); 4.01 (dd, J=4.0 Hz, J=10.5 Hz, 1H); 4.05 (dd, J=3.8 Hz, J=8.8 Hz, 1H); 4.33 (d, J=9.0 Hz, 1H); 4.44-4.51 (m, 3H); 4.61-4.66 (m, 1H); 4.73 (dd, J=3.8 Hz, J=8.8 Hz, 1H); 6.19 (dd, J=9.0 Hz, J=16.0 Hz, 1H); 6.74 (d, J=16.0 Hz, 1H); 7.22-7.54 (m, 13H); 7.65 (s, 1H).

Example 34K. 2(R)-(Carboxymethyl)-2-[3(S)-(4(S)-phenyloxazolidin-2-on-3-yl)-4(R)-(propen-1-yl)azetidin-2-on-1-yl]acetic acid N-(3-trifluoromethylbenzyl)amide Using the general method of Example 26, 160 mg (0.27 mmol) of Example 25K was hydrolyzed to give 131 mg (90%) of Example 34K as an off-white solid. ¹H NMR (CDCl₃) δ 1.69 (dd, J=1 Hz, J=6.5 Hz, 3H); 3.23 (d, J=7 Hz, 1H); 3.93 (t, J=7.3 Hz, 1H); 4.14-4.20 (m, 3H); 4.29 (dd, J=5 Hz, J=9.5 Hz, 1H); 4.43 (dd, J=6 Hz, J=15 Hz, 1H); 4.61 (dd, J=6.5 Hz, J=15 Hz, 1H); 4.66-4.74 (m, 2H); 5.50-5.55 (m, 1H); 5.90-5.98 (m, 1H); 7.32-7.60 (m, 9H); 8.60-8.64 (m, 1H).

Example 34L. 2(R)-(Carboxylmethyl)-2-[3(S)-(4(S)-phenyloxazolidin-2-on-3-yl)-4(R)-(2-styryl)azetidin-2-on-1-yl]acetic acid N—[(R)-1-(3-trifluoromethylpheny)ethyl]amide Example 25L (166 mg, 0.24 mmol) was hydrolyzed to give 152 mg (quantitative yield) of Example 34L as an off-white solid; and exhibited an ¹H NMR spectrum consistent with the assigned structure.

Example 34M. 2(S)-(Methoxycarbonylethyl)-2-[3 (S)-(4(S)-phenyloxazolidin-2-on-3-yl)-4(R)-(2-styryl)azetidin-2-on-1-yl]acetic acid Example 25M (875 mg, 1.64 mmol) was hydrolyzed to give 757 mg (97%) of Example 34M as an off-white solid, and exhibited an ¹H NMR spectrum consistent with the assigned structure.

Example 34N. 2(R)-(Carboxylmethyl)-2-[3(S)-(4 (S)-phenyloxazolidin-2-on-3-yl)-4(R)-(2-styryl)azetidin-2-on-1-yl]acetic acid N—[(S)-1-(3-trifluoromethylpheny)ethyl]amide Example 25N (38.5 mg, 0.057 mmol) was hydrolyzed to give 35 mg (quantitative yield) of Example 34N as an off-white solid, and exhibited an ¹H NMR spectrum consistent with the assigned structure.

Example 34O. 2(S)-(tert-Butoxycarbonylethyl)-2-[3 (S)-(4(S)-phenyloxazolidin-2-on-3-yl)-4(R)-(2-styryl)azetidin-2-on-1-yl]acetic acid Example 25O (97 mg, 0.18 mmol) was dissolved in methanol/tetrahydrofuran (2.5 mL/2 mL) and reacted with lithium hydroxide (0.85 mL of a 0.85M solution in water; 0.72 mmol) for 6 hours at room temperature. The reaction was diluted with 15 mL dichloromethane and aqueous hydrochloric acid (1M) was added until the pH of the aqueous layer reached 5 (as measured by standard pH paper). The organic layer was then separated and evaporated to dryness to give 84 mg (89%) of Example 34O as an off-white solid, and exhibited an ¹H NMR spectrum consistent with the assigned structure.

Example 34P. 2(S)-(tert-Butoxycarbonylethyl)-2-[3 (S)-(4(S)-phenyloxazolidin-2-on-3-yl)-4(R)-(2-styryl)azetidin-2-on-1-yl]acetic acid Example 25P (200 mg, 0.39 mmol) was hydrolyzed according to the method used for Example 34O to give 155 mg (88%) of Example 34P as an off-white solid; and exhibited an ¹H NMR spectrum consistent with the assigned structure.

Example 34Q. 2(R)-(2-(3-trifluoromethylbenzyl) amino-1-ylcarbonyl)ethyl)-2-[3(S)-(4(S)-phenyloxazolidin-2-on-3-yl)-4(R)-(2-styryl)azetidin-2-on-1-yl]acetic acid Example 25Q (150 mg, 0.24 mmol) was hydrolyzed according to the method used for Example 34O to give 143 mg (97%) of Example 34Q as an off-white solid, and exhibited an ¹H NMR spectrum consistent with the assigned structure.

Example 34R. 2(R)-(tert-Butoxycarbonylmethyl)-2-[3(RS)-2-thienylmethyl)-4(R)-(2-styryl)azetidin-2-on-1-yl]acetic acid N-(3-trifluoromethylbenzyl) amide The imine prepared from 290 mg (0.84 mmol) of D-aspartic acid β-t-butyl ester α-(3-trifluoromethyl)benzylamide and cinnamaldehyde was combined with 2-thiophene-acetyl chloride to give 42 mg (8%) of Example 34R after flash column chromatography purification (70:30 hexanes/ethyl acetate), and exhibited an ¹H NMR spectrum consistent with the assigned structure.

The following compounds were prepared according to the processes described herein:

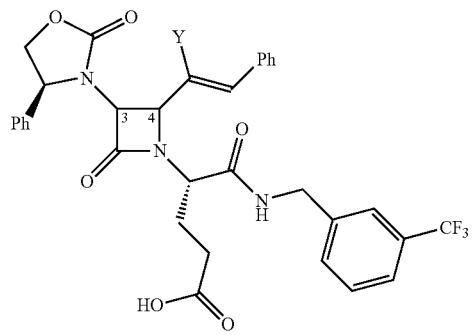

| Example | Y | C(3)-C(4) Stereochemistry |
|---------|---|---------------------------|
| 34S | F | (3S,4R) |
| 34T | F | not determined |
| 34U | Br | not determined |

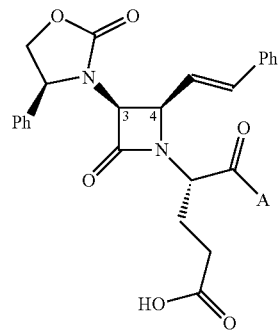

| Example | A |
|---------|---|
| 34V | (R)-1,2,3,4-tetrahydro-1-naphtylamide |
| 34W | 1-phenyl-cyclopentylamide |

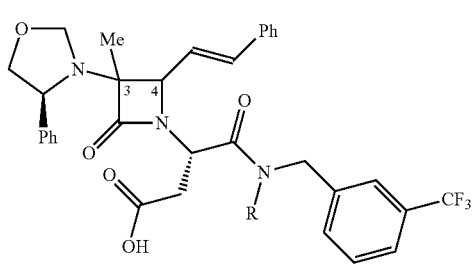

| Example | C(3)-C(4) Stereochemistry | R |
|---|---|---|
| 34X | (3S,4R) | Me |
| 34Y | not determined | H |

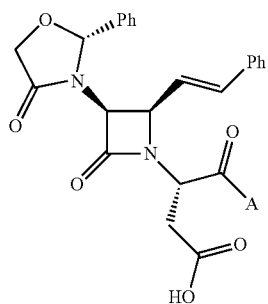

| Example | A |
|---|---|
| 34Z | 1-phenyl-cyclopent-1-ylamino |
| 34AA | (R)-1-phenylethy-1-amino |

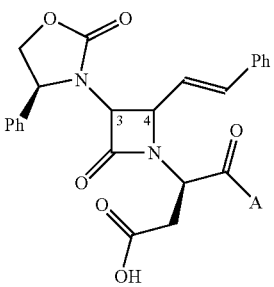

| Example | C(3)-C(4) Stereochemistry | A |
|---|---|---|
| 34AB | (3S,4R) | α,α-dimethylbenzylamino |
| 34AC | not determined | N-methyl-3-CF3-benzylamino |
| 34AD | not determined | (R)-α-methylbenzylamino |
| 34AE | (3S,4R) | (R)-α,N-dimethylbenzylamino |

Examples 36-42A, shown in the following table, were prepared using the procedure of Example 6, except that N-benzyloxycarbonyl-D-aspartic acid β-t-butyl ester monohydrate was replaced with Example 27, and 3-(trifluoromethyl)benzyl amine was replaced with the appropriate amine; all listed Examples exhibited an $^1$H NMR spectrum consistent with the assigned structure.

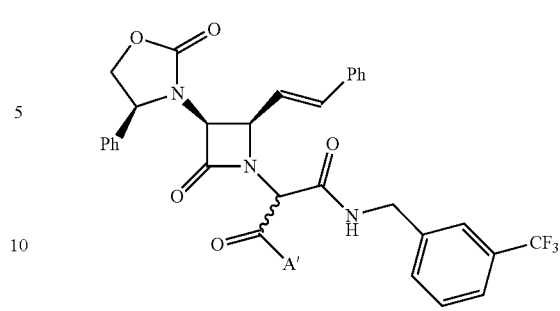

| Example | A' |
|---|---|
| 36 | 2-(piperidinyl)ethylamino |
| 37 | 4-(piperidinyl)piperidinyl |
| 38 | 4-(2-phenylethyl)piperazinyl |
| 39 | 1-benzylpiperidin-4-ylamino |
| 40 | 4-butylpiperazinyl |
| 41 | 4-isopropylpiperazinyl |
| 42 | 4-cyclohexylpiperazinyl |
| 42A | 4-[2-(piperidinyl)ethyl]piperidinyl |

Examples 43-86A, shown in the following table, were prepared using the procedure of Example 6, except that N-benzyloxycarbonyl-D-aspartic acid β-t-butyl ester monohydrate was replaced with Example 28, and 3-(trifluoromethyl)benzyl amine was replaced with the appropriate amine; all listed Examples exhibited an $^1$H NMR spectrum consistent with the assigned structure.

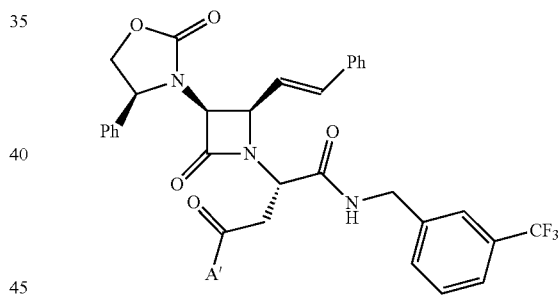

| Example | A' |
|---|---|
| 43 | 2-(piperidinyl)ethylamino |
| 44 | 4-(piperidinyl)piperidinyl |
| 45 | 4-(phenylethyl)piperazinyl |
| 46 | fur-2-ylmethylamino |
| 47 | 4-(pyrrolidinyl)piperazinyl |
| 48 | 4-(3-trifluoromethylphenyl)piperazinyl |
| 49 | 4-(benzyloxycarbonyl)piperazinyl |
| 50 | 4-[2-(2-hydroxyethoxy)ethyl]piperazinyl |
| 51 | 4-benzylpiperazinyl |
| 52 | 4-(3,4-methylenedioxybenzyl)piperazinyl |
| 53 | 4-phenylpiperazinyl |
| 54 | 4-(3-phenylprop-2-enyl)piperazinyl |
| 55 | 4-ethylpiperazinyl |
| 56 | 2-(dimethylamino)ethylamino |
| 57 | 4-(pyrrolidinylcarbonylmethyl)piperazinyl |
| 58 | 4-(1-methylpiperidin-4-yl)piperazinyl |
| 59 | 4-butylpiperazinyl |
| 60 | 4-isopropylpiperazinyl |
| 61 | 4-pyridylmethylamino |
| 62 | 3-(dimethylamino)propylamino |

-continued

| Example | A' |
|---|---|
| 63 | 1-benzylpiperidin-4-ylamino |
| 64 | N-benzyl-2-(dimethylamino)ethylamino |
| 65 | 3-pyridylmethylamino |
| 66 | 4-(cyclohexyl)piperazinyl |
| 67 | 4-(2-cyclohexylethyl)piperazinyl |
| 68 | 4-[2-(morpholin-4-yl)ethyl]piperazinyl |
| 69 | 4-(4-tert-butylbenzyl)piperazinyl |
| 70 | 4-[2-(piperidinyl)ethyl]piperazinyl |
| 71 | 4-[3-(piperidinyl)propyl]piperazinyl |
| 72 | 4-[2-(N,N-dipropylamino)ethyl]piperazinyl |
| 73 | 4-[3-(N,N-diethylamino)propyl]piperazinyl |
| 74 | 4-[2-(dimethylamino)ethyl]piperazinyl |
| 75 | 4-[3-(pyrrolidinyl)propyl]piperazinyl |
| 76 | 4-(cyclohexylmethyl)piperazinyl |
| 77 | 4-cyclopentylpiperazinyl |
| 78 | 4-[2-(pyrrolidinyl)ethyl]piperazinyl |
| 79 | 4-[2-(thien-2-yl)ethyl]piperazinyl |
| 80 | 4-(3-phenylpropyl)piperazinyl |
| 81 | 4-[2-(N,N-diethylamino)ethyl]piperazinyl |
| 82 | 4-benzylhomopiperazinyl |
| 83 | 4-(bisphenylmethyl)piperazinyl |
| 84 | 3-(4-methylpiperazinyl)propylamino |
| 85 | (+)-3(S)-1-benzylpyrrolidin-3-ylamino |
| 86 | 2-pyridylmethylamino |
| 86A | 4-[2-(piperidinyl)ethyl]piperidinyl |
| 86B | 1-benzylpiperidin-4-ylamino N-oxide |

Example 86B

Example 63 (44 mg, 0.06 mmol) was dissolved in 4 mL dichloromethane and reacted with 3-chloroperoxybenzoic acid (12 mg, 0.07 mmol) until the reaction was complete as assessed by TLC (dichloromethane 94%/methanol 6%, UV detection). The reaction was quenched with aqueous sodium sulfite, the dichloromethane layer was washed with 5% aqueous sodium bicarbonate and distilled water. Evaporation of the dichloromethane layer afforded Example 86B as an off-white solid (35 mg, 78%), and exhibited an $^1$H NMR spectrum consistent with the assigned structure.

Examples 121-132, shown in the following table, were prepared using the procedure of Example 6, except that N-benzyloxycarbonyl-D-aspartic acid β-t-butyl ester monohydrate was replaced with Example 30, and 3-(trifluoromethyl)benzyl amine was replaced with the appropriate amine; all listed Examples exhibited an $^1$H NMR spectrum consistent with the assigned structure.

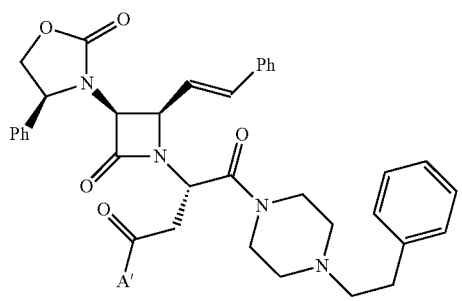

| Example | A' |
|---|---|
| 121 | 3-trifluoromethylbenzylamino |
| 122 | morpholin-4-ylamino |
| 123 | 2-(dimethylamino)ethylamino |
| 124 | 3-(dimethylamino)propylamino |
| 125 | cyclohexylamino |
| 126 | piperidinyl |
| 127 | 2-methoxyethylamino |
| 128 | isopropylamino |
| 129 | isobutylamino |
| 130 | ethylamino |
| 131 | dimethylamino |
| 132 | methylamino |

Examples 132A-132B, shown in the following table, were prepared using the procedure of Example 6, except that N-benzyloxycarbonyl-D-aspartic acid β-t-butyl ester monohydrate was replaced with Example 34I, and 3-(trifluoromethyl)benzyl amine was replaced with the appropriate amine; all listed Examples exhibited an $^1$H NMR spectrum consistent with the assigned structure.

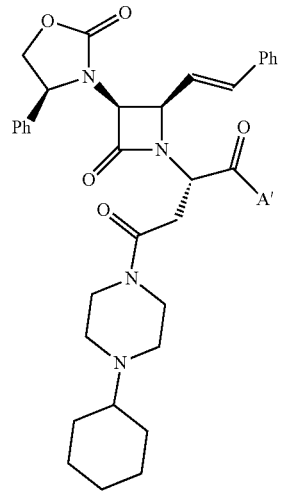

| Example | A' |
|---|---|
| 132A | (2,3-dichlorobenzyl)amino |
| 132B | 1-phenylcyclohexylamino |

Example 132C. 2(S)-(tert-Butoxycarbonylmethyl)-2-[3(S)-(4(S)-phenyloxazolidin-2-on-3-yl)-4(R)-(2-styryl)azetidin-2-on-1-yl] acetic acid N-(4-cyclohexyl)piperazinamide Example 132C was prepared using the procedure of Example 6, except that N-benzyloxycarbonyl-D-aspartic acid β-t-butyl ester monohydrate was replaced with Example 34P, and 3-(trifluoromethyl)benzyl amine was replaced with 1-cyclohexyl-piperazine. Example 132C exhibited an $^1$H NMR spectrum consistent with the assigned structure.

The compounds shown in the following table were prepared according to the processes described herein.

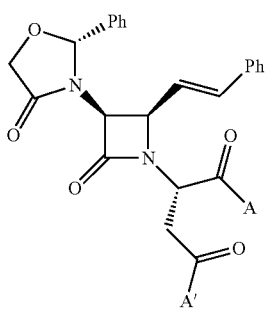

| Example | A | A' |
|---|---|---|
| 132D | 1-phenyl-cyclopent-1-ylamino | 4-(piperidinyl)piperidinyl |
| 132E | 1-phenyl-cyclopent-1-ylamino | 1-benzylpiperidin-4-ylamino |
| 132F | (R)-1-phenylethy-1-amino | 4-(piperidinyl)piperidinyl |

Examples 133-134G, shown in the following table, were prepared using the procedure of Example 6, except that N-benzyloxycarbonyl-D-aspartic acid β-t-butyl ester monohydrate was replaced with Example 32, and 3-(trifluoromethyl)benzyl amine was replaced with the appropriate amine; all listed Examples exhibited an ¹H NMR spectrum consistent with the assigned structure.

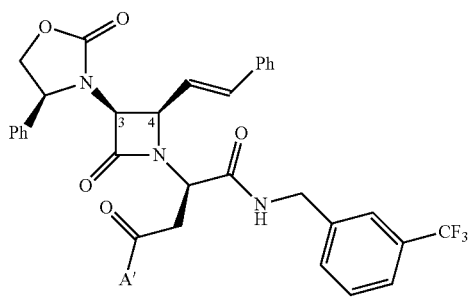

| Example | A' |
|---|---|
| 133 | 4-(piperidinyl)piperidinyl |
| 134 | 4-(2-phenylethyl)piperazinyl |
| 134A | 4-[2-(piperidinyl)ethyl]piperidinyl |
| 134B | 4-(pyrrolidinyl)piperazinyl |
| 134C | 1-benzylpiperidin-4-ylamino |
| 134D | (pyridin-3-ylmethyl)amino |

| Example | A' |
|---|---|
| 134E | 3-(dimethylamino)propylamino |
| 134F | 3-(S)-(1-benzylpyrrolidin-3-yl)amino |
| 134G | 4-[(piperidinyl)methyl]piperidinyl |
| 134H | 4-(piperidinyl)piperidinyl N-oxide |

Example 134H

Example 134H was prepared using the procedure of Example 86B, except that Example 133 was replaced with Example 110. Example 134H was obtained as an off-white solid (48 mg, 94%), and exhibited an ¹H NMR spectrum consistent with the assigned structure.

Example 134I. 2(R)-[[4-(Piperidinyl)piperidinyl]carboxymethyl]-2-[3(S)-(4(R)-phenyloxazolidin-2-on-3-yl)-4(R)-(2-styryl)azetidin-2-on-1-yl]acetic acid N-(3-trifluoromethylbenzyl)amide Example 134I was prepared using the procedure of Example 6, except that N-benzyloxycarbonyl-D-aspartic acid β-t-butyl ester monohydrate was replaced with Example 32A, and 3-(trifluoromethyl)benzyl amine was replaced with 4-(piperidinyl)piperidine, and exhibited an ¹H NMR spectrum consistent with the assigned structure.

The compounds shown in the following table were prepared according to the processes described herein.

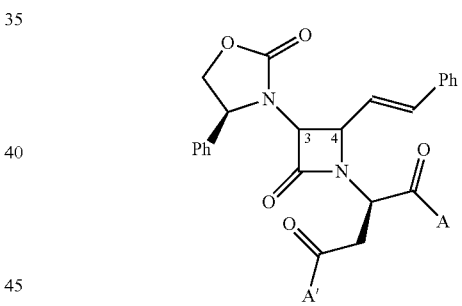

| Example | C(3)-C(4) Stereochemistry | A | A' |
|---|---|---|---|
| 134J | (3S,4R) | α,α-dimethylbenzylamino | 4-(piperidinyl)piperidinyl |
| 134K | (3S,4R) | α,α-dimethylbenzylamino | 1-benzylpiperidin-4-ylamino |
| 134L | not determined | N-methyl-3-CF3-benzylamino | 4-(piperidinyl)piperidinyl |
| 134M | (3S,4R) | N-methyl-3-CF3-benzylamino | 3-(pyrrolidinyl)piperidinyl |
| 134N | not determined | (R)-α-methylbenzylamino | 4-(piperidinyl)piperidinyl |
| 134O | (3S,4R) | (R)-α,N-dimethylbenzylamino | 4-(piperidinyl)piperidinyl |

Example 222. 2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)carboxamide Example 222 was prepared using the procedure of Example 6, except that N-benzyloxycarbonyl-D-aspartic acid β-t-butyl ester monohydrate was replaced with Example 34B, and 3-(trifluoromethyl)benzyl amine was replaced with 4-(piperidinyl)piperidine; Example 222 exhibited an $^1$H NMR spectrum consistent with the assigned structure.

Example 223. 2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(S)-α-methylbenzyl]amide Example 223 was prepared using the procedure of Example 6, except that N-benzyloxycarbonyl-D-aspartic acid β-t-butyl ester monohydrate was replaced with Example 34C, and 3-(trifluoromethyl)benzyl amine was replaced with 4-(piperidinyl)piperidine; Example 223 exhibited an $^1$H NMR spectrum consistent with the assigned structure.

Example 224. 2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(R)-α-methylbenzyl]amide Example 224 was prepared using the procedure of Example 6, except that N-benzyloxycarbonyl-D-aspartic acid β-t-butyl ester monohydrate was replaced with Example 34D, and 3-(trifluoromethyl)benzyl amine was replaced with 4-(piperidinyl)piperidine; Example 223 exhibited an $^1$H NMR spectrum consistent with the assigned structure.

Example 225. 2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide Example 225 was prepared using the procedure of Example 6, except that N-benzyloxycarbonyl-D-aspartic acid β-t-butyl ester monohydrate was replaced with Example 34E, and 3-(trifluoromethyl)benzyl amine was replaced with 4-(piperidinyl)piperidine; Example 223 exhibited an $^1$H NMR spectrum consistent with the assigned structure; Calc'd for $C_{43}H_{48}F_3N_5O_5$: C, 66.91; H, 6.27; N, 9.07; found. C, 66.68; H, 6.25; N, 9.01.

Example 225. Hydrochloride Salt

Example 225 (212.5 mg) was dissolved in 30 mL dry $Et_2O$. Dry HCl gas was bubbled through this solution resulting in the rapid formation of an off-white precipitate. HCl addition was discontinued when no more precipitate was observed forming (ca. 5 minutes). The solid was isolated by suction filtration, washed twice with 15 mL of dry $Et_2O$ and dried to 213.5 mg (96% yield) of an off-white solid; Calc'd for $C_{43}H_{49}ClF_3N_5O_5$: C, 63.89; H, 6.11; N, 8.66; Cl, 4.39; found. C, 63.41; H, 5.85; N, 8.60; Cl, 4.86.

Example 225A. 2(R)-[[4-[2-(piperidinyl)ethyl]piperidinyl]carbonylmethyl]-2-[3(S)-(4(S)-phenyloxazolidin-2-on-3-yl)-4(R)-(2-styryl)azetidin-2-on-1-yl] acetic acid N—[(S)-α-methylbenzyl]amide Example 225A was prepared using the procedure of Example 6, except that N-benzyloxycarbonyl-D-aspartic acid β-butyl ester monohydrate was replaced with Example 34C, and 3-(trifluoromethyl)benzyl amine was replaced with 4-[2-(piperidinyl)ethyl]piperidine. Example 225A exhibited an $^1$H NMR spectrum consistent with the assigned structure.

Example 225B. 2(R)-[[4-[2-(piperidinyl)ethyl]piperidinyl]carbonylmethyl]-2-[3(S)-(4(S)-phenyloxazolidin-2-on-3-yl)-4(R)-(2-styryl)azetidin-2-on-1-yl] acetic acid N—[(R)-α-methylbenzyl]amide Example 225B was prepared using the procedure of Example 6, except that N-benzyloxycarbonyl-D-aspartic acid β-t-butyl ester monohydrate was replaced with Example 34D, and 3-(trifluoromethyl)benzyl amine was replaced with 4-[2-(piperidinyl)ethyl]piperidine. Example 225B exhibited an $^1$H NMR spectrum consistent with the assigned structure.

Example 225C. 2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(R)-1-(3-trifluoromethylpheny)ethyl]amide Example 225C was prepared using the procedure of Example 6, except that N-benzyloxycarbonyl-D-aspartic acid β-t-butyl ester monohydrate was replaced with Example 34L, and 3-(trifluoromethyl)benzyl amine was replaced with 4-(piperidinyl)piperidine. Example 225C exhibited an $^1$H NMR spectrum consistent with the assigned structure.

Example 225D. 2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(S)-1-(3-trifluoromethylpheny)ethyl]amide Example 225D was prepared using the procedure of Example 6, except that N-benzyloxycarbonyl-D-aspartic acid β-t-butyl ester monohydrate was replaced with Example 34N, and 3-(trifluoromethyl)benzyl amine was replaced with 4-(piperidinyl)piperidine. Example 225D exhibited an $^1$H NMR spectrum consistent with the assigned structure.

Examples 87-120E, shown in the following table, were prepared using the procedure of Example 6, except that N-benzyloxycarbonyl-D-aspartic acid β-t-butyl ester monohydrate was replaced with Example 29, and 3-(trifluoromethyl)benzyl amine was replaced with the appropriate amine; all listed Examples exhibited an $^1$H NMR spectrum consistent with the assigned structure.

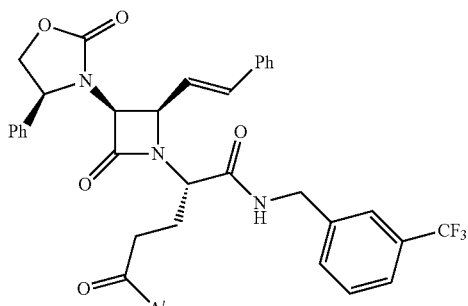

| Example | A' |
|---|---|
| 87 | 2-(piperidinyl)ethylamino |
| 88 | 4-(piperidinyl)piperidinyl |
| 89 | 2-(pyrid-2-yl)ethylamino |
| 90 | morpholin-4-ylamino |
| 91 | 4-(pyrrolidinyl)piperazinyl |
| 92 | 4-(3-trifluorophenyl)piperazinyl |
| 93 | 4-(benzyloxycarbonyl)piperazinyl |
| 94 | 4-[2-(2-hydroxylethoxy)ethyl]piperazinyl |
| 95 | 4-benzylpiperazinyl |
| 96 | 4-(3,4-methylenedioxybenzyl)piperazinyl |
| 97 | 4-phenylpiperazinyl |
| 98 | 4-(3-phenylprop-2-enyl)piperazinyl |
| 99 | 4-ethylpiperazinyl |
| 100 | 2-(dimethylamino)ethylamino |
| 101 | 4-(pyrrolidinylcarbonylmethyl)piperazinyl |
| 102 | 4-(1-methylpiperidin-4-yl)piperazinyl |
| 103 | 4-butylpiperazinyl |
| 104 | 4-isopropylpiperazinyl |
| 105 | 4-pyridylmethylamino |
| 106 | 3-(dimethylamino)propylamino |
| 107 | 1-benzylpiperidin-4-ylamino |
| 108 | N-benzyl-2-(dimethylamino)ethylamino |
| 109 | 3-pyridylmethylamino |
| 110 | 4-cyclohexylpiperazinyl |
| 111 | 4-(2-cyclohexylethyl)piperazinyl |
| 112 | 4-[2-(morpholin-4-yl)ethyl]piperazinyl |
| 113 | 4-(4-tert-butylbenzyl)piperazinyl |
| 114 | 4-[2-(piperidinyl)ethyl]piperazinyl |
| 115 | 4-[3-(piperidinyl)propyl]piperazinyl |
| 116 | 4-[2-(diisopropylamino)ethyl]piperazinyl |
| 117 | 4-[3-(diethylamino)propyl]piperazinyl |
| 118 | 4-(2-dimethylaminoethyl)piperazinyl |
| 119 | 4-[3-(pyrrolidinyl)propyl]piperazinyl |
| 120 | 4-(cyclohexylmethyl)piperazinyl |
| 120A | 4-[2-(piperidinyl)ethyl]piperidinyl |
| 120B | 4-propyl-piperazinyl |
| 120C | 4-[N-(isopropyl)acetamid-2-yl]piperazinyl |
| 120D | 3-benzyl-hexahydro-(1H)-1,3-diazepinyl |
| 120E | 4-(piperidinylmethyl)piperidinyl |
| 120F | 4-cyclohexylpiperazinyl N-oxide |
| 120G | methoxy |
| 120H | 4-cyclohexylpiperazinyl |

Example 120F

Example 120F was prepared using the procedure of Example 86B, except that Example 63 was replaced with Example 110 to give an off-white solid (54.5 mg, 98%). Example 120F exhibited an $^1$H NMR spectrum consistent with the assigned structure.

Example 120G. 2(S)-(Methoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide Example 120G was prepared using the procedure of Example 6, except that N-benzyloxycarbonyl-D-aspartic acid β-t-butyl ester monohydrate was replaced with Example 34M, and exhibited an $^1$H NMR spectrum consistent with the assigned structure.

Example 35. 2(S)-[4-(2-phenylethyl)piperazinylcarbonylethyl]-2-[3(S)-(4(S)-phenyloxazolidin-2-on-3-yl)-4(R)-(2-styryl)azetidin-2-on-1-yl]acetic acid N-(3-trifluoromethylbenzyl)amide Using the procedure of Example 6, except that N-benzyloxycarbonyl-D-aspartic acid β-t-butyl ester monohydrate was replaced with the carboxylic acid of Example 29 and 3-(trifluoromethyl)benzyl amine was replaced with 4-(2-phenylethyl)piperazine, the title compound was prepared; $^1$H NMR (CDCl$_3$) δ 2.21-2.23 (m, 1H); 2.25-2.45 (m, 6H); 2.52-2.63 (m, 3H); 2.72-2.82 (m, 2H); 3.42-3.48 (m, 2H); 3.52-3.58 (m, 1H); 4.13-4.18 (m, 1H); 4.26 (dd, J=5.1 Hz, J=8.3 Hz, 1H); 4.29 (d, J=5.0 Hz, 1H); 4.44 (dd, J=6.0 Hz, J=15.0 Hz, 1H); 4.54 (dd, J=6.2 Hz, J=14.9 Hz, 1H); 4.61-4.68 (m, 2H); 4.70-4.75 (m, 1H); 6.27 (dd, J=9.6 Hz, J=15.8 Hz, 1H); 6.73 (d, J=15.8 Hz, 1H); 7.16-7.60 (m, 19H); 8.07-8.12 (m, 1H); FAB$^+$ (M+H)$^+$/z 794; Elemental Analysis calculated for $C_{45}H_{46}F_3N_5O_5$: C, 68.08; H, 5.84; N, 8.82; found: C, 67.94; H, 5.90; N, 8.64.

Examples 141-171, shown in the following table, were prepared using the procedure of Example 6, except that N-benzyloxycarbonyl-D-aspartic acid β-t-butyl ester monohydrate was replaced with Example 34, and 3-(trifluoromethyl)benzyl amine was replaced with the appropriate amine; all listed Examples exhibited an $^1$H NMR spectrum consistent with the assigned structure.

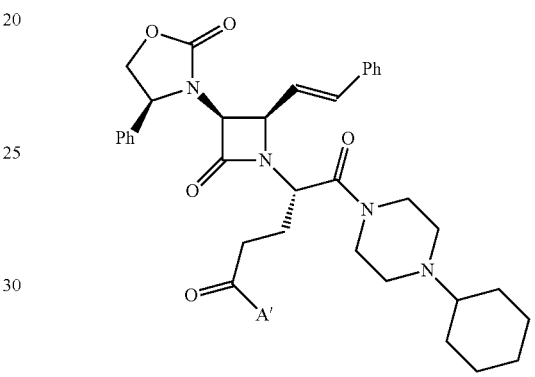

| Example | A' |
|---|---|
| 141 | benzylamino |
| 142 | (2-methylbenzyl)amino |
| 143 | (3-methylbenzyl)amino |
| 144 | (4-methylbenzyl)amino |
| 145 | (α-methylbenzyl)amino |
| 146 | N-benzyl-N-methylamino |
| 147 | N-benzyl-N-(t-butyl)amino |
| 148 | N-benzyl-N-butylamino |
| 149 | (3,5-dimethylbenzyl)amino |
| 150 | (2-phenylethyl)amino |
| 151 | dimethylamino |
| 152 | (3-trifluoromethoxybenzyl)amino |
| 153 | (3,4-dichlorobenzyl)amino |
| 154 | (3,5-dichlorobenzyl)amino |
| 155 | (2,5-dichlorobenzyl)amino |
| 156 | (2,3-dichlorobenzyl)amino |
| 157 | (2-fluoro-5-trifluoromethylbenzyl)amino |
| 158 | (4-fluoro-3-trifluoromethylbenzyl)amino |
| 159 | (3-fluoro-5-trifluoromethylbenzyl)amino |
| 160 | (2-fluoro-3-trifluoromethylbenzyl)amino |
| 161 | (4-chloro-3-trifluoromethylbenzyl)amino |
| 162 | indan-1-ylamino |
| 163 | 4-(2-hydroxybenzimidazol-1-yl)-piperidinyl |
| 164 | 3(S)-(tert-butylaminocarbonyl)-1,2,3,4-tetrahydroisoquinolin-2-yl |
| 165 | (3,3-dimethylbutyl)amino |
| 166 | 4-hydroxy-4-phenylpiperidinyl |
| 167 | (cyclohexylmethyl)amino |
| 168 | (2-phenoxyethyl)amino |
| 169 | 3,4-methylenedioxybenzylamino |
| 170 | 4-benzylpiperidinyl |
| 171 | (3-trifluoromethylphenyl)amino |

Examples 172-221R, shown in the following table, were prepared using the procedure of Example 6, except that N-benzyloxycarbonyl-D-aspartic acid β-t-butyl ester monohydrate was replaced with Example 34A, and 3-(trifluoromethyl)benzyl amine was replaced with the appropriate amine; all listed Examples exhibited an ¹H NMR spectrum consistent with the assigned structure.

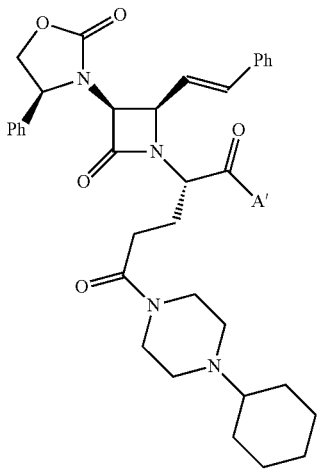

| Example | A' |
|---|---|
| 172 | (3-trifluoromethoxybenzyl)amino |
| 173 | (3,4-dichlorobenzyl)amino |
| 174 | (3,5-dichlorobenzyl)amino |
| 175 | (2,5-dichlorobenzyl)amino |
| 176 | (2,3-dichlorobenzyl)amino |
| 177 | (2-fluoro-5-trifluoromethylbenzyl)amino |
| 178 | (4-fluoro-3-trifluoromethylbenzyl)amino |
| 179 | (3-fluoro-5-trifluoromethylbenzyl)amino |
| 180 | (2-fluoro-3-trifluoromethylbenzyl)amino |
| 181 | (4-chloro-3-trifluoromethylbenzyl)amino |
| 182 | (2-trifluoromethylbenzyl)amino |
| 183 | (3-methoxybenzyl)amino |
| 184 | (3-fluorobenzyl)amino |
| 185 | (3,5-difluorobenzyl)amino |
| 186 | (3-chloro-4-fluorobenzyl)amino |
| 187 | (3-chlorobenzyl)amino |
| 188 | [3,5-bis(trifluoromethyl)benzyl]amino |
| 189 | (3-nitrobenzyl)amino |
| 190 | (3-bromobenzyl)amino |
| 191 | benzylamino |
| 192 | (2-methylbenzyl)amino |
| 193 | (3-methylbenzyl)amino |
| 194 | (4-methylbenzyl)amino |
| 195 | (α-methylbenzyl)amino |
| 196 | (N-methylbenzyl)amino |
| 197 | (N-tert-butylbenzyl)amino |
| 198 | (N-butylbenzyl)amino |
| 199 | (3,5-dimethylbenzyl)amino |
| 200 | (2-phenylethyl)amino |
| 201 | (3,5-dimethoxybenzyl)amino |
| 202 | (1R)-(3-methoxyphenyl)ethylamino |
| 203 | (1S)-(3-methoxyphenyl)ethylamino |
| 204 | (α,α-dimethylbenzyl)amino |
| 205 | N-methyl-N-(3-trifluoromethylbenzyl)amino |
| 206 | [(S)-α-methylbenzyl]amino |
| 207 | (1-phenylcycloprop-1yl)amino |
| 208 | (pyridin-2-ylmethyl)amino |
| 209 | (pyridin-3-ylmethyl)amino |
| 210 | (pyridin-4-ylmethyl)amino |
| 211 | (fur-2-ylmethyl)amino |
| 212 | [(5-methylfur-2-yl)methyl]amino |
| 213 | (thien-2-ylmethyl)amino |
| 214 | [(S)-1,2,3,4-tetrahydro-1-naphth-1-yl]amino |
| 215 | [(R)-1,2,3,4-tetrahydro-1-naphth-1-yl]amino |
| 216 | (indan-1-yl)amino |
| 217 | (1-phenylcyclopent-1-yl)amino |
| 218 | (α,α-dimethyl-3,5-dimethoxybenzyl)amino |
| 219 | (2,5-dimethoxybenzyl)amino |
| 220 | (2-methoxybenzyl)amino |
| 221 | (α,α,2-trimethylbenzyl)amino |
| 221A | N-methyl-3-Me-benzylamide |
| 221B | N-methyl-2,3-Cl-benzylamide |
| 221C | N-methyl-3-Cl-benzylamide |
| 221D | N-methyl-3-Br-benzylamide |
| 221E | N-methyl-3,5-Cl-benzylamide |
| 221F | (R)-1-(3-trifluorophenyl)ethylamide |
| 221G | 1-phenyl-cyclohexylamide |
| 221H | 1-(2-fluorophenyl)-cyclopentylamide |
| 221I | 1-(4-fluorophenyl)-cyclopentylamide |
| 221J | 4-CF3-benzylamide |
| 221K | α-phenyl-benzylamide |
| 221L | 3-phenyl-benzylamide |
| 221M | dibenzylamide |
| 221N | 1-naphthalene-methylamide |
| 221O | 1,2,3,4-tetrahydro-isoquinolinamide |
| 221P | indan-2-ylamino |
| 221Q | α-(2-OH-ethyl)benzylamide |
| 221R | (S)-indan-1-ylamino |

The compounds shown in the following table were prepared according to the processes described herein.

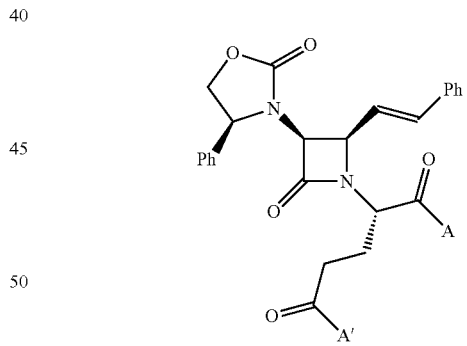

| Example | A | A' |
|---|---|---|
| 221S | (R)-1-indanylamino | 4-cyclohexylpiperazinyl |
| 221T | (αR)-α-(t-butoxycarbonylmethyl)benzylamino | 4-cyclohexylpiperazinyl |
| 221U | (R)-1,2,3,4-tetrahydro-1-naphtylamino | 4-(2-morpholinoethyl)-piperazinyl |
| 221V | (R)-1,2,3,4-tetrahydro-1-naphtylamino | 2-dimethylaminoethylamino |
| 221W | (R)-1,2,3,4-tetrahydro-1-naphtylamino | 4-(2-phenylethyl)-homopiperazinyl |
| 221X | (R)-1,2,3,4-tetrahydro-1-naphtylamino | 2-(1-piperidyl)ethylamino |
| 221Y | (R)-1,2,3,4-tetrahydro-1-naphtylamino | (S)-2-(1-pyrrolidinylmethyl)pyrrolidinyl |

| Example | A | A' |
|---|---|---|
| 221Z | (R)-1,2,3,4-tetrahydro-1-naphtylamino | 2-(1-pyrrolidinyl)ethylamino |
| 221AA | (R)-1,2,3,4-tetrahydro-1-naphtylamino | 4-(1-piperidyl)piperidinyl |
| 221AB | 3-CF3-benzylamino | 4-n-butylpiperazinyl |
| 221AC | 3-CF3-benzyiamino | 4-ethylpiperazinyl |
| 221AD | (R)-1,2,3,4-tetrahydro-1-naphtylamino | (R)-1-benzylpyrrolidin-3-ylamino |
| 221AE | (R)-1,2,3,4-tetrahydro-1-naphtylamino | quinuclidin-3-ylamino |
| 221AF | (R)-1,2,3,4-tetrahydro-1-naphtylamino | 4-methylhomopiperazinyl |
| 221AG | (R)-1,2,3,4-tetrahydro-1-naphtylamino | 2-pyrrolylphenylamino |
| 221AH | (R)-1,2,3,4-tetrahydro-1-naphlylamino | morpholin-4-ylethylamino |
| 221AI | (R)-1,2,3,4-tetrahydro-1-naphtylamino | (S)-1-ethylpyrrolidin-2-ylaminomethyl |
| 221AJ | (R)-1,2,3,4-tetrahydro-1-naphtylamino | (R)-1-ethylpyrrolidin-2-ylaminomethyl |
| 221AK | (R)-1,2,3,4-tetrahydro-1-naphtylamino | (S)-1-butoxycarbonylpyrrolidin-3-ylamino |
| 221AL | (R)-1,2,3,4-tetrahydro-1-naphtylamino | quinolin-3-ylamino |
| 221AM | 1-(3-fluorophenyl)-cyclopentylamino | 4-cyclohexylpiperazinyl |
| 221AN | 1-(4-chlorophenyl)-cyclopropylamino | 4-cyclohexylpiperazinyl |
| 221AO | 1-(4-methoxyphenyl)-cyclopropylamino | 4-cyclohexylpiperazinyl |
| 221AP | 1-(4-methylphenyl)-cyclopropylamino | 4-cyclohexylpiperazinyl |
| 221AQ | 1-(4-chlorophenyl)-cyclopentylamino | 4-cyclohexylpiperazinyl |
| 221AS | 1-(4-methylphenyl)-cyclopentylamino | 4-cyclohexylpiperazinyl |
| 221AT | (R)-1,2,3,4-tetrahydro-1-naphtylamino | 3-(4-chlorophenyl)isoxazolin-5-ylamino |
| 221AU | 1-phenylcyclopentylamino | 4-(1-pyrrolidyl)piperidinyl |
| 221AV | indolinyl | 4-cyclohexylpiperazinyl |
| 221AW | 5-indanylamino | 4-cyclohexylpiperazinyl |
| 221AX | 1-phenylcyclopentylamino | 4-[3-((R)-Boc-amino)-1-pyrrolidyl)piperidinyl |
| 221AY | 4-indanylamino | 4-cyclohexylpiperazinyl |
| 221AZ | 1-phenylcyclopentylamino | (3R)-4-(3-chloroammoniumpyrrolidinyl)piperdinyl |
| 221BA | (R)-1,2,3,4-tetrahydro-1-naphtylamino | 4-(2-fluorophenyl)piperazinyl |
| 221BB | (R)-1,2,3,4-tetrahydro-1-naphtylamino | 4-(3-chlorophenyl)piperazinyl |
| 221BC | (R)-1,2,3,4-tetrahydro-1-naphtylamino | 4-(4-fluorophenyl)piperazinyl |
| 221BD | (R)-1,2,3,4-tetrahydro-1-naphtylamino | 4-ethylpiperazinyl |
| 221BE | (R)-1,2,3,4-tetrahydro-1-naphtylamino | 4-phenylpiperazinyl |
| 221BF | (R)-1,2,3,4-tetrahydro-1-naphtylamino | 4-benzylpiperazinyl |
| 221BG | (R)-1,2,3,4-tetrahydro-1-naphtylamino | 4-methylpiperazinyl |
| 221BH | (R)-1,2,3,4-tetrahydro-1-naphtylamino | 4-(2-methoxyphenyl)piperazinyl |
| 221BI | (R)-1,2,3,4-tetrahydro-1-naphtylamino | 4-(3-OH-n-propyl)piperazinyl |
| 221BJ | (R)-1,2,3,4-tetrahydro-1-naphtylamino | 4-(4-hydroxyphenyl)piperazinyl |

Examples 135-140, shown in the following table, were prepared using the procedure of Example 6, except that N-benzyloxycarbonyl-D-aspartic acid β-t-butyl ester monohydrate was replaced with Example 33, and 3-(trifluoromethyl)benzyl amine was replaced with the appropriate amine; all listed Examples exhibited an $^1$H NMR spectrum consistent with the assigned structure.

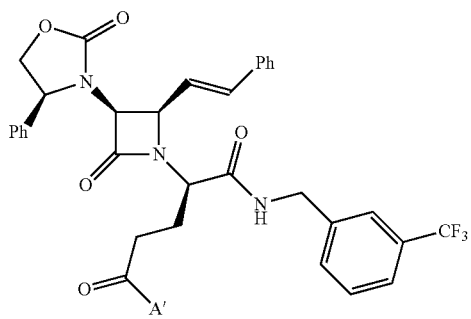

| Example | A' |
|---|---|
| 135 | 4-(piperidinyl)piperidinyl |
| 136 | 4-(2-phenylethyl)piperazinyl |
| 137 | 4-butylpiperazinyl |
| 138 | 4-isopropylpiperazinyl |
| 139 | 4-cyclohexylpiperazinyl |
| 140 | 4-(cyclohexylmethyl)piperazinyl |

Example 140A. 2(R)-(2-(3-trifluoromethylbenzyl)amino-1-ylcarbonyl)ethyl)-2-[3(S)-(4(S)-phenyloxazolidin-2-on-3-yl)-4(R)-(2-styryl)azetidin-2-on-1-yl]acetic acid N-(4-cyclohexyl)piperazinamide Example 140A was prepared using the procedure of Example 6, except that N-benzyloxycarbonyl-D-aspartic acid β-t-butyl ester monohydrate was replaced with Example 34Q, and 3-(trifluoromethyl)benzylamine was replaced with 1-cyclohexylpiperazine, and exhibited an $^1$H NMR spectrum consistent with the assigned structure.

Examples 226-230C, shown in the following table, were prepared using the procedure of Example 6, except that N-benzyloxycarbonyl-D-aspartic acid β-t-butyl ester monohydrate was replaced with Example 34F, and 3-(trifluoromethyl)benzyl amine was replaced with the appropriate amine; all listed Examples exhibited an $^1$H NMR spectrum consistent with the assigned structure.

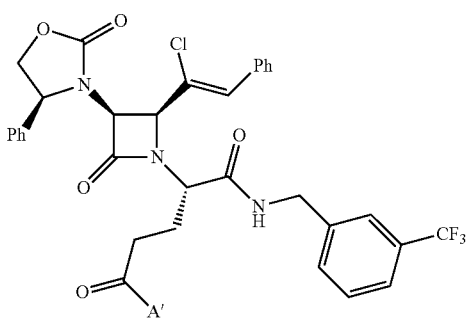

| Example | A' |
|---|---|
| 226 | 4-cyclohexylpiperazinyl |
| 227 | 4-(pyrrolidinyl)piperazinyl |
| 227A | 4-[2-(2-hydroxyethyloxy)ethyl]piperazinyl |
| 227B | 4-benzylpiperazinyl |
| 227C | 4-(3,4-methylendioxybenzyl)piperazinyl |
| 228 | 4-ethylpiperazinyl |
| 229 | 4-n-butylpiperazinyl |
| 230 | 4-isopropylpiperazinyl |
| 230A | 1-benzylpiperidin-4-ylamino |
| 230B | 4-(2-cyclohexylethyl)piperazinyl |
| 230C | 4-[2-(morpholin-4-yl)ethyl]piperazinyl |

The following compounds were prepared according to the processes described herein:

| Example | Y | C(3)-C(4) Stereochemistry | A' |
|---|---|---|---|
| 230D | F | not determined | 4-n-butylpiperazinyl |
| 230E | F | not determined | (R)-1-benzylpyrrolidin-3-amino |
| 230F | F | not determined | quinuclidin-3-ylamino |
| 230G | F | (3S,4R) | (S)-1-benzylpyrrolidin-3-amino |
| 230H | Cl | not determined | (R)-1-benzylpyrrolidin-3-amino |
| 230I | Cl | (3S,4R) | (R)-1-benzylpyrrolidin-3-amino |
| 230J | Cl | (3S,4R) | (S)-1-benzylpyrrolidin-3-amino |
| 230K | Cl | not determined | (S)-1-benzylpyrrolidin-3-amino |
| 230L | Br | not determined | 4-n-butylpiperazinyl |
| 230M | Br | not determined | 4-ethylpiperazinyl |

Example 86C. 2(S)-[[4-(Piperidinyl)piperidinyl]carbonymethyl]-2-[3(S)-(4(R)-phenyloxazolidin-2-on-3-yl)-4(R)-(2-styryl)azetidin-2-on-1-yl]acetic acid N-(3-trifluoromethylbenzyl)amide Example 86C was prepared using the procedure of Example 6, except that N-benzyloxycarbonyl-D-aspartic acid β-t-butyl ester monohydrate was replaced with Example 28A, and 3-(trifluoromethyl)benzyl amine was replaced with 4-(piperidinyl)piperidine, and exhibited an $^1$H NMR spectrum consistent with the assigned structure.

Example 231. 2(R)-[[4-(Piperidinyl)piperidinyl]carbonylmethyl]-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide Example 231 was prepared using the procedure of Example 6, except that N-benzyloxycarbonyl-D-aspartic acid β-t-butyl ester monohydrate was replaced with Example 34G, and 3-(trifluoromethyl)benzyl amine was replaced with 4-(piperidinyl)piperidine, and exhibited an $^1$H NMR spectrum consistent with the assigned structure.

Examples 232-233A, shown in the following table, were prepared using the procedure of Example 6, except that N-benzyloxycarbonyl-D-aspartic acid β-t-butyl ester monohydrate was replaced with Example 34H, and 3-(trifluoromethyl)benzyl amine was replaced with the appropriate amine; all listed Examples exhibited an $^1$H NMR spectrum consistent with the assigned structure.

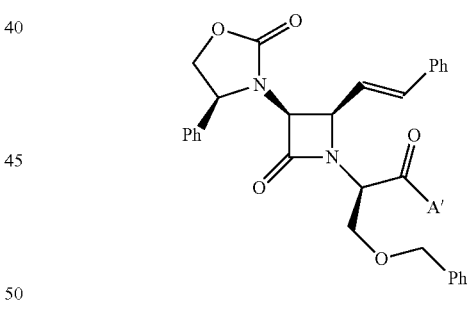

| Example | A' | α |
|---|---|---|
| 232 | 4-(piperidinyl)piperidinyl | D |
| 232A | (3-trifluorobenzyl)amino | D |
| 232B | 4-(3-trifluoromethylphenyl)piperazinyl | D or L |
| 232C | 4-(3-trifluoromethylphenyl)piperazinyl | D or L |
| 232D | 4-cyclohexylpiperazinyl | DL |
| 232E | 4-(piperidinylmethyl)piperidinyl | D |
| 233 | 4-[2-(piperidinyl)ethyl]piperidinyl | D |
| 233A | 4-[(1-piperidyl)methyl]piperidinamide | D |

Example 234. (2RS)-[4-(piperidinyl)piperidinylcarbonyl]-2-methyl-2-[3(S)-(4(S)-phenyloxazolidin-2-on-3-yl)-4(R)-(2-styryl)azetidin-2-on-1-yl]acetic acid N-(3-trifluoromethylbenzyl)amide

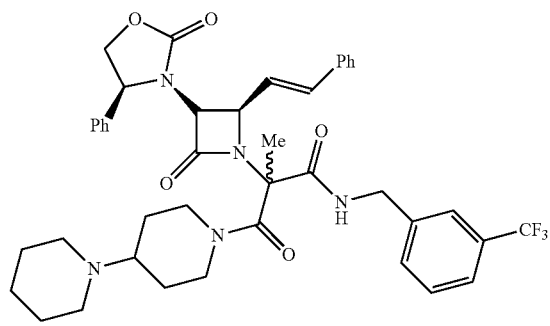

Example 37 (50 mg, 0.067 mmol) in tetrahydrofuran (4 mL) was treated sequentially with sodium hydride (4 mg, 0.168 mmol) and methyl iodide (6 µL, 0.094 mmol) at −78° C. The resulting mixture was slowly warmed to ambient temperature, and evaporated. The resulting residue was partitioned between dichloromethane and water, and the organic layer was evaporated. The resulting residue was purified by silica gel chromatography (95:5 chloroform/methanol) to give 28 mg (55%) of the title compound as an off-white solid; MS (ES⁺): m/z=757 (M⁺).

Example 234A. 4-(Piperidinyl)-piperidinyl 3(R)-[3(S)-(4(S)-phenyloxazolidin-2-on-3-yl)-3-methyl-4(R)-(styr-2-yl)azetidin-2-on-1-yl]-3-[(3-trifluoromethyl)phenylmethylaminocarbonyl]propanoic acid

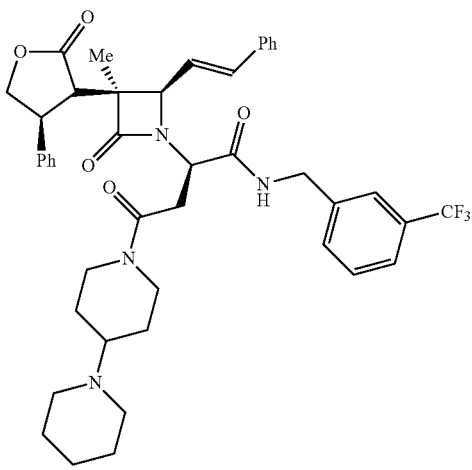 [SMILES: C[C@@]1(C2C(=O)OC[C@@H]2c2ccccc2)C(=O)N([C@H](CC(=O)N2CCC(N3CCCCC3)CC2)C(=O)NCc2cccc(C(F)(F)F)c2)[C@@H]1/C=C/c1ccccc1]

Using the procedure of Example 6, except that N-benzyloxycarbonyl-D-aspartic acid β-t-butyl ester monohydrate was replaced with the carboxylic acid of Example 34J and 3-(trifluoromethyl)benzyl amine was replaced with 4-(piperidinyl)piperidine, the title compound was prepared in quantitative yield; MS (m+H)⁺772.

The compounds shown in the following table were prepared according to the processes described herein.

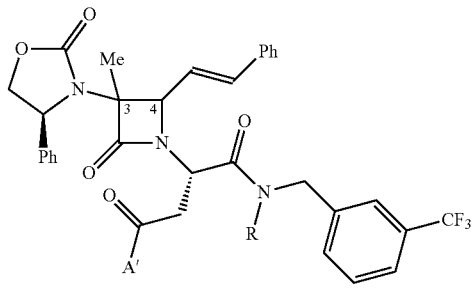

| C(3)-C(4) Stereochemistry | R | A' |
|---|---|---|
| (3S,4R) | H | 4-(piperidyl)piperidinyl |
| (3S,4R) | Me | 4-(piperidyl)piperidinyl |
| not determined | H | 4-(piperidyl)piperidinyl |

Example 235. 2(S)-[[(1-Benzylpiperidin-4-yl)amino]carbonylmethyl]-2-[3(S)-(4(S)-phenyloxazolidin-2-on-3-yl)-4(R)-(2-phenyleth-1-yl)azetidin-2-on-1-yl]acetic acid N-(3-trifluoromethylbenzyl)amide Example 235 was prepared using the procedure of Example 8, except that N-benzyloxycarbonyl-L-aspartic acid β-t-butyl ester α-(3-trifluoromethyl)benzylamide was replaced with Example 63 (50 mg, 0.064 mmol) to give 40 mg (80%) of Example 235 as an off-white solid; Example 235 exhibited an ¹H NMR spectrum consistent with the assigned structure.

Example 236. (2S)-[(4-cyclohexylpiperazinyl)carbonylethyl]-2-[3(S)-(4(S)-phenyloxazolidin-2-on-3-yl)-4(R)-(2-phenyleth-1-yl)azetidin-2-on-1-yl]acetic acid N-(3-trifluoromethylbenzyl)amide Example 236 was prepared using the procedure of Example 8, except that N-benzyloxycarbonyl-L-aspartic acid β-t-butyl ester α-(3-trifluoromethyl)benzylamide was replaced with Example 110 (50 mg, 0.065 mmol) to give 42 mg (84%) of Example 236 as an off-white solid; Example 236 exhibited an ¹H NMR spectrum consistent with the assigned structure.

Example 236A. (2S)-[(4-cyclohexylpiperazinyl)carbonylethyl]-2-[3(S)-(4(S)-phenyloxazolidin-2-on-3-yl)-4(R)-(2-phenyleth-1-yl)azetidin-2-on-1-yl] acetic acid N—[(R)-1,2,3,4-tetrahydronaphth-1-yl]amide Example 236A was prepared using the procedure of Example 8, except that N-benzyloxycarbonyl-L-aspartic acid β-t-butyl ester α-(3-trifluoromethyl)benzylamide was replaced with Example 215 (76 mg, 0.10 mmol) to give 69 mg (90%) of Example 236A as an off white solid. Example 236A exhibited an ¹H NMR spectrum consistent with the assigned structure.

Example 237. 2(R)-[[4-(Piperidinyl)piperidinyl]carbonylmethyl]-2-[3(S)-(4(S)-phenyloxazolidin-2-on-3-yl)-4(R)-(propen-1-yl)azetidin-2-on-1-yl]acetic acid N-(3-trifluoromethylbenzyl)amide Example 237 was prepared using the procedure of Example 6, except that N-benzyloxycarbonyl-D-aspartic acid β-t-butyl ester monohydrate was replaced with Example 34K, and 3-(trifluoromethyl)benzyl amine was replaced with 4-(piperidinyl)piperidine. Example 237 exhibited an ¹H NMR spectrum consistent with the assigned structure.

Example 238. (2S)-(Benzylthiomethyl)-2-[3(S)-(4 (S)-phenyloxazolidin-2-on-3-yl)-4(R)-(2-styryl)azetidin-2-on-1-yl]acetic acid N-[4-[2-(piperid-1-yl) ethyl]piperidin-1-yl]amide This Example was prepared using the procedure of Example 6, except that N-benzyloxycarbonyl-D-aspartic acid β-t-butyl ester monohydrate was replaced with the coresponding benzyl protected cycteine analog, and 3-(trifluoromethyl)benzyl amine was replaced with 4-[2-(piperid-1-yl)ethyl]piperidine.

Step 1. N-tButyloxycarbonyl-(S)-(benzyl)-D-cysteine-[4-(2-(1-piperidyl)ethyl)]piperidinenamide. N-tButyloxycarbonyl-(S)-Benzyl-N-(tbutyloxycarbonyl)-D-cysteine (0.289 g, 0.93 mmole) and 4-[2-(1-piperidyl)ethyl]piperidine (0.192 g, 0.98 mmole) in dichloromethane (20 mL) gave 0.454 g (quantitative yield) of Example X as an off-white solid. ¹H NMR (CDCl₃) δ 0.89-1.15 (m, 2H); 1.39-1.44 (m, 16H); 1.54-1.61 (m, 4H); 1.62-1.71 (m, 1H); 2.21-2.35 (m, 5H); 2.49-2.58 (m, 2H); 2.66-2.74 (m, 1H); 2.79-2.97 (m, 1H); 3.67-3.76 (m, 3H); 4.48-4.51 (m, 1H); 4.72-4.75 (m, 1H); 5.41-5.44 (m, 1H); 7.19-7.34 (m, 5H).

Step 2. (S)-(benzyl)-D-cysteine-[4-(2-(1-piperidyl)ethyl)] piperidinenamide, dihydrochloride. N-tButyloxycarbonyl-(S)-(benzyl)-D-cysteine-[4-(2-(1-piperidyl)ethyl)]piperidinenamide (0.453 g, 0.93 mmole) was reacted overnight with acetyl chloride (0.78 mL, 13.80 mmole) in anhydrous methanol (15 mL). The title compound was obtained as an off-white solid by evaporating the reaction mixture to dryness (0.417 g, 97%). ¹H NMR (CD₃OD) δ 0.94-1.29 (m, 2H); 1.49-1.57 (m, 1H); 1.62-1.95 (m, 10H); 2.65-2.80 (m, 2H); 2.81-2.97 (m, 4H); 3.01-3.14 (m, 2H); 3.50-3.60 (m, 3H); 3.81-3.92 (m, 2H); 4.41-4.47 (m, 2H); 7.25-7.44 (m, 5H).

Step 3. Using the general procedures described herein, the imine prepared from (S)-(benzyl)-D-cysteine-[4-(2-(1-piperidyl)ethyl)]piperidinenamide, dihydrochloride (0.417 g, 0.90 mmole) and cinnamaldehyde, in the presence on triethylamine (0.26 mL, 1.87 mmole), was combined with 2-(4(S)-phenyloxazolidin-2-on-3-yl) acetyl chloride (Example 1) to give 0.484 g (76%) of Example 238 as an off-white solid after recrytallization from dichloromethane/hexanes. ¹H NMR (CDCl₃) δ 0.89-1.06 (m, 2H); 1.40-1.44 (m, 5H); 1.57-1.67 (m, 6H); 2.25-2.43 (m, 6H); 2.45-2.59 (m, 2H); 2.71-2.88 (m, 2H); 3.55-3.70 (m, 3H); 4.11-4.17 (m, 1H); 4.37-4.47 (m, 2H); 4.54-4.61 (m, 1H); 4.64-4.69 (m, 1H); 4.76-4.84 (m, 2H); 6.05-6.19 (m, 1H); 6.66-6.71 (m, 1H); 7.12-7.40 (m, 15H).

The following compounds are described

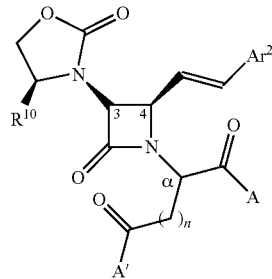

| Example | R¹⁰ | Ar² | n | α | A | A' |
|---|---|---|---|---|---|---|
| 239 | Ph | Ph | 2 | L | 1-Ph-cyclopentylamino | 4-ethylpiperazin-1-yl |
| 240 | Ph | Ph | 2 | L | 1-Ph-cyclopentylamino | 4-benzylpiperazin-1-yl |
| 241 | Ph | Ph | 2 | L | (R)-1,2,3,4-tetrahydronaphth-1-ylamino | 4-cyclopentylpiperazin-1-yl |
| 242 | Ph | 3-MeO-Ph | 2 | L | (R)-1,2,3,4-tetrahydronaphth-1-ylamino | 4-cyclohexylpiperazin-1-yl |
| 243 | Ph | 3-Cl-Ph | 2 | L | (R)-1,2,3,4-tetrahydronaphth-1-ylamino | 4-cyclohexylpiperazin-1-yl |
| 244 | Ph | 3-Cl-Ph | 2 | L | 1-phenyl-cyclopent-1-ylamino | 4-cyclohexylpiperazin-1-yl |
| 245 | Ph | 3-F-Ph | 2 | L | (R)-1,2,3,4-tetrahydronaphth-1-ylamino | 4-cyclohexylpiperazin-1-yl |
| 246 | Ph | 3-CF₃-Ph | 2 | L | (R)-1,2,3,4-tetrahydronaphth-1-ylamino | 4-cyclohexylpiperazin-1-yl |
| 247 | Ph | 3-Cl-Ph | 1 | D | N-methyl-3-CF₃-benzylamino | 4-(1-piperidyl)piperidin-1-yl |
| 248 | Ph | 3-CN-Ph | 2 | L | (R)-1,2,3,4-tetrahydronaphth-1-ylamino | 4-cyclohexylpiperazin-1-yl |
| 249 | Ph | 3-NO₂-Ph | 2 | L | (R)-1,2,3,4-tetrahydronaphth-1-ylamino | 4-cyclohexylpiperazin-1-yl |
| 250 | Ph | 2-Cl-Ph | 2 | L | (R)-1,2,3,4-tetrahydronaphth-1-ylamino | 4-cyclohexylpiperazin-1-yl |
| 251 | 3-Cl-Ph | 3-Cl-Ph | 2 | L | (R)-1,2,3,4-tetrahydronaphth-1-ylamino | 4-cyclohexylpiperazin-1-yl |
| 252 | Ph | 3,5-Cl₂-Ph | 2 | L | (R)-1,2,3,4-tetrahydronaphth-1-ylamino | 4-cyclohexylpiperazin-1-yl |
| 253 | Ph | Ph | 1 | L | (S)-1-Ph-ethylamino | 4-(1-piperidyl)piperidin-1-yl |

-continued

| Example | R¹⁰ | Ar² | n | α | A | A' |
|---|---|---|---|---|---|---|
| 256 | 3-Cl-Ph | Ph | 1 | D | (R)-1-Ph-ethylamino | 4-(1-piperidyl)piperidin-1-yl |
| 266 | Ph | 3-I-Ph | 1 | D | (R)-1-Ph-ethylamino | 4-(1-piperidyl)piperidin-1-yl |

The following compounds are described

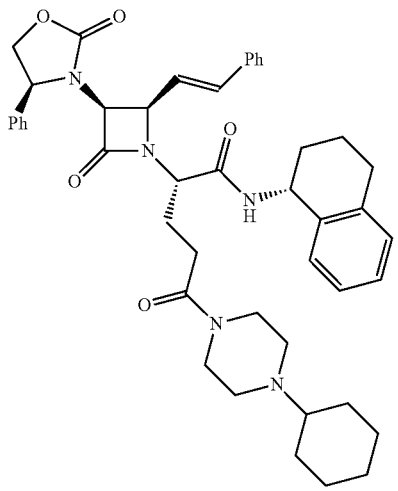 [SMILES: O=C(N[C@@H]1CCCc2ccccc21)[C@H](CCC(=O)N1CCN(C2CCCCC2)CC1)N1C(=O)[C@@H](N2C(=O)OC[C@@H]2c2ccccc2)[C@H]1/C=C/c1ccccc1]

| Example | Ar |
|---|---|
| 257 | benzothiophen-7-yl |
| 254 | fur-2-yl |
| 255 | thien-2-yl |

The following compounds are described

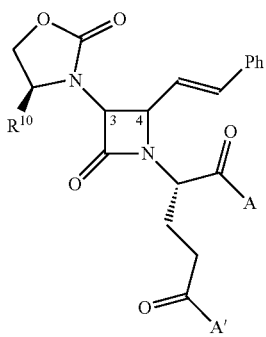

| Example | R¹⁰ | Stereochemistry | A | A' |
|---|---|---|---|---|
| 258 | Ph | (3S,4R) | (R)-1,2,3,4-tetrahydronaphth-1-ylamino | 4-cycloheptylpiperazin-1-yl |
| 259 | Ph | (3S,4R) | (R)-1,2,3,4-tetrahydronaphth-1-ylamino | 4-(tetrahydrothiopyran-4-yl)piperazin-1-yl |
| 260 | Ph | (3R,4S) | 3-CF₃-benzylamino | 4-cyclohexylpiperazin-1-yl |
| 261 | Ph | (3S,4R) | 4-phenylpiperazin-1-yl | 3-F-5-CF₃-benzylamino |
| 262 | Ph | (3S,4R) | 4-(2-cyclohexylethyl)piperazin-1-yl | 3-F-5-CF₃-benzylamino |
| 263 | Ph | (3S,4R) | 4-(pyrid-2-yl)piperazin-1-yl | 3-F-5-CF₃-benzylamino |
| 264 | Ph | (3S,4R) | 4-(2-thien-2-ylethyl)piperazin-1-yl | 3-F-5-CF₃-benzylamino |
| 265 | 3-Cl—Ph | (3S,4R) | (R)-α-methylbenzylamino | 4-cyclohexylpiperazin-1-yl |

The following compounds are described

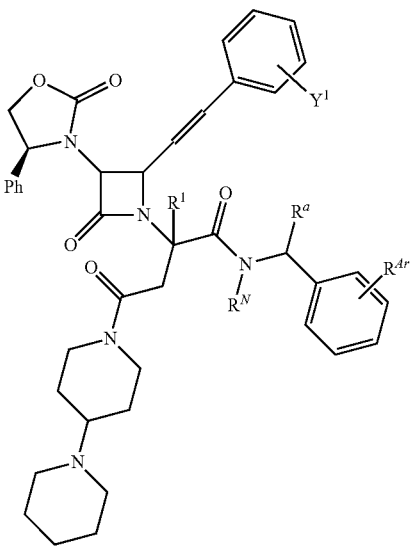

| Example | Y¹ | R^N | R^a | R^{Ar} |
|---|---|---|---|---|
| 559 | 3-Cl | H | (R)—Me | H |
| 594 | 4-OH | H | (R)—Me | H |
| 597 | 3-NO₂ | H | (R)—Me | H |
| 600 | 3-NH₂ | H | (R)—Me | H |
| 606 | 3-Br | H | (R)—Me | H |
| 633 | 3-F | H | (R)—Me | H |
| 778 | 3-Me | H | (R)—Me | H |
| 623 | H | H | (R)—CF₃ | H |
| 626 | H | H | (S)—CF₃ | H |
| 682 | H | H | H | 2-Br |
| 677 | H | H | H | 2-F |
| 617 | 3-Br | Me | H | 3-CF₃ |

The following compounds are described

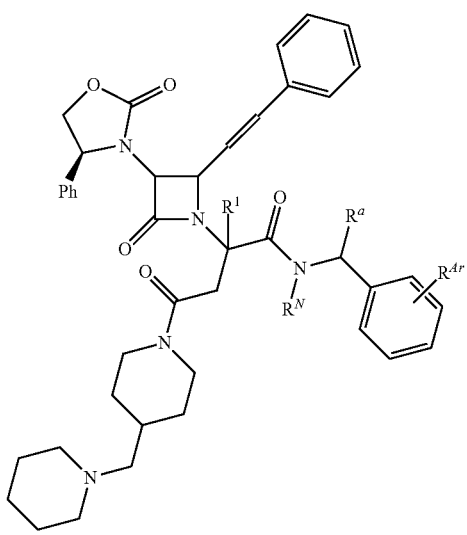
| Example | $R^N$ | $R^a$ | $R^{Ar}$ |
|---|---|---|---|
| 599 | Me | H | 3-CF$_3$ |
| 601 | H | (R)—Me | H |
The following compounds are described
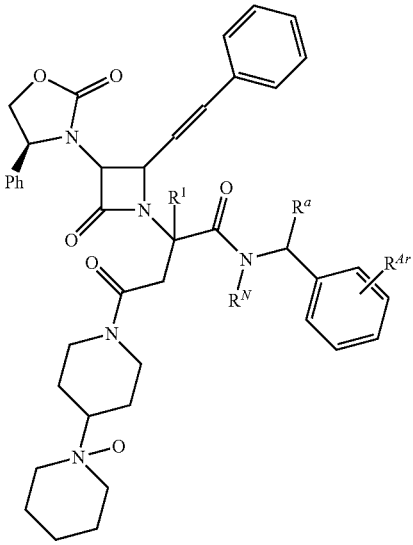
| Example | $R^N$ | $R^a$ | $R^{Ar}$ |
|---|---|---|---|
| 670 | Me | H | 3-CF$_3$ |
| 672 | H | (R)—Me | H |
The following table illustrates selected compounds further characterized by mass spectral analysis using FAB$^+$ to observe the corresponding (M+H)$^+$ parent ion.
| Example | (m + H)$^+$/z |
|---|---|
| 37 | 744 |
| 38 | 766 |
| 39 | 766 |
| 40 | 718 |
| 41 | 704 |
| 42 | 744 |
| 42A | 772 |
| 44 | 758 |
| 63 | 780 |
| 85 | 766 |
| 86A | 786 |
| 86C | 758 |
| 88 | 772 |
| 91 | 759 |
| 95 | 780 |
| 96 | 824 |
| 104 | 732 |
| 110 | 772 |
| 111 | 800 |
| 112 | 803 |
| 120 | 786 |
| 120A | 800 |
| 120B | 732 |
| 120E | 788 |
| 132B | 758 |
| 133 | 758 |
| 134A | 786 |
| 134C | 780 |
| 134H | 772 |
| 136 | 794 |
| 137 | 746 |
| 138 | 732 |
| 139 | 772 |
| 174 | 772 |
| 175 | 772 |
| 176 | 772 |
| 177 | 790 |
| 179 | 790 |
| 180 | 790 |
| 182 | 772 |
| 183 | 734 |
| 184 | 722 |
| 185 | 740 |
| 186 | 756 |
| 187 | 738 |
| 188 | 840 |
| 189 | 749 |
| 190 | 782 |
| 191 | 704 |
| 192 | 718 |
| 193 | 718 |
| 199 | 732 |
| 200 | 718 |
| 201 | 764 |
| 202 | 748 |
| 203 | 748 |
| 205 | 786 |
| 206 | 718 |
| 207 | 730 |
| 208 | 705 |
| 209 | 705 |
| 210 | 705 |
| 211 | 694 |
| 212 | 708 |
| 213 | 710 |
| 214 | 744 |
| 215 | 744 |
| 216 | 7530 |
| 217 | 758 |
| 218 | 792 |
| 219 | 764 |
| 220 | 734 |
| 221 | 746 |
| 222 | 776 |
| 224 | 704 |
| 225 | 772 |
| 226 | 806 |
| 227 | 792 |
| 228 | 752 |

-continued

| Example | (m + H)⁺/z |
|---------|------------|
| 229 | 780 |
| 230 | 766 |
| 231 | 788 |
| 232 | 663 |
| 233 | 691 |
| 234 | 758 |
| 235 | 782 |
| 236 | 774 |

What is claimed is:

1. A unit dose comprising about 80 mg to about 700 mg total of one or more compounds of the formulae (I)

or a salt thereof, wherein
- A and A' are each independently selected from —$CO_2H$, or an ester or amide derivative thereof;
- n is an integer selected from 0 to about 3;
- $R^1$ is hydrogen or $C_1$-$C_6$ alkyl;
- $R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form an heterocycle; and where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);
- $R^3$ is an amino, amido, acylamido, or ureido group, which is optionally substituted; or $R^3$ is a nitrogen-containing heterocyclyl group attached at a nitrogen atom; and
- $R^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl; or (II)

or a salt thereof, wherein
- Q is oxygen; or Q is sulfur or disulfide, or an oxidized derivative thereof;
- n is an integer from 1 to 3; and
- $R^{5''}$ is selected from hydrogen, alkyl, cycloalkyl, alkoxyalkyl, optionally substituted arylalkyl, optionally substituted heterocyclyl or optionally substituted heterocyclylalkyl, and optionally substituted aminoalkyl,
- where the unit dose is adapted for treating Huntington's Disease in a human, where the one or more compounds are selective for the V1a receptor compared to the V1b receptor by a factor of about 10 or greater.

2. The unit dose of claim 1 wherein $R^1$ is hydrogen; and $R^2$ is hydrogen or alkyl.

3. The unit dose of claim 1 wherein $R^3$ is of the formulae:

wherein $R^{10}$ and $R^{11}$ are each independently selected from the group consisting of hydrogen, optionally substituted alkyl, optionally substituted cycloalkyl, alkoxycarbonyl, alkylcarbonyloxy, optionally substituted aryl, optionally substituted arylalkyl, optionally substituted arylalkyloxy, optionally substituted arylalkylcarbonyloxy, diphenylmethoxy, and triphenylmethoxy; and $R^{12}$ is selected from the group consisting of hydrogen, alkyl, cycloalkyl, alkoxycarbonyl, optionally substituted aryloxycarbonyl, optionally substituted arylalkyl, and optionally substituted aryloyl.

4. The unit dose of claim 3 wherein R³ is

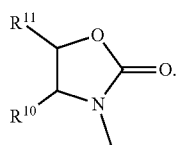

5. The unit dose of claim 1 wherein n is 1 or 2.
6. The unit dose of claim 1 wherein R⁴ is of the formulae:

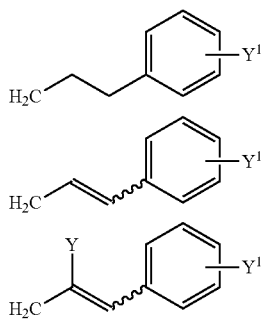

wherein Y is an electron withdrawing group, and Y¹ is hydrogen or one or more aryl substituents.

7. The unit dose of claim 1 wherein one or both of A and A' is an independently selected amido of the formula C(O)NHX or C(O)NR¹⁴X, where R¹⁴ is selected from the group consisting of hydroxy, alkyl, alkoxycarbonyl, and benzyl; and X is selected from the group consisting of alkyl, cycloalkyl, alkoxyalkyl, optionally substituted aryl, optionally substituted arylalkyl, heterocyclyl, heterocyclyl-($C_1$-$C_4$ alkyl), R⁶R⁷N—, and R⁶R⁷N—($C_2$-$C_4$ alkyl), where each heterocyclyl is independently selected.

8. The unit dose of claim 1 wherein one or both of A and A' is an amide of an independently selected optionally substituted nitrogen-containing heterocycle attached at a nitrogen, and selected from the group consisting of pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl.

9. The unit dose of claim 1 wherein one or both of A and A' is an amide of an optionally substituted 1,2,3,4-tetrahydroisoquinolin-2-yl.

10. The unit dose of claim 1 comprising the compound of formula (I) wherein A is of the formula C(O)NHX or C(O)NR¹⁴X, where R¹⁴ is selected from the group consisting of hydroxy, alkyl, alkoxycarbonyl, and benzyl; and X is selected from the group consisting of alkyl, cycloalkyl, alkoxyalkyl, optionally substituted aryl, optionally substituted arylalkyl, heterocyclyl, heterocyclyl-($C_1$-$C_4$ alkyl), R⁶R⁷N—, and R⁶R⁷N—($C_2$-$C_4$ alkyl).

11. The unit dose of claim 1 wherein A is of the formula

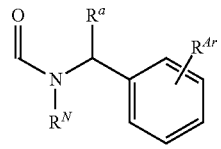

where $R^N$ is hydrogen or optionally substituted alkyl, or an amide prodrug forming group; $R^a$ is hydrogen or optionally substituted alkyl; and $R^{Ar}$ is hydrogen or one or more aryl substituents.

12. The unit dose of claim 1 comprising the compound of formula (I) wherein A' is an amide of an optionally substituted nitrogen-containing heterocycle attached at a nitrogen, and selected from the group consisting of pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl.

13. The unit dose of claim 1 comprising the compound of formula (I) wherein A' is an amide of a substituted piperidine or piperazine.

14. The unit dose of claim 1 comprising the compound of formula (II) wherein A is an amide of an optionally substituted nitrogen-containing heterocycle attached at a nitrogen, and selected from the group consisting of pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl.

15. The unit dose of claim 1 comprising the compound of formula (II) wherein A is an amide of a substituted piperidine or piperazine.

16. The unit dose of claim 1 comprising the compound of formula (II) wherein Q is oxygen or sulfur.

17. The unit dose of claim 1 comprising the compound of formula (II) wherein R⁵‴ is optionally substituted aryl($C_2$-$C_4$ alkyl).

18. The unit dose of claim 1 comprising about 80 to about 350 mg total of the one of more compounds of formulae (I) or (II).

19. The unit dose of claim 1 in a divided format.

20. The unit dose of claim 1 adapted for treating the neuropsychiatric symptoms of Huntington's Disease.

21. The unit dose of claim 20 wherein the neuropsychiatric symptoms include aggression, irritability, or anger, or a combination thereof.

22. The unit dose of claim 20 comprising a compound of the formula

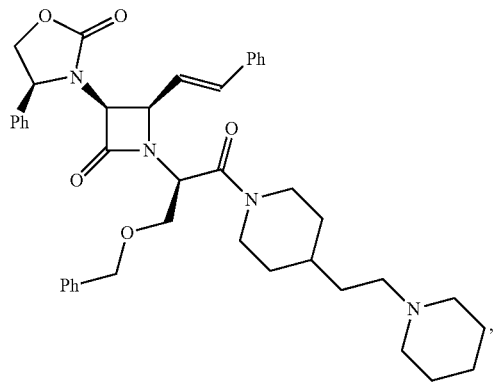

103
-continued
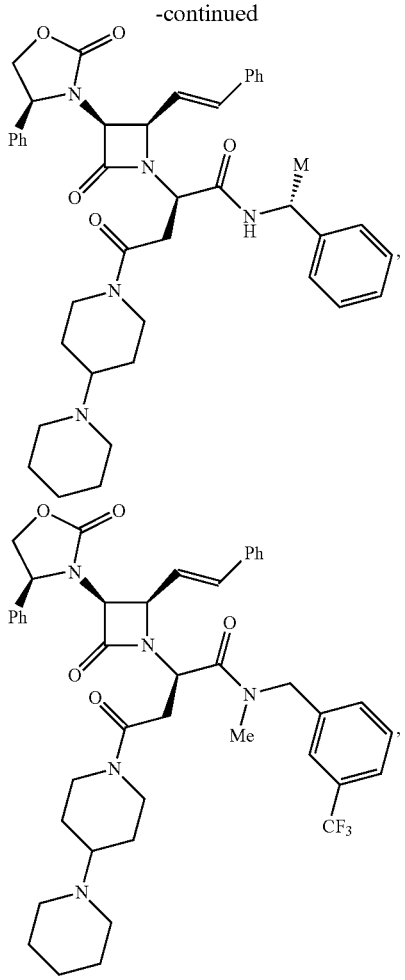
104
-continued
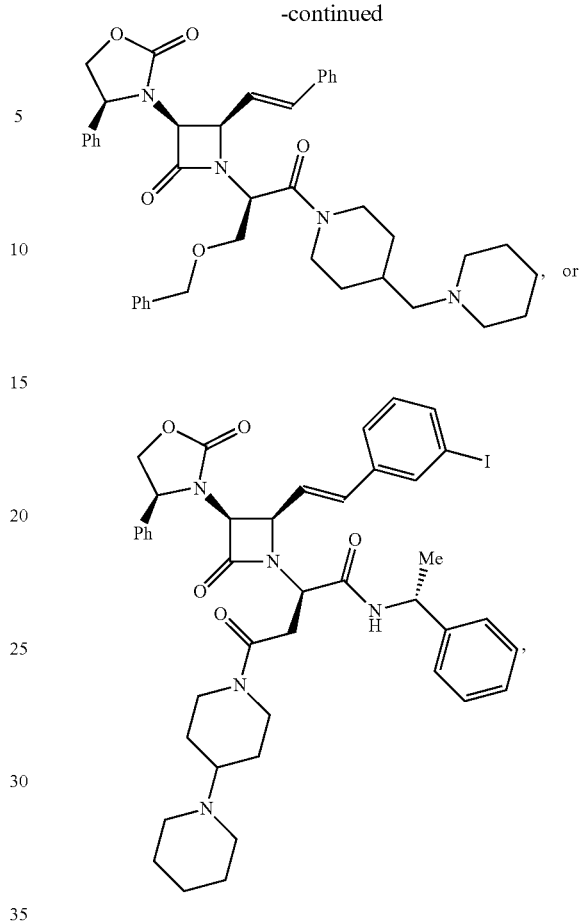
or a salt thereof, or a combination of the foregoing.
* * * * *

UNITED STATES PATENT AND TRADEMARK OFFICE
CERTIFICATE OF CORRECTION

PATENT NO. : 10,364,236 B2
APPLICATION NO. : 15/786772
DATED : July 30, 2019
INVENTOR(S) : Michael J. Brownstein It is certified that error appears in the above-identified patent and that said Letters Patent is hereby corrected as shown below:

In the Specification

In Column 1, Line 20:
"This invention was made with government support under R44MH063663 awarded by the National Institute of Mental Health. The government has certain rights in the invention." should read --This invention was made with government support under U44 NS090616 awarded by the National Institute of Neurological Disorders and Stroke. The government has certain rights in the invention.--.

Signed and Sealed this
Twenty-eighth Day of January, 2020

Andrei Iancu
*Director of the United States Patent and Trademark Office*